(12) United States Patent
Lu et al.

(10) Patent No.: US 7,067,512 B2
(45) Date of Patent: Jun. 27, 2006

(54) SUBSTITUTED 1,4-BENZODIAZEPINES AND USES THEREOF

(76) Inventors: Tianbao Lu, 606 Monticello La., Kennett Square, PA (US) 19348; Louis V Lafrance, III, 936 Cedarwood Ave., West Chester, PA (US) 19380; Daniel J Parks, 106 N. Severgn Dr., Exton, PA (US) 19341; Karen L Milkiewicz, 408 Cadwalader Cir., Exton, PA (US) 19341; Raul R Calvo, 72 Orchard Ct., Royersford, PA (US) 19468; Maxwell D Cummings, 659 W. Valley Rd., Wayne, PA (US) 19087; Alexander J Kim, 4708 Oxford Ave., Philadelphia, PA (US) 19124; Bruce L Grasberger, 335 Meadowview Dr., Trappe, PA (US) 19426; Theodore E Carver, Jr., 276 Meadowlake Dr., Downingtown, PA (US) 19335

( * ) Notice: Subject to any disclaimer, the term of this patent is extended or adjusted under 35 U.S.C. 154(b) by 365 days.

(21) Appl. No.: 10/292,876

(22) Filed: Nov. 13, 2002

(65) Prior Publication Data

US 2003/0109518 A1   Jun. 12, 2003

Related U.S. Application Data

(60) Provisional application No. 60/331,235, filed on Nov. 13, 2001.

(51) Int. Cl.
| | |
|---|---|
| C07D 243/12 | (2006.01) |
| C07D 243/18 | (2006.01) |
| C07D 243/24 | (2006.01) |
| A61K 31/55 | (2006.01) |

(52) U.S. Cl. .................. 514/221; 540/504; 540/505; 540/506; 540/512
(58) Field of Classification Search ............. 540/504, 540/505, 506, 512; 514/221
See application file for complete search history.

(56) References Cited

U.S. PATENT DOCUMENTS

| | | | |
|---|---|---|---|
| 5,250,679 A | 10/1993 | Blackburn et al. | |
| 5,272,158 A | 12/1993 | Hartman et al. | |
| 5,389,631 A | 2/1995 | Claremon et al. | |
| 5,441,952 A | 8/1995 | Claremon et al. | |
| 5,795,887 A | 8/1998 | Aquino et al. | |
| 5,817,751 A | 10/1998 | Szardenings et al. | |
| 5,990,145 A | 11/1999 | Wehner et al. | |
| 6,492,553 B1 * | 12/2002 | Hulme et al. | 564/129 |
| 6,600,016 B1 * | 7/2003 | Campian et al. | 530/334 |

FOREIGN PATENT DOCUMENTS

| | | |
|---|---|---|
| WO | WO 99/38844 | 8/1999 |
| WO | WO 00/56721 | 9/2000 |
| WO | WO 00/66106 | 11/2000 |
| WO | WO 01/04103 A1 | 1/2001 |
| WO | WO 01/10799 A1 | 2/2001 |

OTHER PUBLICATIONS

Barak, Y., and Oren, M., "Enhanced binding of a 95 kDa protein to p53 in cells undergoing p53-mediated growth arrest," *EMBO J.* 11:2115-2121, Oxford University Press (1992).

Barak, Y., et al., "*mdm2* expression is induced by wild type p53 activity," *EMBO J.* 12:461-468, Oxford University Press (1993).

Cahilly-Snyder, L., et al., "Molecular Analysis and Chromosomal Mapping of Amplified Genes Isolated from a Transformed Mouse 3T3 Cell Line," *Somat. Cell Mol. Genet.* 13:235-244, Plenum Publishing Corporation (1987).

(Continued)

*Primary Examiner*—Bruck Kifle
(74) *Attorney, Agent, or Firm*—Laura Donnelly

(57) ABSTRACT

The present invention is directed to novel 1,4-benzodiazepines, pharmaceutical compositions thereof, and the use thereof as inhibitors of HDM2-p53 interactions. Compounds have Formula I:

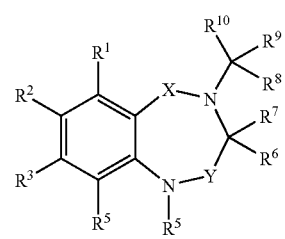

or a solvate, hydrate or pharmaceutically acceptable salt thereof; wherein:

X and Y are independently —C(O)—, —CH$_2$— or —C(S)—;

$R^1$, $R^2$, $R^3$, $R^4$, $R^7$, $R^8$, $R^b$, $R^c$, $R^d$ and M are defined herein;

$R^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

$R^6$ is cycloalkyl, aryl, heteroaryl, cycloalkylalkyl, aralkyl, heteroarylalkyl, or a saturated or partially unsaturated heterocycle, each of which is optionally substituted;

$R^9$ is cycloalkyl, aryl, heteroaryl, a saturated or partially unsaturated heterocycle, cycloalkyl(alkyl), aralkyl or heteroarylalkyl, each of which is optionally substituted; and $R^{10}$ is —(CH$_2$)$_n$—CO$_2$R$^b$, —(CH$_2$)$_m$—CO$_2$M, —(CH$_2$)$_i$—OH or —(CH$_2$)$_j$—CONR$^c$R$^d$ n is 0–8, m is 0–8, i is 1–8 and j is 0–8.

33 Claims, No Drawings

OTHER PUBLICATIONS

El-Deiry, W.S., et al., "*WAF1*, a Potential Mediator of p53 Tumor Suppression," *Cell 75*:817-825, Cell Press (1993).

Farmer, G., et al., "Wild-type p53 activates transcription *in vitro*," *Nature 358*:83-86, Nature Publishing Company (1992).

Funk, W.D., et al., "A Transcriptionally Active DNA-Binding Site for Human p53 Protein Complexes," *Mol. Cell Biol. 12*:2866-2871, American Society for Microbiology (1992).

Harper, J.W., et al., "The p21 Cdk-Interacting Protein Cip1 Is a Potent Inhibitor of G1 Cyclin-Dependent Kinases," *Cell 75*:805-816, Cell Press (1993).

Hulme, C., et al., "Improved Procedure for the Solution Phase Preparation of 1,4-Benzodiazepine-2,5-dione Libraries via Armstrong's Convertible Isonitrile and the Ugi Reaction," *J. Org. Chem. 63*:8021-8023, American Chemical Society (1998).

Hulme, C., et al., "Novel Safety-Catch Linker and its Application with a Ugi/De-BOC/Cyclization (UDC) Strategy to access Carboxylic acids, 1,4-Benzodiazepines, Diketopiperazines, Ketopiperazines and Dihydroquinoxalinones," *Tetrahedron Lett. 39*:7227-7230, Pergamon Press (1998).

Hulme, C., et al., "Novel applications of resin bound α-amino acids for the synthesis of benzodiazepines (via Wang resin) and ketopiperazines (via hydroxymethyl resin)," *Tetrahedron Lett. 41*:1509-1514, Pergamon Press (Mar. 2000).

Kastan, M.B., et al., "A Mammalian Cell Cycle Checkpoint Pathway Utilizing p53 and *GADD45* Is Defective in Ataxia-Telangiectasia," *Cell 71*:587-597, Cell Press (1992).

Keating, T.A., and Armstrong, R.W., "A Remarkable Two-Step Synthesis of Diverse 1,4-Benzodiazepine-2,5-diones Using the Ugi Four-Component Condensation," *J. Org. Chem. 61*:8935-8939, American Chemical Society (1996).

Kern, S.E., et al., "Oncogenic Forms of p53 Inhibit p53-Regulated Gene Expression," *Science 256*:827-830, American Association for the Advancement of Science (1992).

Levine, A.J., "p53, the Cellular Gatekeeper for Growth and Division," *Cell 88*:323-331, Cell Press (1997).

Michalovitz, D., et al., "Conditional Inhibition of Transformation and of Cell Proliferation by a Temperature-Sensitive Mutant of p53," *Cell 62*:671-680, Cell Press (1990).

Momand, J., et al., "The *mdm-2* Oncogene Product Forms a Complex with the p53 Protein and Inhibits p53-Mediated Transactivation," *Cell 69*:1237-1245, Cell Press (1992).

Momand, J., et al., "The *MDM2* gene amplification database," *Nucl. Acids Res. 26*:3453-3459, Oxford University Press (1998).

Oliner, J.D., et al., "Amplification of a gene encoding a p53-associated protein in human sarcomas," *Nature 358*:80-83, Nature Publishing Company (1992).

Weintraub, H., et al., "The MCK enhancer contains a p53 responsive element," *Proc. Natl. Acad. Sci. USA 88*:4570-4571, National Academy of Sciences (1991).

Wu, X., et al., "The p53-mdm-2 autoregulatory feedback loop," *Genes Dev. 7*:1126-1132, Cold Spring Harbor Laboratory Press (1993).

Zambetti, G.P., et al., "Wild-type p53 mediates positive regulation of gene expression through a specific DNA sequence element," *Genes Dev. 6*:1143-1152, Cold Spring Harbor Laboratory Press (1992).

Zauberman, A., et al., "Sequence-specific DNA binding by p53: identification of target sites and lack of binding to p53-MDM2 complexes," *EMBO J. 12*:2799-2808, Oxford University Press (1993).

Zhang, R., and Wang, H., "MDM2 Oncogene as a Novel Target for Human Cancer Therapy," *Curr. Pharm. Des. 6*:393-416, Bentham Science Publishers B.V. (Mar. 2000).

\* cited by examiner

SUBSTITUTED 1,4-BENZODIAZEPINES AND USES THEREOF

This application claims priority under 35 U.S.C. § 119(e) to U.S. Provisional Application No. 60/331,235, filed Nov. 13, 2001, which is fully incorporated by reference herein.

BACKGROUND OF THE INVENTION

1. Field of the Invention

The present invention is in the area of novel 1,4-benzodiazepines and salts thereof, their syntheses, and their use as inhibitors of MDM2 and HDM2 oncoproteins.

2. Related Art

This invention relates to compounds that bind to the human protein HDM2 and interfere with its interaction with other proteins, especially the tumor suppressor protein p53. HDM2 is the expression product of hdm2, an oncogene that is overexpressed in a variety of cancers, especially soft tissue sarcomas (Momand, J., et al., *Nucl. Acids Res.* 26:3453–3459 (1998)).

p53 is a transcription factor that plays a pivotal role in the regulation of the balance between cell proliferation and cell growth arrest/apoptosis. Under normal conditions, the half-life of p53 is very short, and consequently the level of p53 in cells is low. However, in response to cellular DNA damage, cellular stress, or other factors, levels of p53 increase. This increase in p53 levels in turn increases the transcription of a number of genes which induces the cell to either arrest growth or undergo apoptosis (i.e., controlled cell death). The function of p53 is to prevent the uncontrolled proliferation of cells and thus protect the organism from the development of cancer (for a review, see Levine, A. J., *Cell* 88:323–331 (1997)).

p53 is a latent and short-lived transcription factor which is induced by, and is an integration point for, a range of cellular stresses including DNA damage, UV damage, spindle damage, hypoxia, inflammatory cytokines, viral infection, activated oncogenes, and ribonucleotide depletion. Activation of p53 mediates a change in the balance of gene expression such that expression of many genes involved in proliferation is repressed while a range of genes involved in growth arrest (such as p21WAF1 and GADD45), repair (such as p53RE) and apoptosis (such as Bax, Killer/DR5 and PIGs) is activated. The biological outcome of p53 activation (whether permanent or transient growth arrest or apoptosis) is dependent on several factors including the type and strength of the inducing stress, and the type of cell or tissue.

p53 and MDM2 exist in a negative regulatory feedback loop in which p53 stimulates transcription of the mdm2 gene while MDM2 binds to p53 and targets it for degradation by the 26S proteosome. The key element in the p53induction process is disruption of the p53-MDM2 complex which permits p53 to accumulate in the nucleus. This mechanism appears to be common to all of the pathways by which p53 becomes activated, although recent evidence has indicated that there is considerable variation in the molecular events by which this is actually achieved.

Inactivation of the p53 tumor suppressor is a frequent event in human neoplasia. The inactivation can occur by mutation of the p53 gene or through binding to viral or cellular oncogene proteins, such as the SV40 large T antigen and MDM2. While the mechanism through which wild-type p53 suppresses tumor cell growth is as yet poorly defined, it is clear that one key feature of the growth suppression is the property of p53 to act as a transcription factor (Farmer, G., et al., *Nature* 358: 83–86 (1992); Funk, W. D. et al., *Mol. Cell. Biol.* 12: 2866–2871 (1992); Kern, S. E., et al., *Science* 256:827–830 (1992)). Currently, considerable effort is being made to identify growth control genes that are regulated by p53 binding to sequence elements near or within these genes. A number of such genes have been identified. In cases such as the muscle creatine kinase gene (Weintraub, H., et al., *Proc. Natl. Acad. Sci. U.S.A.*, 88:4570–4571 (1991); Zambetti, G. P., et al., *Genes Dev.* 6:1143–1152 (1992)) and a GLN retroviral element (Zauberman, A., et al., *EMBO J.* 12:2799–2808 (1993)), the role these genes might play in the suppression of growth control is unclear. Yet there are other examples, namely mdm2 (Barak, Y., et al. *EMBO J.* 12:461–468 (1993); Wu, X., et al., *Genes Dev.* 7:1126–1132 (1993)) GADD 45 (Kastan, M. B., et al., *Cell* 71:587–597 (1992)) and WAF1 or CIP1 (El-Beiry, W. S., et al., *Cell* 75:817–825 (1993); Harper, J. W., et al., *Cell* 75:805–816 (1993)), where their involvement in the regulation of cell growth is better understood.

mdm2, a known oncogene, was originally found on mouse double minute chromosomes (Cahilly-Snyder., L., et al., *Somatic Cell Mol. Genet.* 13:235–244 (1987)). Its protein product was subsequently found to form a complex with p53, which was first observed in a rat fibroblast cell line (Clone 6) previously transfected with a temperature sensitive mouse p53 gene (Michalovitz, D., et al., *Cell* 62:671–680 (1990)). The rat cell line grew well at 37° C. but exhibited a G1 arrest when shifted down to 32° C., which was entirely consistent with an observed temperature dependent switch in p53 conformation and activity. However, the p53-MDM2 complex was only observed in abundance at 32° C., at which temperature p53 was predominantly in a functional or "wild-type" form (Barak, Y. et al., *EMBO J.* 11:2115–2121 (1992) and Momand, J., et al., *Cell* 69:1237–1245 (1992)). By shifting the rat cell line down to 32° C. and blocking de novo protein synthesis it was shown that only "wild-type" p53 induced expression of the mdm2 gene, thereby accounting for the differential abundance of the complex in terms of p53 transcriptional activity (Barak, Y., et al., *EMBO J.* 12:461–468 (1993)). The explanation was further developed by the identification of a DNA binding site for wild-type p53 within the first intron of the mdm2 gene (Wu, X., et al., *Genes Dev.* 7:1126–1132 (1993)). Reporter constructs employing this p53 DNA binding site revealed that they were inactivated when wild-type p53 was co-expressed with MDM2.

This inhibition of the transcriptional activity of p53 may be caused by MDM2 blocking the activation domain of p53 and/or the DNA binding site. Consequently, it was proposed that mdm2 expression is autoregulated, via the inhibitory effect of MDM2 protein on the transcriptional activity of wild-type p53. This p53-mdm2 autoregulatory feedback loop provided a novel insight as to how cell growth might be regulated by p53. Up to a third of human sarcomas are considered to overcome p53-regulated growth control by amplification of the hdm2 gene (the human homologue of mdm2) (Oliner, J. D., et al., *Nature* 358:80–83 (1992)). Hence, the interaction between p53 and HDM2 represents a key potential therapeutic target. One mechanism by which MDM2 can promote tumorogenesis is by its inhibitory action on p53. The tumor suppressor functions of p53 control a pivotal checkpoint in the control of cell cycling (reviewed in Levine, A. J., *Cell* 88:323–331 (1997)). p53 is a transcription factor for a number of proteins that cause cell cycle arrest or cell death by apoptosis. The level and transcriptional activity of p53 are increased by damage to cellular DNA. The MDM2 protein inhibits p53 function by binding to an amphipathic N-terminal helix of p53, abrogating the interaction of p53 with other proteins and its transactivation activity. The interaction with MDM2 also targets p53 for ubiquitin dependent protein degradation. MDM2 exhibits p53 independent effects on cell cycling as well, possibly by direct interaction with some of the downstream effectors such as pRB and EF2 (Reviewed in Zhang, R. and Wang, H., Cur. Pharm. Des. 6:393–416 (2000)).

Blocking HDM2 from binding p53 would be therapeutically useful in restoring cell cycle control to cells that overexpress HDM2 as a front line cancer treatment. More generally, inhibition of HDM2 may increase the effectiveness of chemotherapy and radiation in p53 normal cancers by enhancing apoptosis and growth arrest signaling pathways.

A need continues to exist for potent, small molecules that inhibit the interactions between HDM2 and p53.

SUMMARY OF THE INVENTION

A first aspect of the present invention is directed to novel compounds of Formula I.

A second aspect of the present invention is directed to pharmaceutical compositions comprising at least one compound of Formula I, or a salt thereof, and one or more pharmaceutically acceptable excipients.

A third aspect of the present invention is directed to a method of inhibiting the binding of a protein encoded by hdm2 to p53 protein, comprising contacting p53 or one or more proteins encoded by mdm2, with one or more compounds of Formula I.

A fourth aspect of the invention is directed to a method of inducing apoptosis, comprising contacting an animal with a composition comprising a pharmaceutically effective amount of at least one compound of Formula I, or a salt thereof, and one or more pharmaceutically-acceptable excipients.

A fifth aspect of the present invention is directed to a method of treating cancer. The method comprises contacting an animal with (a) a pharmaceutically effective amount of an antineoplastic agent and (b) a pharmaceutically effective amount of at least one compound of Formula I, or a salt thereof, and one or more pharmaceutically-acceptable excipients.

A sixth aspect of the present invention is directed to a method of treating cancer, comprising contacting an animal with a composition comprising (a) a pharmaceutically effective amount of at least one compound of Formula I, or a salt thereof, (b) one or more agents that induce or cause DNA damage, and (c) one or more pharmaceutically-acceptable excipients.

A seventh aspect of the present invention is directed to a method of synthesizing compounds of Formula I.

DETAILED DESCRIPTION OF THE PREFERRED EMBODIMENTS

A novel class of small molecules that bind to HDM2 and/or MDM2 has now been discovered. By interfering with HDM2-p53 or MDM2-p53 interactions, these compounds increase the intracellular concentration of p53. These small molecules, therefore, have therapeutic utility in sensitizing tumor cells for chemotherapy. In tumor types particularly sensitive to an increase in functional p53, compounds of this type will be sufficient to induce apoptosis. Compounds of the present invention are also useful in treating tumor types in which HDM2 or MDM2 is overexpressed.

Compounds of the present invention include compounds of Formula I:

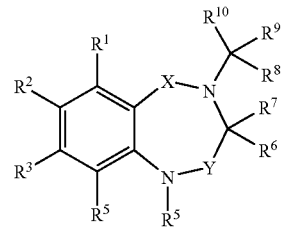

or a solvate, hydrate or pharmaceutically acceptable salt thereof; wherein:

X and Y are independently —C(O)—, —CH$_2$— or —C(S)—;

$R^1$, $R^2$, $R^3$, and $R^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or $R^1$ and $R^2$, or $R^2$ and $R^3$, or $R^3$ and $R^4$ are taken together to form —(CH$_2$)$_u$—, where u is 3–6, —CH═CH—CH═CH— or —CH$_2$CH═CHCH$_2$—;

$R^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

$R^6$ is cycloalkyl, aryl, heteroaryl, cycloalkylalkyl, aralkyl, heteroarylalkyl, or a saturated or partially unsaturated heterocycle, each of which is optionally substituted;

$R^7$ and $R^8$ are independently hydrogen or alkyl;

$R^9$ is cycloalkyl, aryl, heteroaryl, a saturated or partially unsaturated heterocycle, cycloalkyl(alkyl), aralkyl or heteroarylalkyl, each of which is optionally substituted; and $R^{10}$ is —(CH$_2$)$_n$—CO$_2$R$^b$, —(CH$_2$)$_m$—CO$_2$M, —(CH$_2$)$_i$—OH or —(CH$_2$)$_j$—CONR$^c$R$^d$ where $R^b$ is hydrogen, alkyl, optionally substituted cycloalkyl, or optionally substituted, saturated or partially unsaturated heterocycle;

M is a cation;

$R^c$ and $R^d$ are independently hydrogen, alkyl, hydroxyalkyl, carboxyalkyl, aminoalkyl, optionally substituted cycloalkyl, optionally substituted aryl, optionally substituted aralkyl, optionally substituted heteroaryl, optionally substituted heteroarylalkyl, and an optionally substituted, saturated or partially unsaturated heterocycle; and n is 0–8, m is 0–8, i is 1–8 and j is 0–8.

Preferred compounds include compounds of Formula I, or salts thereof, wherein:

$R^1$, $R^2$, $R^3$, and $R^4$ are independently hydrogen, halo, C$_{1-6}$ alkyl, C$_{2-6}$ alkenyl, C$_{2-6}$ alkynyl, C$_{3-7}$ cycloalkyl, optionally substituted C$_{6-10}$ aryl, optionally substituted C$_{6-10}$ ar(C$_{1-6}$)alkyl, optionally substituted heteroaryl, optionally substituted heteroar(C$_{1-6}$)alkyl, C$_{1-6}$ alkoxy, optionally substituted C$_{6-10}$ aryloxy, optionally substituted heteroaryloxy, cyano, amino, alkanoylamino, nitro, hydroxy, carboxy, or C$_{1-6}$ alkoxycarbonyl;

or $R^1$ and $R^2$, or $R^2$ and $R^3$, or $R^3$ and $R^4$ are taken together to form —CH=CH—CH=CH— or —CH$_2$CH=CHCH$_2$—;

$R^5$ is hydrogen, $C_{1-6}$ alkyl, $C_{3-7}$ cycloalkyl, optionally substituted $C_{6-10}$ aryl, optionally substituted heteroaryl, optionally substituted $C_{6-10}$ ar($C_{1-6}$)alkyl, optionally substituted heteroar($C_{1-6}$)alkyl, carboxy($C_{1-6}$)alkyl, $C_{1-6}$ alkoxycarbonyl, $C_{1-6}$ alkoxycarbonyl($C_{1-6}$)alkyl, aminocarbonyl, aminocarbonyl($C_{1-6}$)alkyl, or $C_{1-6}$ alkylaminocarbonyl($C_{1-6}$)alkyl;

$R^6$ is $C_{3-7}$ cycloalkyl, $C_{6-10}$ aryl, heteroaryl, a saturated or partially unsaturated heterocycle, $C_{3-7}$ cycloalkyl($C_{1-6}$)alkyl, $C_{6-10}$ ar($C_{1-6}$)alkyl or heteroaryl($C_{1-6}$)alkyl, each of which is optionally ring substituted by one or more substituents independently selected from the group consisting of $C_{1-4}$ alkyl, $C_{2-4}$ alkenyl, $C_{2-4}$ alkynyl, $C_{6-10}$ aryl, phenoxy, benzyloxy, 5–10 membered heteroaryl, hydroxy, $C_{1-4}$ alkoxy, $C_{1-4}$ alkylenedioxy, halo, $C_{1-4}$ haloalkyl, $C_{1-4}$ alkylthio, thio, amino, mono($C_{1-4}$)alkylamino, di($C_{1-4}$)alkylamino, and nitro;

$R^7$ is hydrogen or $C_{1-6}$ alkyl;

$R^8$ is hydrogen or $C_{1-6}$ alkyl;

$R^9$ is $C_{3-7}$ cycloalkyl, a saturated or partially unsaturated heterocycle, $C_{6-10}$ aryl, heteroaryl, $C_{3-7}$ cycloalkyl($C_{1-6}$)alkyl, $C_{6-10}$ ar($C_{1-6}$)alkyl or heteroaryl($C_{1-6}$)alkyl, each of which is optionally substituted by one or more substituents independently selected from the group consisting of $C_{1-4}$ alkyl, $C_{2-4}$ alkenyl, $C_{2-4}$ alkynyl, $C_{6-10}$ aryl, 5–10 membered heteroaryl, hydroxy, $C_{1-4}$ alkoxy, $C_{1-4}$ alkylenedioxy, carboxy, halo, $C_{1-4}$ haloalkyl, trifluoromethoxy, $C_{1-4}$ alkylthio, thio, amino, mono($C_{1-4}$)alkylamino, di($C_{1-4}$)alkylamino, and nitro; and $R^{10}$ is —(CH$_2$)$_n$—CO$_2$R$^b$, —(CH$_2$)$_m$—CO$_2$M, —(CH$_2$)$_i$—OH or —(CH$_2$)$_j$—CONR$^c$R$^d$, where
  $R^b$ is hydrogen, $C_{1-6}$ alkyl, optionally substituted $C_{3-7}$ cycloalkyl, or an optionally substituted, saturated or partially unsaturated heterocycle;
  M is a cation;
  $R^c$ and $R^d$ are independently hydrogen, $C_{1-6}$ alkyl, $C_{1-6}$ hydroxyalkyl, $C_{1-6}$ carboxyalkyl, aminoalkyl, optionally substituted $C_{3-7}$ cycloalkyl, optionally substituted $C_{6-10}$ aryl, optionally substituted $C_{6-10}$ ar($C_{1-6}$)alkyl, optionally substituted heteroaryl, optionally substituted heteroaryl($C_{1-6}$)alkyl, or an optionally substituted, saturated or partially unsaturated heterocycle; and
  n is 0–4, m is 0–4, i is 1–4 and j is 0–4.

In one preferred embodiment:

$R^1$ and $R^4$ are both hydrogen;

$R^2$ is hydrogen, halo, $C_{1-6}$ alkyl, $C_{1-6}$ hydroxyalkyl, $C_{2-6}$ alkenyl, $C_{2-6}$ alkynyl, $C_{3-7}$ cycloalkyl, acetylamino, cyano, amino, $C_{1-6}$ alkoxy, phenyl, thienyl, furanyl, and pyrrolyl, wherein said phenyl, thienyl and furanyl are optionally substituted by one or more substituents independently selected from the group consisting of halo, $C_{1-4}$ alkoxy, $C_{1-4}$ alkyl, amino, methylenedioxy, and ethylenedioxy;

$R^3$ is hydrogen, $C_{1-6}$ alkyl, phenyl, or halo; or $R^2$ and $R^3$ are taken together to form —CH=CH—CH=CH—;

$R^5$ is hydrogen; $C_{1-6}$ alkyl; $C_{1-6}$ hydroxyalkyl; carboxy($C_{1-6}$)alkyl; $C_{1-6}$ alkylcarbamoyl($C_{1-6}$)alkyl; $C_{1-6}$ alkoxycarbonylamino($C_{1-6}$)alkyl; $C_{3-7}$ cycloalkyl($C_{1-6}$)alkyl; $C_{6-10}$ aryl, optionally substituted by $C_{1-4}$ alkyl or halo; $C_{6-10}$ ar($C_{1-4}$)alkyl optionally substituted by $C_{1-4}$ alkyl or halo; and pyridyl($C_{1-4}$)alkyl;

$R^6$ is $C_{6-10}$ aryl, thienyl, benzothienyl, furanyl, benzofuranyl, indolyl, pyridyl, quinolinyl, $C_{3-7}$ cycloalkenyl or cubanyl, each of which is optionally substituted by one or more substituents independently selected from the group consisting of halo, $C_{1-4}$ alkyl, $C_{2-4}$ alkenyl, $C_{1-4}$ alkoxy, halo($C_{1-4}$)alkoxy, trifluoromethyl, trifluoromethoxy, $C_{1-4}$ alkylsulfanyl, trifluoromethylsulfanyl, cyano, thienyl, phenyl, halophenyl, trifluoromethylphenyl, phenoxy, benzyloxy and pyrrolidinyl;

$R^7$ is hydrogen or $C_{1-6}$ alkyl;

$R^8$ is hydrogen or $C_{1-6}$ alkyl;

$R^9$ is $C_{3-7}$ cycloalkyl, $C_{6-10}$ aryl, heteroaryl, $C_{3-7}$ cycloalkyl($C_{1-6}$)alkyl, $C_{6-10}$ ar($C_{1-6}$)alkyl or heteroaryl($C_{1-6}$)alkyl, each of which is optionally substituted on the ring portion; and $R^{10}$ is —(CH$_2$)$_n$—CO$_2$R$^b$ or —(CH$_2$)$_m$—CO$_2$M, where $R^b$ is hydrogen, $C_{1-6}$ alkyl, optionally substituted $C_{3-7}$ cycloalkyl, or optionally substituted heterocycloalkyl, M is a cation n and m are independently 0, 1, 2, 3 or 4; or $R^{10}$ is —(CH$_2$)$_i$—OH or —(CH$_2$)$_j$—CONR$^c$R$^d$, where
  $R^c$ and $R^d$ are independently hydrogen, hydroxy, $C_{3-7}$ cycloalkyl, $C_{1-6}$ alkyl, $C_{1-6}$ hydroxyalkyl, $C_{1-6}$ carboxyalkyl, $C_{1-6}$ aminoalkyl, optionally substituted phenyl, or optionally substituted benzyl; and
  i is 1, 2, 3, or 4, and j is 0, 1, 2, 3 or 4.

Preferred compounds include those wherein $R^1$ is hydrogen.

Preferred compounds include those wherein $R^4$ is hydrogen.

Useful values of $R^2$ include hydrogen, halo, $C_{1-4}$ alkyl, $C_{3-7}$ cycloalkyl, $C_{2-6}$ alkenyl, $C_{2-6}$ alkynyl, acetylamino, $C_{1-6}$ alkoxy, phenyl, halophenyl, hydroxyphenyl, $C_{1-6}$ alkoxyphenyl, $C_{1-6}$ alkylphenyl, aminophenyl, $C_{1-6}$ alkylenedioxyphenyl, hydroxycarbonylphenyl, thienyl, $C_{1-6}$ alkylthienyl, furanyl, pyrrolyl, amino, $C_{1-6}$ hydroxyalkyl and cyano.

Useful values of $R^2$ also include hydrogen, iodo, fluoro, chloro, bromo, methyl, ethyl, propyl, isopropyl, t-butyl, sec-butyl, cyclopropyl, ethynyl, acetylamino, methoxy, phenyl, 3-chlorophenyl, 4-chlorophenyl, 4-hydroxyphenyl, 3-methoxyphenyl, 4-methylphenyl, 3-methylphenyl, 3-isopropylphenyl, 3-aminophenyl, 3,4-methylenedioxyphenyl, 4-hydroxycarbonylphenyl, thien-3-yl, 4-methylthien-2-yl, furan-2-yl, 1H-pyrrol-3-yl, amino, 2-hydroxyethyl, hydroxymethyl, furan-3-yl, vinyl and cyano.

Preferred compounds include those wherein $R^2$ is halo or phenyl. More preferred compounds include those wherein $R^2$ is iodo.

Useful values of $R^3$ include hydrogen, phenyl, fluoro, chloro, iodo and methyl. Preferred compounds are those wherein $R^3$ is hydrogen.

Useful values of $R^5$ include hydrogen, $C_{1-6}$ alkyl, $C_{1-6}$ hydroxyalkyl, carboxy($C_{1-6}$)alkyl, $C_{1-6}$ alkylphenyl, $C_{1-6}$ alkylbenzyl, phenethyl, phenyl($C_{1-6}$)alkyl, naphthyl($C_{1-6}$)alkyl, $C_{3-7}$ cycloalkyl($C_{1-6}$)alkyl, pyridyl($C_{1-6}$)alkyl, $C_{1-6}$ alkoxycarbonylamino($C_{1-6}$)alkyl, and $C_{1-6}$ alkylcarbamoyl($C_{1-6}$)alkyl.

Useful values of $R^5$ also include hydrogen, methyl, carboxymethyl, 3-methylbutyl, 2-methylpropyl, isopropyl, 2-methylphenyl, 3-methylphenyl, 4-methylphenyl, phenyl, benzyl, phenethyl, 3-phenylpropyl, naphthalen-2-ylmethyl, cyclohexylmethyl, cyclopentylmethyl, cyclobutylmethyl, pyrid-2-ylmethyl, pyrid-3-ylmethyl, pyrid-4-ylmethyl, 2-methylbenzyl, 3-methylbenzyl, 4-methylbenzyl, 2-carboxyethyl, 2-t-butoxycarbonylaminoethyl, 2-pyrid-2-ylethyl, methylcarbamoylmethyl and 2,3-dihydroxypropyl.

Preferred compounds include those wherein $R^5$ is hydrogen.

Useful values of $R^6$ include optionally substituted $C_{6-10}$ aryl.

Useful values of $R^6$ also include trifluoromethylphenyl, halophenyl, $C_{1-6}$ alkylphenyl, $C_{1-6}$ alkoxyphenyl, halo($C_{1-4}$)

alkoxyphenyl, naphthyl, benzyloxyphenyl, phenoxyphenyl, dihydrobenzodioxinyl, trifluoromethylhalophenyl, pyridyl, thienyl, $C_{1-6}$ alkylthienyl, halothienyl, bithienyl, $C_{1-6}$ alkylbenzothienyl, (halophenyl)furanyl, quinolinyl, biphenyl, indolyl, (trifluoromethylsulfanyl)phenyl, (trifluoromethylphenyl)furanyl, halo($C_{1-4}$)alkoxyphenyl, benzofuranyl, cyanophenyl, halopyridyl, (methylsulfanyl)phenyl, pyrrolidinylphenyl, $C_{2-6}$ alkenyl($C_{3-7}$)cycloalkenyl, cubanyl and halocubanyl.

Useful values of $R^6$ also include 2-trifluoromethylphenyl, 3-trifluoromethylphenyl, 4-trifluoromethylphenyl, 2-chlorophenyl, 3-chlorophenyl, 4-chlorophenyl, 2-bromophenyl, 3-bromophenyl, 4-bromophenyl, 4-iodophenyl, 4-methylphenyl, 4-ethylphenyl, 4-trifluoromethoxyphenyl, 4-isopropylphenyl, phenyl, 4-methoxy-phenyl, naphthalen-2-yl, 4-tert-butylphenyl, 4-benzyloxyphenyl, 4-phenoxyphenyl, 3,4-dichlorophenyl, 3,4-dimethoxyphenyl, 2,3-dihydrobenzo[1,4]dioxin-6-yl, 4-bromo-2-fluorophenyl, 2-fluoro-4-trifluoromethylphenyl, 3-fluoro-4-trifluoromethylphenyl, 4-chloro-3-trifluoromethylphenyl, 4-chloro-3-fluorophenyl, pyrid-2-yl, pyrid-3-yl, pyrid-4-yl, thien-3-yl, 5-methylthien-2-yl, 3-methylthien-2-yl, 4-bromothien-2-yl, 5-[2,2']bithienyl, 3-methylbenzo[b]thiophen-2-yl, 5-(2-chlorophenyl)-furan-2-yl, 5-(3-chlorophenyl)-furan-2-yl, quinolin-3-yl, biphen-4-yl, indol-2-yl, indol-3-yl, 4-trifluoromethylsulfanylphenyl, 5-(3-trifluoromethylphenyl)furan-2-yl, 4-(1,1,2,2-tetrafluoroethoxy)phenyl, 4-difluoromethoxyphenyl, benzofuran-2-yl, 4-cyanophenyl, 6-chloropyrid-3-yl, 4-methylsulfanylphenyl, 4-pyrrolidin-1-ylphenyl, 5-chlorothien-2-yl, 4-isopropenylcyclohex-1-enyl and 1-chlorocuban-4-yl.

Preferred compounds include those wherein $R^6$ is 4-chlorophenyl, 4-bromophenyl, 4-trifluoromethylphenyl or 4-trifluoromethoxyphenyl. More preferred compounds include those wherein $R^6$ is 4-chlorophenyl.

Useful values of $R^7$ include hydrogen and methyl. Preferred compounds include those wherein $R^7$ is hydrogen.

Useful values of $R^8$ include hydrogen and methyl. Preferred compounds include those wherein $R^8$ is hydrogen.

Useful values of $R^9$ include optionally substituted $C_{6-10}$ aryl and optionally substituted $C_{6-10}$ ar($C_{1-6}$)alkyl.

Useful values of $R^9$ also include phenyl, 4-chlorophenyl, 4-chlorobenzyl, benzyl, cyclohexyl, cyclohexylmethyl, 4-hydroxymethyl, pyridylmethyl, 4-fluorophenyl, 4-trifluoromethylphenyl, 4-iodobenzyl, 4-bromobenzyl, thien-2-yl, thien-2-ylmethyl, naphth-2-ylmethyl, pyrid-2-ylethyl, 3-methylphenyl, 4-methylphenyl, 4-ethylphenyl, 4-chloro-3-fluorophenyl, 2-fluoro-4-trifluoromethylphenyl, 4-hydroxycarbonylphenyl, naphthalen-2-yl, naphthalen-1-yl, 4-iodophenyl, 4-bromophenyl, 3,4-dichlorophenyl, 2-chlorophenyl, 4-tert-butylphenyl, 4-isopropylphenyl, 3-chlorophenyl, 4-trifluoromethoxyphenyl, and 3-hydroxyphenyl, 4-hydroxybenzyl, 4-trifluoromethylbenzyl, naphth-1-ylmethyl, 6-chloropyrid-3-yl and 6-methylpyrid-3-yl.

Preferred compounds include those wherein $R^9$ is halophenyl or halobenzyl. More preferred compounds include those wherein $R^9$ is phenyl or 4-chlorophenyl.

Useful values of $R^{10}$ include —COOR$^b$ and —CH$_2$—COOR$^b$, where $R^b$ is hydrogen or $C_{1-6}$ alkyl; and —COOM and —CH$_2$—COOM, where M is Na$^+$ or K$^+$.

Preferred compounds include those wherein $R^{10}$ is —COOR$^b$ or —CH$_2$—COOR$^b$, where $R^b$ is hydrogen, methyl, ethyl, propyl or tert-butyl.

Preferred compounds also include those wherein $R^{10}$ is —COOH or —COOM, where M is Na$^{30}$ or K$^+$.

Useful values of $R^{10}$ also include —CH$_2$OH and —CH$_2$CH$_2$OH; and —CH$_2$—CONR$^c$R$^d$ and —CONR$^c$R$^d$, where $R^c$ and $R^d$ are independently hydrogen, methyl, ethyl, propyl, t-butyl, hydroxymethyl, hydroxyethyl, hydroxypropyl, aminomethyl, aminoethyl, aminopropyl, carboxymethyl, carboxyethyl, carboxypropyl, cyclopentyl, cyclohexyl, phenyl or benzyl.

Preferred compounds include those wherein $R^{10}$ is —CH$^2$—CONR$^c$R$^d$ or —CONR$^c$R$^d$, where $R^c$ and $R^d$ are independently hydrogen, methyl, hydroxyethyl, 3-carboxypropyl, 1-carboxy-2-methylpropyl, hydroxy, 4-carboxybutyl, 5-carboxypentyl, 2-(methoxycarbonyl)ethyl or 2-(hydroxyguanidino)ethyl.

In each of the above embodiments, X and Y are independently —C(O)—, —CH$_2$— or —C(S)—, more preferably —C(O)— or —C(S)—, most preferably —C(O)—.

A second aspect of the present invention is directed to pharmaceutical compositions comprising a) at least one compound of Formula I or a pharmaceutically acceptable salt thereof; and b) one or more pharmaceutically-acceptable excipients.

Preferably, the pharmaceutical composition is sterile.

A third aspect of the present invention is directed to a method of inhibiting the binding of a protein encoded by mdm2 to p53 protein, comprising contacting p53 or one or more proteins encoded by mdm2 with one or more compounds of Formula I, wherein $R^1$–$R^{10}$ are defined as above.

A fourth aspect of the invention is directed to a method of inducing apoptosis, comprising contacting an animal with a composition comprising a pharmaceutically effective amount of at least one compound of Formula I, or a salt thereof, wherein $R^1$–$R^{10}$ are defined as above, and optionally one or more pharmaceutically-acceptable excipients.

A fifth aspect of the present invention is directed to a method of treating cancer, comprising contacting an animal with (a) a pharmaceutically effective amount of an antineoplastic agent, and (b) a pharmaceutically effective amount of at least one compound of Formula I, or a salt thereof, wherein $R^1$–$R^{10}$, are defined as above, and optionally one or more pharmaceutically-acceptable excipients, in combination with (a), (b), or (a) and (b).

A sixth aspect of the present invention is directed to a method of treating cancer, comprising contacting an animal with a composition comprising (a) a pharmaceutically effective amount of at least one compound of Formula I, or a salt thereof, (b) one or more agents that induce or cause DNA damage, and optionally (c) one or more pharmaceutically-acceptable excipients.

A seventh aspect of the present invention is directed to a method of making compounds of Formula I.

Compounds within the scope of the invention are described in the Examples. Examples of preferred compounds include:

(4-chloro-phenyl)-[3-(4-chloro-phenyl)-7-iodo-2,5-dioxo-1,2,3,5-tetrahydro-benzo[e][1,4]diazepin-4-yl]-acetic acid;

2-[7-bromo-3-(4-chloro-phenyl)-2,5-dioxo-1,2,3,5-tetrahydro-benzo[e][1,4]diazepin-4-yl]-3-(4-chloro-phenyl)-propionic acid;

2-(4-chloro-phenyl)-2-[3-(4-chloro-phenyl)-7-iodo-2,5-dioxo-1,2,3,5-tetrahydro-benzo[e][1,4]diazepin-4-yl]-acetamide;

[7-chloro-3-(4-chloro-phenyl)-2,5-dioxo-1,2,3,5-tetrahydro-benzo[e][1,4]diazepin-4-yl]-(4-chloro-phenyl)-acetic acid;

(4-chloro-phenyl)-[3-(4-chloro-phenyl)-7-ethynyl-2,5-dioxo-1,2,3,5-tetrahydro-benzo[e][1,4]diazepin-4-yl]-acetic acid;

[3-(4-chloro-phenyl)-7-iodo-2,5-dioxo-1,2,3,5-tetrahydro-benzo[e][1,4]diazepin-4-yl]-p-tolyl-acetic acid;

(4-chloro-3-fluoro-phenyl)-[3-(4-chloro-phenyl)-7-iodo-2,5-dioxo-1,2,3,5-tetrahydro-benzo[e][1,4]diazepin-4-yl]-acetic acid;

(4-chloro-phenyl)-[3-(4-chloro-phenyl)-7-ethyl-2,5-dioxo-1,2,3,5-tetrahydro-benzo[e][1,4]diazepin-4-yl]-acetic acid;

(4-chloro-phenyl)-[3-(4-chloro-phenyl)-7-isopropyl-2,5-dioxo-1,2,3,5-tetrahydro-benzo[e][1,4]diazepin-4-yl]-acetic acid;

(4-bromo-phenyl)-[3-(4-chloro-phenyl)-7-isopropyl-2,5-dioxo-1,2,3,5-tetrahydro-benzo[e][1,4]diazepin-4-yl]-acetic acid;

[3-(4-chloro-3-fluoro-phenyl)-7-iodo-2,5-dioxo-1,2,3,5-tetrahydro-benzo[e][1,4]diazepin-4-yl]-(4-chloro-phenyl)-acetic acid;

[3-(4-chlorophenyl)-7-phenyl-2,5-dioxo-1,2,3,5-tetrahydro-benzo[e][1,4]diazepin-4-yl]-phenylacetic acid;

[3-(4-chloro-phenyl)-7-iodo-2,5-dioxo-1,2,3,5-tetrahydro-benzo[e][1,4]diazepin-4-yl]-(4-fluoro-phenyl)-acetic acid;

[3-(4-chloro-phenyl)-7-iodo-2,5-dioxo-1,2,3,5-tetrahydro-benzo[e][1,4]diazepin-4-yl]-(4-trifluoromethyl-phenyl)-acetic acid;

(4-chloro-phenyl)-[7-iodo-2,5-dioxo-3-(4-trifluoromethoxy-phenyl)-1,2,3,5-tetrahydrobenzo[e][1,4]diazepin-4-yl]-acetic acid;

(4-chloro-phenyl)-[7-iodo-2,5-dioxo-3-(4-trifluoromethyl-phenyl)-1,2,3,5-tetrahydrobenzo[e][1,4]diazepin-4-yl]-acetic acid;

[3-(4-bromo-phenyl)-7-iodo-2,5-dioxo-1,2,3,5-tetrahydro-benzo[e][1,4]diazepin-4-yl]-(4-chloro-phenyl)-acetic acid;

[3-(4-chloro-phenyl)-7-iodo-2,5-dioxo-1,2,3,5-tetrahydro-benzo[e][1,4]diazepin-4-yl]-(4-isopropyl-phenyl)-acetic acid;

(4-chloro-phenyl)-[3-(4-chloro-phenyl)-7-cyano-2,5-dioxo-1,2,3,5-tetrahydro-benzo[e][1,4]diazepin-4-yl]-acetic acid;

3-(4-chloro-phenyl)-4-(3-hydroxy-1-phenyl-propyl)-7-iodo-3,4-dihydro-1H-benzo[e][1,4]diazepine-2,5-dione;

2-(4-chloro-phenyl)-2-[3-(4-chloro-phenyl)-7-iodo-2,5-dioxo-1,2,3,5-tetrahydro-benzo[e][1,4]diazepin-4-yl]-N-hydroxy-acetamide;

[7-bromo-3-(4-chloro-phenyl)-2,5-dioxo-1,2,3,5-tetrahydro-benzo[e][1,4]diazepin-4-yl]-(4-chloro-phenyl)-acetic acid;

[8-chloro-3-(4-chloro-phenyl)-7-iodo-2,5-dioxo-1,2,3,5-tetrahydro-benzo[e][1,4]diazepin-4-yl]-(4-chloro-phenyl)-acetic acid;

5-{2-(4-chloro-phenyl)-2-[3-(4-chloro-phenyl)-7-iodo-2,5-dioxo-1,2,3,5-tetrahydro-benzo[e][1,4]diazepin-4-yl]-acetylamino}-pentanoic acid;

3-{2-(4-chloro-phenyl)-2-[3-(4-chloro-phenyl)-7-iodo-2,5-dioxo-1,2,3,5-tetrahydro-benzo[e][1,4]diazepin-4-yl]-acetylamino}-propionic acid;

5-[4-[carboxy-(4-chloro-phenyl)-methyl]-3-(4-chlorophenyl)-7-iodo-2,5-dioxo-2,3,4,5-tetrahydro-benzo[e][1,4]diazepin-1-yl]-pentanoic acid;

and pharmaceutically acceptable salts thereof.

Additional examples of preferred compounds include:

(4-chlorophenyl)-[3-(4-chlorophenyl)-7-iodo-5-oxo-1,2,3,5-tetrahydro-benzo[e][1,4]diazepin-4-yl]acetic acid;

3-(4-chloro-phenyl)-3-[3-(4-chloro-phenyl)-7-iodo-5-oxo-1,2,3,5-tetrahydro-benzo[e][1,4]diazepin-4-yl]-propionic acid;

(4-chloro-phenyl)-[3-(4-chloro-phenyl)-7-iodo-5-oxo-2-thioxo-1,2,3,5-tetrahydro-benzo[e][1,4]diaze pin-4-yl]-acetic acid;

3-(4-chloro-phenyl)-4-[1-(4-chloro-phenyl)-2-hydroxy-ethyl]-7-iodo-1,3,4,5-tetrahydro-benzo[e][1,4]diazepin-2-one;

3-(4-chloro-phenyl)-4-[1-(4-chloro-phenyl)-2-hydroxy-ethyl]-7-iodo-1,2,3,4-tetrahydro-benzo[e][1,4]diazepin-5-one;

and pharmaceutically-acceptable salts thereof.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabeled compound of the invention, administering it parenterally in a detectable dose to an animal such as rat, mouse, guinea pig, monkey, or to man, allowing sufficient time for metabolism to occur and isolating its conversion products from the urine, blood or other biological samples.

Some of the compounds disclosed herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached, or a sulfur atom to which three different groups are attached, where the sulfur atom and its attached groups form a sulfoxide, sulfinic ester, sulfonium salt or sulfite.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as "prodrugs." The expression "prodrug" denotes a derivative of a known direct acting drug, which derivative has enhanced delivery characteristics and therapeutic value as compared to the drug, and is transformed into the active drug by an enzymatic or chemical process. Prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Useful prodrugs are those where $R^b$ is alkyl, alkenyl, alkynyl, or arylalkyl.

When any variable occurs more than one time in any constituent or in Formula I, its definition on each occurrence is independent of its definition at every other occurrence. Also, combinations of substituents and/or variables are permissible only if such combinations result in stable compounds.

DEFINITIONS

The term "alkyl" as employed herein by itself or as part of another group refers to both straight and branched chain radicals of up to 10 carbons, unless the chain length is otherwise limited, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, or decyl.

The term "alkenyl" is used herein to mean a straight or branched chain radical of 2–10 carbon atoms, unless the chain length is otherwise limited, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like. Preferably, the alkenyl chain is 2 to 8 carbon atoms in length, most preferably from 2 to 4 carbon atoms in length.

The term "alkynyl" is used herein to mean a straight or branched chain radical of 2–10 carbon atoms, unless the chain length is otherwise limited, wherein there is at least one triple bond between two of the carbon atoms in the chain, including, but not limited to, ethynyl, 1-propynyl, 2-propynyl, and the like. Preferably, the alkynyl chain is 2 to 8 carbon atoms in length, most preferably from 2 to 4 carbon atoms in length.

In all instances herein where there is an alkenyl or alkynyl moiety as a substituent group, the unsaturated linkage, i.e., the vinyl or ethenyl linkage, is preferably not directly attached to a nitrogen, oxygen or sulfur moiety.

The term "alkoxy" or "alkyloxy" refers to any of the above alkyl groups linked to an oxygen atom. Typical examples are methoxy, ethoxy, isopropyloxy, sec-butyloxy, and t-butyloxy.

The term "aryl" as employed herein by itself or as part of another group refers to monocyclic or bicyclic aromatic groups containing from 6 to 12 carbons in the ring portion, preferably 6–10 carbons in the ring portion. Typical examples include phenyl, biphenyl, naphthyl or tetrahydronaphthyl.

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "heteroaryl" as employed herein refers to groups having 5 to 14 ring atoms; 6, 10 or 14 pi electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

The phrase "saturated or partially unsaturated heterocycle" as employed herein, by itself or as part of another group, refers to a saturated or partially unsaturated ring system having 5 to 14 ring atoms selected from carbon atoms and 1, 2, 3, or 4 oxygen, nitrogen, or sulfur heteroatoms. Typical saturated examples include pyrrolidinyl, imidazolidinyl, pyrazolidinyl, tetrahydrofuranyl, tetrahydropyranyl, piperidyl, piperazinyl, quinuclidinyl, morpholinyl, and dioxacyclohexyl. Typical partially unsaturated examples include pyrrolinyl, imidazolinyl, pyrazolinyl, dihydropyridinyl, tetrahydropyridinyl, and dihydropyranyl. Either of these systems can be optionally fused to a benzene ring.

The terms "heteroarylalkyl" or "heteroaralkyl" as employed herein both refer to a heteroaryl group attached to an alkyl group. Typical examples include 2-(3-pyridyl)ethyl, 3-(2-furyl)-n-propyl, 3-(3-thienyl)-n-propyl, and 4-(1-isoquinolinyl)-n-butyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "cycloalkylalkyl" or "cycloalkyl(alkyl)" as employed herein, by itself or as part of another group, refers to a cycloalkyl group attached to an alkyl group. Typical examples are 2-cyclopentylethyl, cyclohexylmethyl, cyclopentylmethyl, 3-cyclohexyl-n-propyl, and 5-cyclobutyl-n-pentyl.

The term "cycloalkenyl" as employed herein, by itself or as part of another group, refers to cycloalkenyl groups containing 3 to 9 carbon atoms and 1 to 3 carbon-carbon double bonds. Typical examples include cyclopropenyl, cyclobutenyl, cyclopentenyl, cyclohexenyl, cyclohexadienyl, cycloheptenyl, cycloheptadienyl, cyclooctenyl, cyclooctadienyl, cyclooctatrienyl, cyclononenyl, and cyclononadienyl.

The term "halogen" or "halo" as employed herein by itself or as part of another group refers to chlorine, bromine, fluorine or iodine.

The term "monoalkylamine" or "monoalkylamino" as employed herein by itself or as part of another group refers to the group $NH_2$ wherein one hydrogen has been replaced by an alkyl group, as defined above.

The term "dialkylamine" or "dialkylamino" as employed herein by itself or as part of another group refers to the group $NH_2$ wherein both hydrogens have been replaced by alkyl groups, as defined above.

The term "hydroxyalkyl" as employed herein refers to any of the above alkyl groups wherein one or more hydrogens thereof are substituted by one or more hydroxyl moieties.

The term "haloalkyl" as employed herein refers to any of the above alkyl groups wherein one or more hydrogens thereof are substituted by one or more halo moieties. Typical examples include fluoromethyl, difluoromethyl, trifluoromethyl, trichloroethyl, trifluoroethyl, fluoropropyl, and bromobutyl.

The term "carboxyalkyl" as employed herein refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound form a saturated or unsaturated 5-, 6-, or 7-membered ring.

The phrase "optionally substituted" when not explicitly defined refers to a group or groups being optionally substituted with one or more substituents independently selected from the group consisting of hydroxy, nitro, trifluoromethyl, halogen, $C_{1-6}$ alkyl, $C_{1-6}$ haloalkyl, $C_{1-6}$ alkoxy, $C_{1-6}$ alkylenedioxy, $C_{1-6}$ aminoalkyl, $C_{1-6}$ hydroxyalkyl, $C_{2-4}$ alkenyl, $C_{2-4}$ alkynyl, $C_{6-10}$ aryl, phenoxy, benzyloxy, 5–10 membered heteroaryl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, $C_{2-6}$ alkoxycarbonylalkyl, carboxy, $C_{2-6}$ hydroxyalkoxy, ($C_{1-6}$) alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl)amino, bis($C_{2-10}$ carboxyalkyl)amino, $C_{2-6}$ carboxyalkoxy, $C_{2-6}$ carboxyalkyl, carboxyalkylamino, guanidinoalkyl, hydroxyguanidinoalkyl, cyano, trifluoromethoxy, or perfluoroethoxy.

Preferred optional substituents include one or more substituents independently selected from the group consisting of nitro, hydroxy, carboxy, $C_{1-4}$ alkoxy, $C_{1-4}$ alkyl, halo, $C_{1-4}$ haloalkyl, $C_{1-4}$ alkylthio, thio, amino, mono($C_{1-4}$)alkylamino, and di($C_{1-4}$)alkylamino.

"mdm2" is used herein to mean the murine double minute 2 gene, and homologous genes found in other animals.

"MDM2" is used herein to mean a protein obtained as a, result of expression of the mdm2 oncogene. Within the meaning of this term, it will be understood that MDM2 encompasses all proteins encoded by mdm2, mutants thereof, alternative splice proteins thereof, and phosphorylated proteins thereof. Additionally, as used herein, it will be understood that the term "MDM2" includes MDM2 homologues of other animals (e.g., HDM2).

"hdm2" is used herein to mean the human gene which is homologous to the mouse mdm2.

"HDM2" is used herein to mean a protein obtained as a result of expression of the hdm2 oncogene. Within the meaning of this term, it will be understood that HDM2 encompasses all proteins encoded by hdm2, mutants thereof, alternative splice proteins thereof, and phosphorylated proteins thereof.

The phrase "antineoplastic agent" is used herein to mean any agent that is used to treat or prevent cancer or other conditions comprising uncontrolled proliferation and growth of cells. Antineoplastic agents include anticancer agents.

The phrase "contacting one or more proteins" is used herein to mean placing a compound of the present invention in a solution with one or more proteins of interest. A compound of Formula I and one or more proteins of interest may be in solution together in an aqueous solution, non-aqueous solution, or combination of an aqueous solution and non-aqueous solution. Other proteins may be present in solution along with the compound of Formula I and the protein of interest. Other inorganic or organic molecules may be present in the solution. Such inorganic and organic molecules include, but are not limited to, NaCl, HEPES, and octyl glucoside. The solution may be within an animal cell or outside of an animal cell.

The phrase "inhibiting the binding" is used herein to mean preventing or reducing the direct or indirect association of one or more molecules, peptides, proteins, enzymes, or receptors; or preventing or reducing the normal activity of one or more molecules, peptides, proteins, enzymes, or receptors.

The phrase "inducing apoptosis" is used herein to mean causing directly or indirectly a cell of animal origin to undergo apoptosis, a process of controlled, or programmed, cellular death.

The phrase "HDM2 inhibitor" is used herein to describe an agent which inhibits the function of HDM2 in the assay described in Example 217.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, palmoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; and aralkyl halides like benzyl and phenethyl bromides and others. Preferred acids for forming acid addition salts include HCl, acetic acid, trifluoroacetic acid and fumaric acid.

Compositions and Methods of Use

Compositions of the present invention include pharmaceutical compositions comprising a compound of Formula I, wherein $R^1$–$R^{10}$ are defined above, and one or more pharmaceutically acceptable excipients. Preferred compositions of the present invention are pharmaceutical compositions comprising a compound selected from a preferred group of compounds of Formula I as defined above, and one or more pharmaceutically acceptable excipients.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragée cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropyl methylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragée cores are provided with suitable coatings that, if desired, are resistant to gastric juices. For this purpose, concentrated saccharide solutions can be used, which can contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragée coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition are preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferred to use the solid anionic surface-active agent in the form of a sodium salt.

A further form of topical administration is to the eye. The compounds and compositions of the present invention are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 (1976)).

Compounds of the present invention may be used alone or in combination with one or more additional antineoplastic agents. When a compound of the present invention is used along with one or more additional antineoplastic agents, the compound of the present invention may be formulated with the other antineoplastic agent or agents so that a pharmaceutical composition comprising a compound of Formula I and one or more additional antineoplastic agents is administered to an animal. Alternatively, the compound of Formula I can be administered as a separate pharmaceutical composition from the composition comprising the one or more additional antineoplastic agents. Antineoplastic agents that may be used in combination with the compounds of the present invention include compounds selected from the following compounds and classes of antineoplastic agents:

1. fluoropyrimidines, such as 5-FU (5-fluorouracil), Fluorodeoxyuridine, Ftorafur, 5'-deoxyfluorouridine, UFT, and S-1 Capecitabine;
2. pyrimidine nucleosides, such as Deoxycytidine, Cytosine Arabinoside, Cytarabine, Azacitidine, 5-Azacytosine, Gencitabine, and 5-Azacytosine-Arabinoside;
3. purines, such as 6-Mercaptopurine, Thioguanine, Azathioprine, Allopurinol, Cladribine, Fludarabine, Pentostatin, and 2-Chloroadenosine;
4. platinum analogues, such as Cisplatin, Carboplatin, Oxaliplatin, Tetraplatin, Platinum-DACH, Ormaplatin, and CI-973, JM-216;
5. anthracyclines/anthracenediones, such as Doxorubicin, Daunorubicin, Epirubicin, Idarubicin, and Mitoxantrone;
6. epipodophyllotoxins, such as Etoposide, and Teniposide;
7. camptothecins, such as Irinotecan, Topotecan, 9-Amino Camptothecin, 10,11-Methylenedioxy Camptothecin, 9-Nitro Camptothecin, and TAS 103;
8. hormones and hormonal analogues, such as diethylstilbestrol, Tamoxifen, Toremefine, Tolmudex, Thymitaq, flutamide, fluoxymesterone, bicalutamide, Finasteride, estradiol, Trioxifene, dexamethasone, leuproelin acetate, estramustine, Droloxifene, medroxyprogesterone, megesterol acetate, aminoglutethimide, testolactone, testosterone, diethylstilbestrol, and hydroxyprogesterone;
9. enzymes, proteins and antibodies, such as Asparaginase, Interleukins, Interferons, Leuprolide, and Pegaspargase;
10. vinca alkaloids, such as Vincristine, Vinblastine, Vinorelbine, and Vindesine;
11. taxanes, such as Paclitaxel, Taxotere and Docetaxel.

Antineoplastic agents that may be used in combination with compounds of the invention also include compounds selected from the following Mechanism-Based Classes:

1. Antihormonals—See classification for Hormones and Hormonal Analogs above, Anastrozole, Goserelin, and Aminoglutethimide;
2. Antifolates, such as methotrexate, leucovorin, aminopterin, trimetrexate, Trimethoprim, pyritrexim, pyrimethamine, Edatrexate, and MDAM;
3. Antimicrotubule Agents, such as Taxanes, Vinca Alkaloids, and Vinorelbine;
4. Alkylating Agents (Classical and Non-Classical), such as Nitrogen Mustards (Mechlorethamine, Chlorambucil, Melphalan, Uracil Mustard), Oxazaphosphorines (Ifosfamide, Cyclophosphamide, Perfosfamide, Trophosphamide), Alkylsulfonates (Busulfan), Nitrosoureas (Carmustine, Lomustine, Streptozocin), Thiotepa, and Dacarbazine;
5. Antimetabolites, such as Purines, pyrimidines and nucleoside analogs, listed above;
6. Antibiotics, such as Anthracyclines/Anthracenediones, Bleomycin, Dactinomycin, Mitomycin, Plicamycin, Pentostatin, and Streptozocin;
7. Topoisomerase Inhibitors, such as Camptothecins (Topo I), Epipodophyllotoxins, AMSA, VP-16 and Ellipticines (Topo II);
8. Antivirals, such as AZT, acyclovir, penciclovir, famcyclovir, didehydrodideoxythymidine, dideoxycytidine, -SddC, ganciclovir, dideoxyinosine, and viral-specific protease inhibitors;
9. Miscellaneous Cytotoxic Agents, such as Hydroxyurea, Mitotane, Fusion Toxins, PZA, Bryostatin, Retinoids, Butyric Acid and derivatives, Pentosan, Fumagillin, Mitoxantrone, Bone Marrow Growth Factors, and Procarbazine.

Compounds of the present invention are useful for the treatment of uncontrolled proliferation of cells and/or cancer. The compounds of the present invention may produce beneficial cytostatic and/or cytotoxic effects. The cytostatic effects include the inhibition of further cell growth and/or cell division. The cytotoxic effects include the induction of cell death by mechanisms that include apoptosis and cellular necrosis. Specifically, the compounds of the present invention are useful in treating the following cancers: breast cancer, ovarian cancer, cervical carcinoma, endometrial carcinoma, choriocarcinoma, soft tissue sarcomas, osteosarcomas, rhabdomyosarcomas, leiomyomas, leiomyosarcomas, head and neck cancers, lung and bronchogenic carcinomas, brain tumors, neuroblastomas, esophogeal cancer, colorectal adenocarcinomas, bladder cancer, urothelial cancers, leukemia, lymphoma, malignant melanomas, oral squamous carcinoma, hepatoblastoma, glioblastoma, astrocytoma, medulloblastoma, Ewing's sarcoma, lipoma, liposarcoma, malignant fibroblast histoma, malignant Schwannoma, testicular cancers, thyroid cancers, Wilms' tumor, pancreatic cancers, colorectal adenocarcinoma, tongue carcinoma, gastric carcinoma, and nasopharyngeal cancers. Preferably, the present invention is used to treat the cancers selected from the group consisting of breast cancer, choriocarcinoma, soft tissue sarcomas, osteosarcomas, rhabdomyosarcomas, lipoma and liposarcoma. The cancers and diseases listed above are merely meant to be illustrative and are by no means meant to be a limiting or exhaustive list.

Additionally, the compounds and compositions described herein are useful to treat any undesired or detrimental condition that results from the HDM2 protein or the MDM2 protein inhibiting the function of p53 or other cellular proteins that induce apoptosis, induce cellular death, or regulate the cellular cycle.

The compounds of the present invention are also useful at inhibiting the interaction between p53 and HDMX and/or MDMX. MDMX, also known as MDM4, is a cellular protein involved in the regulation of the cell cycle. For example, see Riemenschneider et al., Cancer Res. 59(24): 6091–6 (1999).

The compounds of the present invention are also useful for the treatment and prevention of inflammatory conditions. The compounds of the present invention can be administered as anti-inflammatory agents that reduce the degree of or eliminate inflammation of tissues.

The compounds of the present invention are also useful for the treatment of autoimmune diseases and conditions. The compounds of the present invention can be administered to reduce or eliminate the symptoms of an autoimmune disease. Autoimmune diseases include any disease in which an animal's immune system reacts adversely to a self-antigen. A self-antigen is any antigen that is normally found in the animal's body. Representative autoimmune diseases include Hashimoto's thyroiditis, Grave's disease, multiple sclerosis, pernicious anemia, Addison's disease, insulin-dependent diabetes mellitus, rheumatoid arthritis, systemic lupus erythematosus (SLE or lupus), dermatomyositis, Crohn's disease, Wegener's granulomatosis, Anti-Glomerular Basement Membrane Disease, Antiphospholipid Syndrome, Dermatitis Herpetiformis, Allergic Encephalomyelitis, Glomerulonephritis, Membranous Glomerulonephritis, Goodpasture Syndrome, Lambert-Eaton, Myasthenic Syndrome, Myasthenia Gravis, Bullous Pemphigoid, Polyendocrinopathies, Reiter's Disease, and Stiff-Man Syndrome. Preferably, the present invention is used to treat rheumatoid arthritis or systemic lupus erythematosus.

Inhibitors of the interaction of HDM2 and/or MDM2 and p53 are also useful for treating cancer, inhibiting cell growth/replication, and inducing cellular apoptosis and necrosis, when administered along with agents that cause or induce DNA damage (see Chen et al. Proc. Natl. Acad. Sci. USA 95:195–200 (1998)). Compounds of the present invention may be used to treat cancer, inhibit cell growth/replication, and induce cellular apoptosis and necrosis, by administering a compound of the present invention along with agents that cause or induce DNA damage. Agents that induce DNA damage include radiation and chemical agents. The radiation can be administered either internally or externally. Chemical agents include any compounds or elements that cause or induce damage to DNA.

The compounds of the present invention may be administered in an effective amount within the dosage range of about 0.01 mg/kg to about 300 mg/kg, preferably between 1.0 mg/kg to 100 mg/kg body weight. Compounds of the present invention may be administered in a single daily dose, or the total daily dosage may be administered in divided doses of two, three or four times daily.

Preparation of Compounds

The present invention is also concerned with the syntheses of substituted 1,4-benzodiazepin-2,5-dione carboxylic acids. The compounds of the present invention can be prepared utilizing the modification of Ugi condensation products, according to the synthetic pathway shown in Scheme 1 or Scheme 2 and as detailed in Keating and Armstrong, J. Am. Chem. Soc., 118: 2574–2583 (1996).

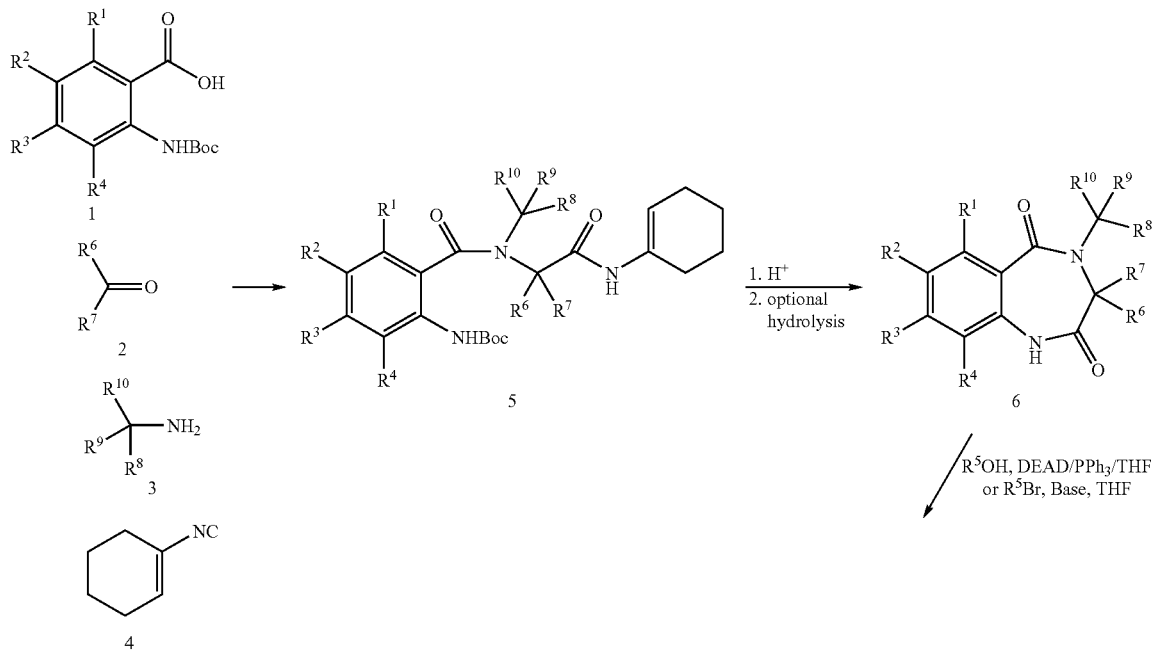

SCHEME 1

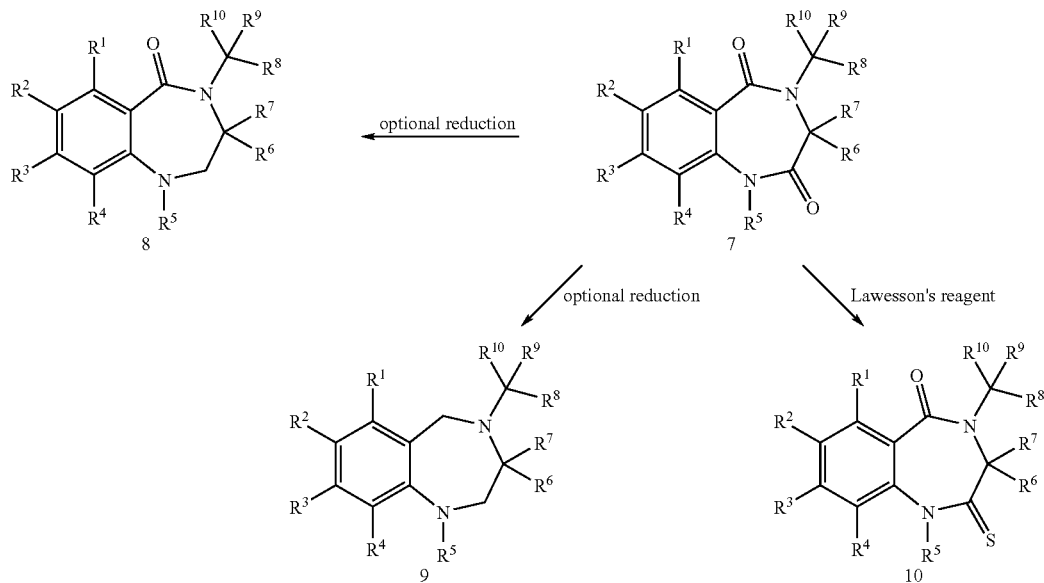
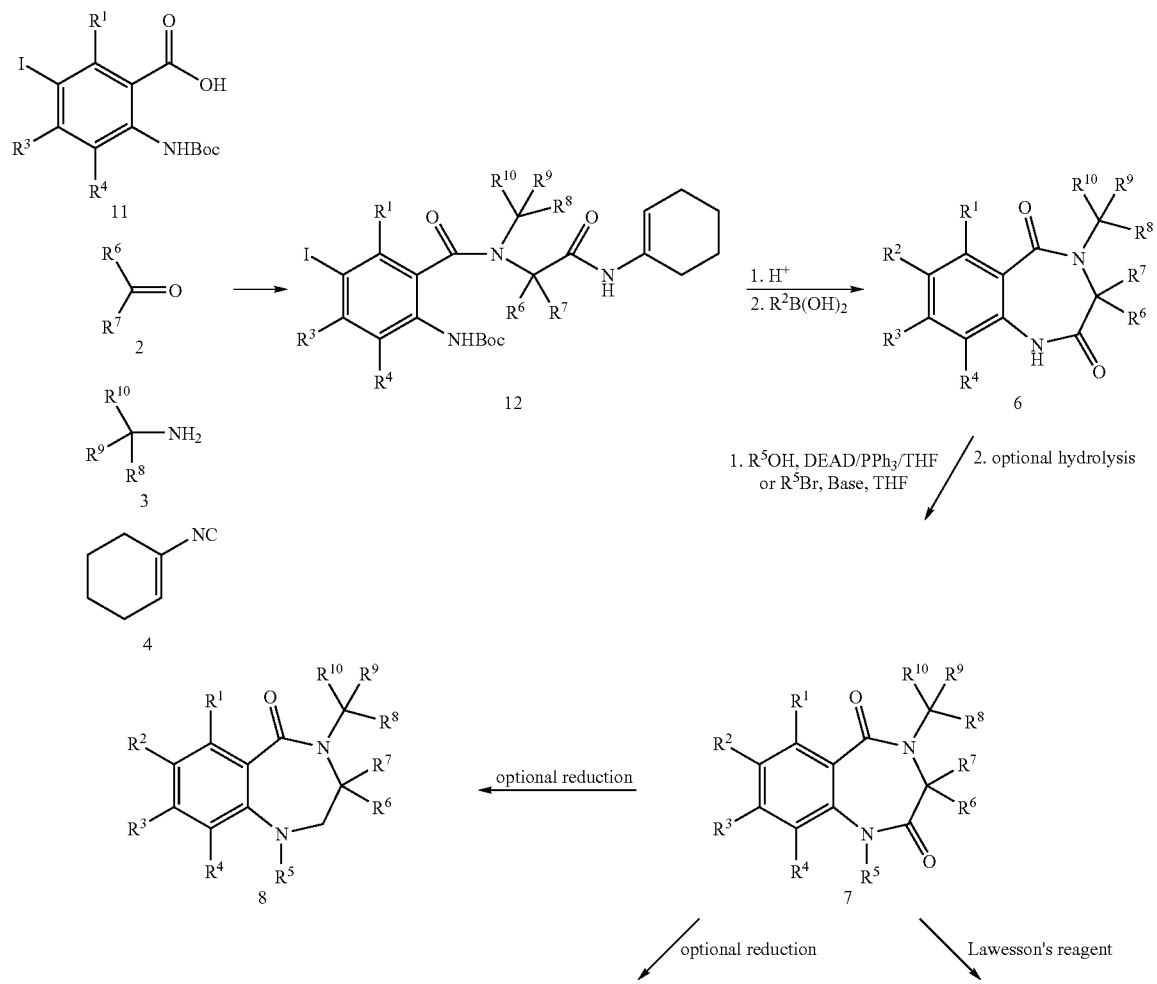
SCHEME 2

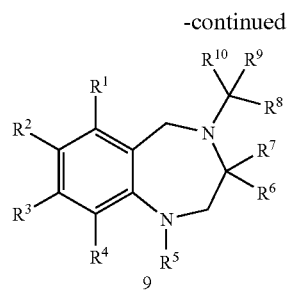

9

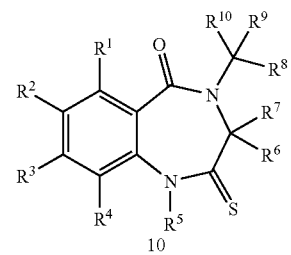

10

Appropriately substituted or unsubstituted anthranilic acids 1 or 11, amines 3, aldehydes or ketones 2 can be used to prepare the compounds of the present invention, wherein $R^1$, $R^2$, $R^3$, $R^4$, $R^6$, $R^7$, $R^8$, $R^9$, and $R^{10}$ are defined above. The acid compounds of the present invention can be prepared by optional hydrolysis of ester using a base, such as NaOH, in an appropriate solvent, such as methanol/water. In Scheme 2, the standard Suzuki (Miyaura, N; Yanagi, T.; Suzuki, A., *Synth. Commun.*, 11: 513 (1981)) cross coupling condition can be used to introduce $R^2$ (from compound 12 to 6). While $R^5$ is selected as a group other than hydrogen, $R^5$ can be introduced by using $R^5Br$ in the presence of a base, such as NaH, and a solvent, such as THF, or by using a standard Mitsunobu coupling procedure (Mitsunobu, O., *Synthesis*, 1, (1981)) such as diethyl azodicarboxylate, and triphenylphosphine in THF. Compound 7 can be converted into compound 8 or 9 by using an appropriate reducing reagent, such as $BH_3.S(Me)_2$, in a solvent such as THF. Compound 10 can be made through reaction of compound 7 with Lawesson's reagent (2,4-bis(4-methoxyphenyl)-1,3-dithia-2,4-diphosphetane-2,4-disulfide) in a solvent such as THF.

The following examples illustrate, but do not limit, the compounds, methods and compositions of the present invention. Other suitable modifications and adaptations of the variety of conditions and parameters normally encountered in clinical therapy and which are obvious to those skilled in the art are within the spirit and scope of the invention.

EXAMPLES

The compounds in the examples below were synthesized by the following general procedures.

General Procedure for the Synthesis of Non-commercially Available Anthranilic Acids A solution of the appropriate aniline (50.0 mmol) in acetic acid (30.0 mL) was heated to 45° C. Bromine (55.5 mmol, 2.8 mL) was then added dropwise at a rate to keep the temperature between 50–55° C. The temperature was held at 50° C. for 1.5 h. The reaction was allowed to cool to ambient temperature and was poured into ice with stirring. Sodium bisulfite (1.0 g) was added and stirred for 30 min. The solution was extracted with ethyl acetate (2×50.0 mL). The combined organic extracts were washed with saturated sodium bicarbonate, brine, dried over sodium sulfate, filtered and concentrated in vacuo to give a dark oil. The oil was purified by flash chromatography (silica gel, 5–10% ethyl acetate in hexanes) to give the aryl bromide as a light brown oil.

A solution of the aryl bromide (12.0 mmol) in N,N-dimethylformamide (8.0 mL) was stirred at ambient temperature. Copper cyanide (15.0 mmol, 1.3 g) was added and the reaction was heated to 155° C. for 4 h. The reaction was allowed to cool and poured into a solution of ethylene diamine (0.1 mL) in water (130.0 mL) and stirred for 30 min. The solution was extracted with ethyl acetate (2×70.0 mL). The organic extracts were combined and washed with saturated ammonium chloride and brine, dried with sodium sulfate and concentrated in vacuo. The residue was then purified by flash chromatography (silica gel, 10% ethyl acetate in hexane) to give the aryl cyanide as a orange oil.

To a solution of the aryl cyanide (1.5 mmol) in acetic acid (2.0 mL) was added 50% sulfuric acid (6.0 mL), The reaction was heated to reflux for 2.5 h. The reaction was allowed to cool to ambient temperature and poured into ice (50.0 g). The solution was neutralized with potassium hydroxide (6M) and extracted with ethyl acetate (2×40.0 mL). The combined organics were washed with brine and dried with sodium sulfate, filtered and dried in vacuo to a solid. The solid was purified by flash chromatography (silica gel, 15% ethyl acetate in methylene chloride to 8% methanol in methylene chloride) to give the anthranilic acid as a white solid.

To a solution of the anthranilic acid (4.2 mmol) in 1,4-dioxane (20.0 mL) and 10% sodium hydroxide (5.0 mL) was added di-tertbutyl-dicarbonate (12.0 mmol). The reaction was stirred at ambient temperature for 3 days. The reaction was then concentrated in vacuo and poured into water (25.0 mL) and ethyl acetate (50.0 mL). It was then acidified with cold 10% citric acid. The organic layers were washed with brine and dried with sodium sulfate and filtered. The organics were concentrated in vacuo to a solid and triturated with hexane. The solids were filtered, and washed with hexane and dried under high vacuum to give the title compound as a white solid.

General Procedure for the Synthesis of Benzodiazepine Compounds

A solution of the aldehyde (0.20 mmol) and amino ester (0.20 mmol) in methanol (2.0 mL) were shaken at ambient temperature for 30 min. To this solution was added a solution of cyclohexene-1-isonitrile (0.21 mmol) in hexanes, followed by the anthranilic acid (0.20 mmol). The solution was then shaken for 3 days at ambient temperature. The reaction was cooled in a ice bath and acetyl chloride (0.2 mL) was added slowly. The solution was then shaken for an additional 3 h and concentrated in vacuo. The residue was purified using pre-packed silica cartridges (methylene chloride to 10% ethyl acetate in methylene chloride). The pure ester was then concentrated back down in vacuo, dissolved in methanol (1.5 mL), and 10% sodium hydroxide (0.15 mL) was added. The reaction mixture was shaken overnight at ambient temperature. The solution was then concentrated in vacuo and acidified with hydrochloric acid (1M). The precipitates were extracted with ethyl acetate, separated and the organics were concentrated in vacuo. The residue was purified using pre-packed silica cartridges (8% ethyl acetate in methylene chloride to 10% methanol in methylene chloride) to give the title compounds (0.015–0.050 g).

General Procedure for the Alkylation of Benzodiazepine Compounds

To a solution of the benzodiazepine (0.1 mmol) and alcohol (0.2 mmol) in tetrahydrofuran (1.0 mL) was added triphenylphosphine (0.2 mmol, 0.052 g) in tetrahydrofuran (1.0 mL). The solution was shaken 5 minutes then diisopropyl azodicarboxylate (0.2 mmol, 0.040 mL) was added, and the mixture was shaken at ambient temperature overnight. The reaction was concentrated in vacuo. The residue was purified by preparative plate chromatography (silica gel, 20% ethyl acetate in methylene chloride, bottom band). The isolated ester was dissolved in methanol (1 mL) and sodium hydroxide (1M, 0.2 mL) was added and the reaction mixture was shaken at ambient temperature overnight. The reaction was concentrated in vacuo, water (0.5 mL) was added, followed by acidification with hydrochloric acid (1M, 0.3 mL). The resulting precipitate was extracted with ethyl acetate (1 mL) and separated. The organics were dried in vacuo and the residues purified using a preparative plate chromatography (silica gel, 8% methanol in methylene chloride, bottom band) to give the title compounds (0.012–0.030 g).

General Procedure for the Boronic Acid Cross Coupling of Benzodiazepine Compounds Benzodiazepine (0.05 mmol), boronic acid (3 eq, 0.15 mmol), and Pd(PPh$_3$)$_4$ (0.04 eq, 0.002 mmol) were placed in a 2 mL vial equipped with a magnetic stir bar. The vial was fitted with a rubber septum then evacuated and backflushed with dry N$_2$. Tetrahydrofuran (THF, 0.8 mL) and 2M Na$_2$CO$_3$ (0.2 mL) were added to the vial via syringe. The reaction vessel was capped tightly under a N$_2$ purge then heated to 50° C. for 12 h. After cooling to ambient temperature, the solvent was removed under reduced pressure. The residue was then purified by Sep-Pak (10 g silica gel, methylene chloride to 10% ethyl acetate in methylene chloride) to give the title compound.

General Procedure for the Reduction of 1,4-benzodiazepines

1) The benzodiazepine ester (0.070 mmol) was placed in a 4 mL vial equipped with a magnetic stir bar. The vial was fitted with a rubber septum then evacuated and backflushed with N$_2$. Borane-dimethylsulfide (4 eq., 0.28 mmol, 0.14 mL of 2M THF solution) was added via syringe. The reaction was stirred at ambient temperature for 15 hours. The solvent was removed under reduced pressure then the residue was dissolved in ethyl acetate. The organic phase was washed with 1M NaOH then the aqueous phase was extracted twice with ethyl acetate. The combined organic phase was dried over anhydrous magnesium sulfate, filtered, and the solvent removed under reduced pressure. The mono- and di-reduced products were separated by column chromatography on silica gel, eluting with 10% ethyl acetate in hexanes to give the title compound.

2) The benzodiazepine acid (0.023 mmol) was placed in a 4 mL vial equipped with a magnetic stir bar. The vial was fitted with a rubber septum then evacuated and backflushed with N$_2$. Dry THF (1 mL) and borane-dimethylsulfide (4 eq., 0.093 mmol, 46 µL of 2M THF solution) were successively added via syringe and microsyringe, respectively. The reaction was stirred at ambient temperature for 16 hours then additional borane-dimethylsulfide (8 eq., 0.186 mmol, 92 µL of 2M THF solution) was added to the reaction. The reaction was stirred at ambient temperature for an additional 4 hours then the solvent was removed under reduced pressure. The residue was purified by column chromatography using a 5 g silica gel SEP-pak column, eluting with 20% ethyl acetate in dichloromethane. The amide reduction products were further separated by preparative TLC on a 1000 micron silica gel plate, developed with 20% ethyl acetate in hexanes to give the title compound.

General Procedure for the Preparation of 1,4-benzodiazepine Amides

The 1,4-benzodiazepine carboxylic acid (0.057 mmol) and EDC (1.5 eq., 0.086 mmol, 16.5 mg) were placed in a 4 mL vial equipped with a magnetic stir bar. The vial was fitted with a rubber septum, then evacuated and backflushed with dry N$_2$. Dry dichloromethane (2 mL) was added via syringe. Once the solids dissolved, the amine (1.5 eq, 0.086 mmol) and triethylamine (2.5 eq., 0.143 mmol, 20 µL) were successively added via microsyringe. The reaction was stirred at ambient temperature for 2 hours then the volatiles were removed under reduced pressure. The crude product was purified by column chromatography using a 5 g silica gel SEP-pak column eluting with 50% ethyl acetate in dichloromethane.

Example 1

[7-Iodo-2,5-dioxo-3-(4-trifluoromethylphenyl)-1,2,3,5-tetrahydro-benzo[e][1,4]diazepin-4-yl]phenylacetic acid $^1$H NMR (400 MHz, DMSO-d$_6$): δ 10.68 (s, 0.4H), 10.52 (s, 0.6H), 7.79 (s, 0.4H), 7.72 (s, 0.6H), 7.52–7.22 (m, 9H), 7.00 (m, 1H), 6.63 (d, J=8.4 Hz, 0.4H), 6.53 (d, J=8.4 Hz, 0.6H) 6.36 (s, 1H), 5.96 (s, 0.6H), 5.28 (s, 0.4H). Mass spectrum (LCMS, ESI pos) Calcd. for C$_{24}$H$_{16}$F$_3$N$_2$O$_4$I: 580.0; Found: 580.9(M+H).

Example 2

[3-(4-Chlorophenyl)-7-iodo-2,5-dioxo-1,2,3,5-tetrahydro-benzo[e][1,4]diazepin-4-yl]phenylacetic acid $^1$H NMR (400 MHz, DMSO-d$_6$): δ 10.74 (s, 0.6H), 10.56 (s, 0.4H), 7.78–6.89 (m, 11H), 6.64 (d, J=8.7 Hz, 0.6H), 6.56 (d, J=8.7 Hz, 0.4H), 6.30 (br s, 1H), 5.65 (s, 0.4H), 5.14 (s, 0.6H). Mass spectrum (LCMS, ESI pos) Calcd. for C$_{23}$H$_{16}$N$_2$O$_4$ICl: 546.0; Found: 546.8(M+H).

Example 3

[3-(4-ethyl-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.57 (s, 0.5H), 10.40 (s, 0.5H), 7.78–6.54 (m, 12H), 6.35 (s, 0.5H), 6.31 (s, 0.5H), 5.89(s, 0.5H), 5.18 (s, 0.5H), 2.38 (m, 2H), 1.00 (m, 3H). Mass spectrum (LCMS, ESI pos) Calcd. for C$_{25}$H$_{21}$N$_2$O$_4$I: 540.1; Found: 540.8(M+H).

Example 4

[7-Iodo-2,5-dioxo-3-(4-trifluoromethoxy-phenyl)-1,2,3,5-tetrahydro-benzo[e][1,4]diazepin-4-yl]-phenyl-acetic acid $^1$H NMR (400 MHz, DMSO-$d_6$): δ 10.77 (s, 0.6H), 10.55 (s, 0.4H), 7.69–6.99 (m, 11H), 6.63 (d, J=8.6 Hz, 0.6H), 6.55 (d, J=8.6 Hz, 0.4H), 6.31 (br s, 1H), 5.63 (s, 0.4H), 5.18 (s, 0.6H). Mass spectrum (LCMS, ESI pos) Calcd. for $C_{24}H_{16}F_3N_2O_5I$: 596.0; Found: 596.8(M+H).

Example 5

[7-Iodo-3-(4-isopropyl-phenyl)-2,5-dioxo-1,2,3,5-tetrahydro-benzo[e][1,4]diazepin-4-yl]-phenyl-acetic acid $^1$H NMR (400 MHz, DMSO-$d_6$): δ 10.58 (s, 0.6H), 10.40 (s, 0.4H), 7.63–6.54 (m, 12H), 6.30 (br s, 1H), 5.64(s, 0.4H), 5.08 (s, 0.6H), 2.60 (m, 1H), 0.96 (m, 6H). Mass spectrum (LCMS, ESI pos) Calcd. for $C_{26}H_{23}N_2O_4I$: 554.1; Found: 554.9(M+H).

Example 6

[2,5-Dioxo-3-(4-trifluoromethyl-phenyl)-1,2,3,5-tetrahydro-benzo[e][1,4]diazepin-4-yl]-phenyl-acetic acid $^1$H NMR (400 MHz, DMSO-$d_6$): δ 10.70 (s, 0.6H), 10.2 (s, 0.4H), 7.7–6.9 (m, 13H), 6.42 (s, 0.4H), 6.39 (s, 0.6H), 5.86 (s, 0.4H), 5.30 (s, 0.6H). Mass spectrum (LCMS, ESI pos) Calcd. for $C_{24}H_{17}F_3N_2O_4$: 454.1; Found: 455.0(M+H).

Example 7

2-[7-Iodo-2,5-dioxo-3-(4-trifluoromethyl-phenyl)-1,2,3,5-tetrahydro-benzo[e][1,4]diazepin-4-yl]-3-phenyl-propionic acid $^1$H NMR (400 MHz, DMSO-$d_6$): δ 10.81 (s, 0.6H), 10.56 (s, 0.4H), 7.70–7.10 (m, 11H), 6.55 (m, 1H), 5.79 (s, 0.6H), 5.59 (br s, 0.6H), 5.51 (s, 0.4H), 5.31 (br s, 0.4H), 3.35 (m, 2H). Mass spectrum (LCMS, ESI pos) Calcd. for $C_{25}H_{18}F_3N_2O_4I$: 594.0; Found: 595.0(M+H).

Example 8

(7-Iodo-2,5-dioxo-3-phenyl-1,2,3,5-tetrahydro-benzo[e][1,4]diazepin-4-yl)-phenyl-acetic acid $^1$H NMR (400 MHz, DMSO-$d_6$): δ 10.69 (s, 0.6H), 10.47 (s, 0.4H), 7.78–6.79 (m, 12H), 6.63 (d, J=8.3 Hz, 0.6H), 6.54 (d, J=8.3 Hz, 0.4H), 6.38 (s, 0.6H), 6.34 (s, 0.4H), 5.83 (s, 0.4H), 5.23 (s, 0.6H). Mass spectrum (LCMS, ESI pos) Calcd. for $C_{23}H_{17}N_2O_4I$: 512.0; Found: 513.0(M+H).

Example 9

[7-Iodo-2,5-dioxo-3-(3-trifluoromethyl-phenyl)-1,2,3,5-tetrahydro-benzo[e][1,4]diazepin-4-yl]-phenyl-acetic acid $^1$H NMR (400 MHz, DMSO-$d_6$): δ 10.76 (s, 0.6H), 10.53 (s, 0.4H), 7.81–6.90 (m, 11H), 6.61 (d, J=8.7 Hz, 0.6H), 6.54 (d, J=8.6 Hz, 0.4H), 6.40 (s, 0.6H), 6.36 (s, 0.4H), 5.40 (s, 0.6H). Mass spectrum (LCMS, ESI pos) Calcd. for $C_{24}H_{16}F_3N_2O_4I$: 580.0; Found: 580.8(M+H).

Example 10

(7-Iodo-2,5-dioxo-3-p-tolyl-1,2,3,5-tetrahydrobenzo[e][1,4]diazepin-4-yl)-phenylacetic acid $^1$H NMR (400 MHz, DMSO-$d_6$): δ 10.64 (s, 0.6H), 10.45 (s, 0.4H), 7.78–6.54 (m, 11H), 6.37 (s, 0.6H), 6.30 (s, 0.4H), 5.77 (s, 0.4H), 5.16 (s, 0.6H), 5.12 (s, 1H), 2.05 (s, 3H). Mass spectrum (LCMS, ESI pos) Calcd. for $C_{24}H_{19}N_2O_4I$: 526.0; Found: 526.8(M+H).

Example 11

[7-Iodo-3-(4-methoxy-phenyl)-2,5-dioxo-1,2,3,5-tetrahydro-benzo[e][1,4]diazepin-4-yl]-phenyl-acetic acid $^1$H NMR (400 MHz, DMSO-$d_6$): δ 10.64 (s, 0.6H), 10.44 (s, 0.4H), 7.78–6.54 (m, 12H), 6.37 (s, 0.6H), 6.30 (s, 0.4H), 5.72 (s, 0.4H), 5.16 (s, 0.6H), 3.61 (s, 1H), 3.55 (s, 2H). Mass spectrum (LCMS, ESI pos) Calcd. for $C_{24}H_{19}N_2O_5I$: 542.0; Found: 542.8(M+H).

Example 12

(7-Iodo-3-naphthalen-2-yl-2,5-dioxo-1,2,3,5-tetrahydro-benzo[e][1,4]diazepin-4-yl)-phenyl-acetic acid $^1$H NMR (400 MHz, DMSO-$d_6$): δ 10.83 (s, 0.75H), 10.72 (s, 0.25H), 8.01–7.00 (m, 14H), 6.62 (d, J=8.3 Hz, 0.75H), 6.57 (d, J=8.3 Hz, 0.25H), 6.44 (s, 0.75H), 6.21 (s, 0.25H), 5.52 (s, 0.25H), 5.26 (s, 0.75H). Mass spectrum (LCMS, ESI pos) Calcd. for $C_{27}H_{19}N_2O_4I$: 562.0; Found: 562.9(M+H).

Example 13

[3-(4-tert-Butyl-phenyl)-7-iodo-2,5-dioxo-1,2,3,5-tetrahydro-benzo[e][1,4]diazepin-4-yl]-phenyl-acetic acid $^1$H NMR (400 MHz, DMSO-$d_6$): δ 10.61 (s, 0.6H), 10.41 (s, 0.4H), 7.78–6.54 (m, 12H), 6.32 (s, 0.6H), 6.27 (s, 0.4H), 5.76(s, 0.4H), 5.13 (s, 0.6H), 1.12(s, 3H), 1.07 (s, 6H). Mass spectrum (LCMS, ESI pos) Calcd. for $C_{27}H_{25}N_2O_4I$: 568.1; Found: 568.9(M+H).

Example 14

[3-(2-Chloro-phenyl)-7-iodo-2,5-dioxo-1,2,3,5-tetrahydro-benzo[e][1,4]diazepin-4-yl]-phenyl-acetic acid $^1$H NMR (400 MHz, DMSO-$d_6$): δ 10.66 (s, 0.4H), 10.53 (s, 0.6H), 7.81–6.90 (m, 11H), 6.72 (s, 0.4H), 6.61 (d, J=8.7 Hz, 0.4H), 6.54 (d, J=8.6 Hz, 0.6H), 6.36 (s, 0.6H), 5.22 (s, 0.6H), 5.12 (s, 0.4H). Mass spectrum (LCMS, ESI pos) Calcd. for $C_{23}H_{16}N_2O_4ICl$: 546.0; Found: 547.8(M+H).

Example 15

[3-(3-Chloro-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.74 (s, 0.6H), 10.53 (s, 0.4H), 7.79–6.76 (m, 11H), 6.65 (d, J=8.7 Hz, 0.6H), 6.56 (d, J=8.6 Hz, 0.4H), 6.34 (s, 0.6H), 6.31 (s, 0.4H), 5.72 (s, 0.4H), 5.25 (s, 0.6H). Mass spectrum (LCMS, ESI pos) Calcd. for C$_{23}$H$_{16}$N$_2$O$_4$I: 546.0; Found: 546.9(M+H).

Example 16

[3-(4-Benzyloxy-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.66 (s, 0.7H), 10.47 (s, 0.3H), 7.78–6.56 (m, 17H), 6.35 (s, 0.7H), 6.28 (s, 0.3H), 5.66 (s, 0.3H), 5.13 (s, 0.7H), 4.95 (s, 0.5H), 4.89 (s, 1.5H). Mass spectrum (LCMS, ESI pos) Calcd. for C$_{30}$H$_{23}$N$_2$O$_5$I: 618.1; Found: 618.8(M+H).

Example 17

[7-Iodo-2,5-dioxo-3-(4-phenoxy-phenyl)-1,2,3,5-tetrahydro-benzo[e][1,4]diazepin-4-yl]-phenyl-acetic acid $^1$H NMR (400 MHz, DMSO-d$_6$): δ 10.61 (s, 0.5H), 10.41 (s, 0.5H), 7.80–6.55 (m, 17H), 6.33 (s, 0.5H), 5.88 (s, 0.5H), 5.36 (s, 0.5H), 5.22 (s, 0.5H). Mass spectrum (LCMS, ESI pos) Calcd. for C$_{29}$H$_{21}$N$_2$O$_5$I: 604.0; Found: 604.8(M+H).

Example 18

[7-Iodo-2,5-dioxo-3-(2-trifluoromethyl-phenyl)-1,2,3,5-tetrahydro-benzo[e][1,4]diazepin-4-yl]-phenyl-acetic acid $^1$H NMR (400 MHz, DMSO-d$_6$): δ 10.72 (s, 0.5H), 10.61 (s, 0.5H), 7.81–6.54 (m, 12H), 6.40 (s, 0.5H), 5.35 (s, 0.5H), 5.29 (s, 0.5H), 5.08 (s, 0.5H). Mass spectrum (LCMS, ESI pos) Calcd. for C$_{24}$H$_{16}$F$_3$N$_2$O$_4$I: 580.0; Found: 580.9(M+H).

Example 19

3-(3,4-Dichloro-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.79 (s, 0.8H), 10.58 (s, 0.2H), 7.81–6.84 (m, 10H), 6.67 (d, J=8.5 Hz, 0.8H), 6.58 (d, J=8.5 Hz, 0.2H), 6.33 (s, 0.8H), 6.31 (s, 0.2H), 5.35 (s, 0.2H), 5.24 (s, 0.8H). Mass spectrum (LCMS, ESI pos) Calcd. for C$_{23}$H$_{15}$N$_2$O$_4$ICl$_2$: 579.9; Found: 580.8(M+H).

Example 20

[3-(3,4-Dimethoxy-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.64 (s, 0.5H), 10.41 (s, 0.5H), 7.81–7.22 (m, 10H), 6.67 (d, J=8.4 Hz, 0.5H), 6.55 (d, J=8.5 Hz, 0.5H), 6.42 (s, 0.5H), 6.12 (s, 0.5H), 5.62 (s, 0.5H) 5.30 (s, 0.5H), 3.54 (s, 3H), 3.43 (s, 3H). Mass spectrum (LCMS, ESI pos) Calcd. for C$_{25}$H$_{21}$N$_2$O$_6$I: 572.0; Found: 572.8(M+H).

Example 21

[3-(2,3-Dihydro-benzo[1,4]dioxin-6-yl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.65 (s, 0.7H), 10.46 (s, 0.3H), 7.78–6.47 (m, 11H), 6.32 (s, 0.8H), 6.25 (s, 0.8H), 6.23 (s, 0.2H), 5.10 (s, 0.2H), 4.07 (br s, 4H). Mass spectrum (LCMS, ESI pos) Calcd. for C$_{25}$H$_{19}$N$_2$O$_6$I: 570.; Found: 570.90 (M+H).

Example 22

[3-(4-Bromo-2-fluoro-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.74 (s, 0.6H), 10.47 (s, 0.4H), 7.81–7.01 (m, 10H), 6.67 (d, J=8.7 Hz, 0.6H), 6.58 (d, J=8.6 Hz, 0.4H), 6.26 (s, 0.4H), 6.13 (s, 0.6H) 5.77 (s, 0.4H), 5.14 (s, 0.6H). Mass spectrum (LCMS, ESI pos) Calcd. for C$_{23}$H$_{15}$N$_2$O$_4$IBrF: 607.9; Found: 608.8(M+H).

Example 23

[3-(2-Fluoro-4-trifluoromethyl-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.76 (s, 0.8H), 10.47 (s, 0.2H), 7.81–6.81 (m, 10H), 6.66 (d, J=8.4 Hz, 0.8H), 6.56 (d, J=8.4 Hz, 0.2H), 6.31 (s, 0.2H), 6.16 (s, 0.8H) 6.02 (s, 0.2H), 5.29 (s, 0.8H). Mass spectrum (LCMS, ESI pos) Calcd. for C$_{24}$H$_{15}$N$_2$O$_4$IF$_4$: 598.0; Found: 598.9(M+H).

Example 24

[3-(3-Fluoro-4-trifluoromethyl-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.82 (s, 0.8H), 10.61 (s, 0.2H), 7.81–6.90 (m, 10H), 6.65 (d, J=8.5 Hz, 0.8H), 6.58 (d, J=8.5 Hz, 0.2H), 6.31 (s, 0.2H), 6.29 (s, 0.8H) 5.74 (s, 0.2H), 5.29 (s, 0.8H). Mass spectrum (LCMS, ESI pos) Calcd. for C$_{24}$H$_{15}$N$_2$O$_4$IF$_4$: 598.0; Found: 598.9(M+H).

Example 25

[3-(4-Chloro-3-fluoro-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.75 (s, 0.8H), 10.57 (s, 0.2H), 7.81–6.60 (m, 11H), 6.27 (bs, 1H), 5.67 (s, 0.2H), 5.22 (s, 0.8H). Mass spectrum (LCMS, ESI pos) Calcd. for C$_{23}$H$_{15}$N$_2$O$_4$IClF: 564.0; Found: 564.9(M+H).

Example 26

[3-(4-Bromo-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.76 (s, 0.6H), 10.57 (s, 0.4H), 7.80–6.82 (m, 11H), 6.64 (d, J=8.6 Hz, 0.6H), 6.54 (d, J=8.6 Hz, 0.4H), 6.32 (s, 0.6H), 6.27 (s, 0.4H) 5.58 (s, 0.4H), 5.10 (s, 0.6H). Mass spectrum (LCMS, ESI pos) Calcd. for C$_{23}$H$_{16}$N$_2$O$_4$IBr: 589.9; Found: 591.8(M+H).

Example 27

[8-Chloro-3-(4-chloro-phenyl)-2,5-dioxo-1,2,3,5-tetrahydro-benzo[e][1,4]diazepin-4-yl]-phenyl-acetic acid $^1$H NMR (400 MHz, DMSO-d$_6$): δ 10.78 (s, 0.8H), 10.58 (s, 0.2H), 7.53–6.83 (m, 12H), 6.34 (s, 0.8H), 6.30 (s, 0.2H), 5.66 (s, 0.2H), 5.14 (s, 0.8H). Mass spectrum (LCMS, ESI pos) Calcd. for C$_{23}$H$_{16}$N$_2$O$_4$Cl$_2$: 454.0; Found: 454.9(M+H).

Example 28

[7-Chloro-3-(4-chloro-phenyl)-2,5-dioxo-1,2,3,5-tetrahydro-benzo[e][1,4]diazepin-4-yl]-phenyl-acetic acid $^1$H NMR (400 MHz, DMSO-d$_6$): δ 10.79 (s, 0.7H), 10.58 (s, 0.3H), 7.50–6.77 (m, 12H), 6.34 (s, 0.7H), 6.31 (s, 0.3H), 5.69 (s, 0.3H), 5.15 (s, 0.7H). Mass spectrum (LCMS, ESI pos) Calcd. for C$_{23}$H$_{16}$N$_2$O$_4$ICl$_2$: 454.0; Found: 454.9(M+H).

Example 29

[7-Bromo-3-(4-chloro-phenyl)-2,5-dioxo-1,2,3,5-tetrahydro-benzo[e][1,4]diazepin-4-yl]-phenyl-acetic acid $^1$H NMR (400 MHz, DMSO-d$_6$): δ 10.81 (s, 0.7H), 10.61 (s, 0.3H), 7.59–6.92 (m, 11H), 6.80 (d, J=8.6 Hz, 0.7H), 6.72 (d, J=8.6 Hz, 0.3H), 6.33 (s, 0.7H), 6.29 (s, 0.3H) 5.60 (s, 0.3H), 5.13 (s, 0.7H). Mass spectrum (LCMS, ESI pos) Calcd. for C$_{23}$H$_{16}$N$_2$O$_4$ClBr: 498.0; Found: 499.1(M+H).

Example 30

[3-(4-Chloro-phenyl)-7-methoxy-2,5-dioxo-1,2,3,5-tetrahydro-benzo[e][1,4]diazepin-4-yl]-phenyl-acetic acid $^1$H NMR (400 MHz, DMSO-d$_6$): δ 10.52 (s, 0.7H), 10.33 (s, 0.3H), 7.50–6.81 (m, 11H), 6.75 (d, J=8.9 Hz, 0.7H), 6.68 (d, J=8.9 Hz, 0.3H), 6.32 (s, 0.7H), 6.29 (s, 0.3H) 5.47 (s, 0.3H), 5.11 (s, 0.7H), 3.64 (s, 3H). Mass spectrum (LCMS, ESI pos) Calcd. for C$_{24}$H$_{19}$N$_2$O$_5$Cl: 450.1; Found: 450.9 (M+H).

Example 31

[3-(4-Chloro-phenyl)-7-methyl-2,5-dioxo-1,2,3,5-tetrahydro-benzo[e][1,4]diazepin-4-yl]-phenyl-acetic acid $^1$H NMR (400 MHz, DMSO-d$_6$): δ 10.59 (s, 0.6H), 10.39 (s, 0.4H), 7.50–6.85 (m, 11H), 6.72 (d, J=8.1 Hz, 0.7H), 6.65 (d, J=8.1 Hz, 0.3H), 6.33 (s, 0.7H), 6.29 (s, 0.3H) 5.55 (s, 0.3H), 5.14 (s, 0.7H), 2.14 (s, 2H), 2.13 (s, 1H). Mass spectrum (LCMS, ESI pos) Calcd. for C$_{24}$H$_{19}$N$_2$O$_4$Cl: 434.1; Found: 435.0(M+H).

Example 32

[3-(4-Chloro-phenyl)-2,5-dioxo-1,2,3,5-tetrahydronaphtho[2,3-e][1,4]diazepin-4-yl]-phenyl-acetic acid $^1$H NMR (400 MHz, DMSO-d$_6$): δ 10.87 (s, 0.6H), 10.71 (s, 0.4H), 8.21–6.98 (m, 12H), 6.38 (s, 0.6H), 6.32 (s, 0.4H) 5.52 (s, 0.4H), 5.20 (s, 0.6H) 2.14 (s, 2H) 2.13 (s, 1H). Mass spectrum (LCMS, ESI pos) Calcd. for C$_{27}$H$_{19}$N$_2$O$_4$Cl: 470.1; Found: 471.0(M+H).

Example 33

[8-Chloro-2,5-dioxo-3-(4-trifluoromethoxy-phenyl)-1,2,3,5-tetrahydro-benzo[e][1,4]diazepin-4-yl]-phenyl-acetic acid $^1$H NMR (400 MHz, DMSO-d$_6$): δ 10.76 (s, 0.9H), 10.55 (s, 0.1H), 7.53–6.80 (m, 12H), 6.32 (s, 1H), 5.18 (s, 1H). Mass spectrum (LCMS, ESI pos) Calcd. for C$_{24}$H$_{16}$N$_2$O$_5$Cl$_2$F$_3$: 504.1; Found: 505.0(M+H).

Example 34

[7-Chloro-2,5-dioxo-3-(4-trifluoromethoxy-phenyl)-1,2,3,5-tetrahydro-benzo[e][1,4]diazepin-4-yl]-phenyl-acetic acid $^1$H NMR (400 MHz, DMSO-d$_6$): δ 10.81 (s, 0.5H), 10.59 (s, 0.5H), 7.50–7.00 (m, 11H), 6.85 (d, J=8.8 Hz, 0.5H), 6.77 (d, J=8.8 Hz, 0.5H), 6.32 (s, 1H), 5.67 (s, 0.5H), 5.18 (s, 0.5H). Mass spectrum (LCMS, ESI pos) Calcd. for C$_{24}$H$_{16}$N$_2$O$_5$ClF$_3$: 504.1; Found: 504.9(M+H).

Example 35

[7-Bromo-2,5-dioxo-3-(4-trifluoromethoxy-phenyl)-1,2,3,5-tetrahydro-benzo[e][1,4]diazepin-4-yl]-phenyl-acetic acid $^1$H NMR (400 MHz, DMSO-d$_6$): δ 10.78 (s, 0.9H), 10.56 (s, 0.1H), 7.58–6.98 (m, 11H), 6.79 (d, J=8.5 Hz, 0.9H), 6.70 (d, J=8.5 Hz, 0.1H), 6.33 (s, 1H), 5.75 (s, 0.1H), 5.20 (s, 0.9H). Mass spectrum (LCMS, ESI pos) Calcd. for C$_{24}$H$_{16}$N$_2$O$_5$BrF$_3$: 548.0; Found: 548.8(M+H).

Example 36

[7-Methoxy-2,5-dioxo-3-(4-trifluoromethoxy-phenyl)-1,2,3,5-tetrahydro-benzo[e][1,4]diazepin-4-yl]-phenyl-acetic acid $^1$H NMR (400 MHz, DMSO-d$_6$): δ 10.52 (s, 0.6H), 10.30 (s, 0.4H), 7.52–6.79 (m, 11H), 6.74 (d, J=8.8 Hz, 0.6H), 6.66 (d, J=8.8 Hz, 0.4H), 6.33 (s, 0.4H), 6.30 (s, 0.6H) 5.56 (s, 0.4H), 5.16 (s, 0.6H), 3.62 (s, 3H). Mass spectrum (LCMS, ESI pos) Calcd. for C$_{25}$H$_{19}$N$_2$O$_6$F$_3$: 500.1; Found: 500.9 (M+H).

Example 37

[7-Methyl-2,5-dioxo-3-(4-trifluoromethoxy-phenyl)-1,2,3,5-tetrahydro-benzo[e][1,4]diazepin-4-yl]-phenyl-acetic acid $^1$H NMR (400 MHz, DMSO-d$_6$): δ 10.60 (s, 0.6H), 10.41 (s, 0.4H), 7.51–7.00 (m, 11H), 6.71 (d, J=8.2 Hz, 0.6H), 6.64

(d, J=8.2 Hz, 0.4H), 6.30 (s, 1H), 5.51 (s, 0.4H), 5.16 (s, 0.6H), 2.11 (s, 2H), 2.10 (s, 1H). Mass spectrum (LCMS, ESI pos) Calcd. for $C_{25}H_{19}N_2O_5F_3$: 484.1; Found: 485.0 (M+H).

Example 38

[2,5-Dioxo-3-(4-trifluoromethoxy-phenyl)-1,2,3,5-tetrahydro-naphtho[2,3-e][1,4]diazepin-4-yl]-phenyl-acetic acid $^1$H NMR (400 MHz, DMSO-d$_6$): δ 10.86 (s, 0.8H), 10.51 (s, 0.2H), 7.72–6.90 (m, 15H), 6.37 (s, 1H), 5.57 (s, 0.4H), 5.25 (s, 0.6H). Mass spectrum (LCMS, ESI pos) Calcd. for $C_{28}H_{19}N_2O_5F_3$: 520.1; Found: 521.0(M+H).

Example 39

2-[3-(4-Chloro-phenyl)-7-iodo-2,5-dioxo-1,2,3,5-tetrahydro-benzo[e][1,4]diazepin-4-yl]-3-phenyl-propionic acid $^1$H NMR (400 MHz, DMSO-d$_6$): δ 10.76 (s, 0.6H), 10.51 (s, 0.4H), 7.72–6.95 (m, 11H), 6.57 (d, J=8.9 Hz, 0.4H), 6.54 (d, J=8.9 Hz, 0.6H), 5.57 (br s, 1H), 5.39 (s, 0.6H) 5.28 (s, 0.4H), 3.41 (d, J=4.2 Hz, 0.8H), 3.37 (d, J=4.2 Hz, 1.2H). Mass spectrum (LCMS, ESI pos) Calcd. for $C_{24}H_{18}N_2O_4ICl$: 560.0; Found: 560.8(M+H).

Example 40

3-(4-Chloro-phenyl)-2-[3-(4-chloro-phenyl)-7-iodo-2,5-dioxo-1,2,3,5-tetrahydro-benzo[e][1,4]diazepin-4-yl]-propionic acid $^1$H NMR (400 MHz, DMSO-d$_6$): δ 10.76 (s, 0.8H), 10.54 (s, 0.2H), 7.72–6.95 (m, 10H), 6.58(d, J=8.4 Hz, 0.2H), 6.54 (d, J=8.4 Hz, 0.8H), 5.54 (br s, 1.4H), 5.35 (s, 0.2H), 5.13 (s, 0.4H), 3.41 (d, J=4.4 Hz, 0.8H), 3.37 (d, J=4.4 Hz, 1.2H). Mass spectrum (LCMS, ESI pos) Calcd. for $C_{24}H_{17}N_2O_4ICl_2$: 594.0; Found: 594.8 (M+H).

Example 41

2-[3-(4-Chloro-phenyl)-7-iodo-2,5-dioxo-1,2,3,5-tetrahydro-benzo[e][1,4]diazepin-4-yl]-3-(4-hydroxy-phenyl)-propionic acid $^1$H NMR (400 MHz, DMSO-d$_6$): δ 10.74 (s, 0.9H), 10.55 (s, 0.1H), 9.16 (s, 0.1H), 9.11 (s, 0.9H), 7.71 (s, 0.2H), 7.62 (d, J=1.9 Hz, 0.8H), 7.49 (m, 1H), 7.15–6.96 (m, 6H), 6.57(m, 3H), 5.63 (br s, 0.8H), 5.46 (br s, 0.8H), 5.21 (br s, 0.4H), 3.25 (m, 2H). Mass spectrum (LCMS, ESI pos) Calcd. for $C_{24}H_{18}N_2O_5ICl$: 576.0; Found: 576.8(M+H).

Example 42

2-[3-(4-Chloro-phenyl)-7-iodo-2,5-dioxo-1,2,3,5-tetrahydro-benzo[e][1,4]diazepin-4-yl]-3-cyclohexyl-propionic acid $^1$H NMR (400 MHz, DMSO-d$_6$): δ 10.96 (s, 0.9H), 10.84 (s, 0.1H), 7.76 (d, J=2.1 Hz, 1H), 7.57 (dd, J=2.2 Hz, 8.4 Hz, 1H), 7.23 (d, J=8.6 Hz, 1H), 7.12 (d, J=8.4 Hz, 2H), 6.61 (d, J=8.6 Hz, 1H), 5.51 (br s, 1H), 5.43 (s, 1H), 1.87–0.83(m, 13H), 3.23 (d, J=5.1 Hz, 1H). Mass spectrum (LCMS, ESI pos) Calcd. for $C_{24}H_{24}N_2O_4ICl$: 566.0; Found: 566.9(M+H).

Example 43

2-[7-Iodo-2,5-dioxo-3-(4-trifluoromethoxy-phenyl)-1,2,3,5-tetrahydro-benzo[e][1,4]diazepin-4-yl]-3-phenyl-propionic acid $^1$H NMR (400 MHz, DMSO-d$_6$): δ 10.77 (s, 0.8H), 10.52 (s, 0.2H), 7.72–6.95 (m, 11H), 6.57 (d, J=8.6 Hz, 0.2H), 6.52 (d, J=8.6 Hz, 0.8H), 5.58 (br s, 1.2H), 5.44 (s, 0.4H), 5.29 (s, 0.4H), 3.42 (d, J=5.5 Hz, 0.8H), 3.39 (d, J=5.5 Hz, 1.2H). Mass spectrum (LCMS, ESI pos) Calcd. for $C_{25}H_{18}N_2O_5IF_3$: 610.0; Found: 610.9(M+H).

Example 44

3-(4-Chloro-phenyl)-2-[7-iodo-2,5-dioxo-3-(4-trifluoromethoxy-phenyl)-1,2,3,5-tetrahydro-benzo[e][1,4]diazepin-4-yl]-propionic acid $^1$H NMR (400 MHz, DMSO-d$_6$): δ 10.76 (s, 0.8H), 10.54 (s, 0.2H), 7.72–6.95 (m, 10H), 6.57(d, J=8.6 Hz, 0.2H), 6.52 (d, J=8.6 Hz, 0.8H), 5.59 (br s, 1.4H), 5.54 (s, 0.2H), 5.40 (s, 0.2H), 5.16 (s, 0.2H), 3.42 (d, J=5.2 Hz, 0.8H), 3.39 (d, J=5.2 Hz, 1.2H). Mass spectrum (LCMS, ESI pos) Calcd. for $C_{25}H_{17}N_2O_5IF_3$: 644.0; Found: 644.8(M+H).

Example 45

3-(4-Hydroxy-phenyl)-2-[7-iodo-2,5-dioxo-3-(4-trifluoromethoxy-phenyl)-1,2,3,5-tetrahydro-benzo[e][1,4]diazepin-4-yl]-propionic acid $^1$H NMR (400 MHz, DMSO-d$_6$): δ 10.76 (s, 1H), 9.15 (s, 1H), 7.60 (d, J=1.6 Hz, 4H), 7.48 (dd, J=1.9 Hz, 8.4 Hz, 3H), 7.05 (m, 3H), 6.59 (d, J=8.5 Hz, 0.6H), 6.54 (d, J=8.5 Hz, 0.4H), 5.53 (br, s, 2H), 3.28 (m, 2H). Mass spectrum (LCMS, ESI pos) Calcd. for $C_{25}H_{18}N_2O_6IF_3$: 626.0; Found: 626.9(M+H).

Example 46

3-Cyclohexyl-2-[7-iodo-2,5-dioxo-3-(4-trifluoromethoxy-phenyl)-1,2,3,5-tetrahydro-benzo[e][1,4]diazepin-4-yl]-propionic acid $^1$H NMR (400 MHz, DMSO-d$_6$): δ 10.94 (s, 0.9H), 10.84 (s, 0.1H), 7.71 (d, J=1.9 Hz, 1H), 7.54 (dd, J=2.1 Hz, 8.4 Hz, 1H), 7.24 (d, J=8.4 Hz, 2H), 7.14 (d, J=8.4 Hz, 2H), 6.59 (d, J=8.6 Hz, 1H), 5.51 (br s, 2H), 1.87–0.83 (m, 13H). Mass spectrum (LCMS, ESI pos) Calcd. for $C_{25}H_{24}N_2O_5IF_3$: 616.1; Found: 616.9(M+H).

Example 47

[1-Benzyl-3-(4-chloro-phenyl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 7.62–6.97 (m, 17H), 6.22 (s, 0.6H), 6.19 (s, 0.4H), 5.65 (br s, 1H), 5.40 (m, 1H), 4.80 (m, 1H). Mass spectrum (LCMS, ESI pos) Calcd. for $C_{30}H_{22}N_2O_4ICl$: 636.0; Found: 636.9(M+H).

Example 48

[3-(4-Chloro-phenyl)-7-iodo-2,5-dioxo-1-phenethyl-1,2,3,5-tetrahydro-benzo[e][1,4]diazepin-4-yl]-phenyl-acetic acid $^1$H NMR (400 MHz, CDCl$_3$): δ 7.71 (s, 1H), 7.56 (m, 2H), 7.31 (m, 8H), 7.05 (m, 5H), 6.89 (s, 1H), 6.20 (s, 1H), 5.85 (s, 0.4H), 5.31 (s, 0.6H), 4.23 (m, 1H), 3.85 (m, 1H), 2.85 (m, 0.5H), 2.62 (m, 1.5H). Mass spectrum (LCMS, ESI pos) Calcd. for C$_{31}$H$_{24}$N$_2$O$_4$ICl: 650.0; Found: 650.9(M+H).

Example 49

[3-(4-Chloro-phenyl)-7-iodo-1-isobutyl-2,5-dioxo-1,2,3,5-tetrahydro-benzo[e][1,4]diazepin-4-yl]-phenyl-acetic acid $^1$H NMR (400 MHz, DMSO-d$_6$): δ 7.68 (m, 1H), 7.59 (m, 1H), 7.51 (d, J=6.5 Hz, 1H), 7.39 (m, 5H), 7.12 (m, 1H), 6.95 (m, 3H), 6.26 (s, 0.6H), 6.13 (s, 0.4H), 5.57 (s, 0.6H), 5.34 (s, 0.4H), 4.10 (m, 2H), 1.60 (m, 1H), 0.65 (m, 6H). Mass spectrum (LCMS, ESI pos) Calcd. for C$_{27}$H$_{24}$N$_2$O$_4$ICl: 602.0; Found: 602.9(M+H).

Example 50

[3-(4-Chloro-phenyl)-7-iodo-1-(3-methyl-butyl)-2,5-dioxo-1,2,3,5-tetrahydro-benzo[e][1,4]diazepin-4-yl]-phenyl-acetic acid $^1$H NMR (400 MHz, DMSO-d$_6$): δ 7.68 (m, 1H), 7.53 (m, 2H), 7.30 (m, 4H), 7.06 (m, 3H), 6.87 (m, 1H), 6.26 (s, 1H), 6.04 (m, 1.6H), 5.35 (s, 0.4H) 4.07 (m, 1H), 3.44 (m, 1H), 1.40 (m, 1H), 1.24 (m, 1H), 1.13 (m, 1H), 0.75 (m, 6H). Mass spectrum (LCMS, ESI pos) Calcd. for C$_{28}$H$_{26}$N$_2$O$_4$ICl: 616.1; Found: 616.9(M+H).

Example 51

[3-(4-Chloro-phenyl)-1-cyclobutylmethyl-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 7.65 (m, 1H), 7.58 (m, 1H), 7.49 (m, 2H), 7.40 (m, 4H), 7.11 (m, 2H), 6.95 (m, 2H), 6.23 (s, 0.7H), 6.10 (s, 0.7H), 5.56 (s, 0.3H), 5.33 (s, 0.3H), 4.18 (m, 1H), 3.52 (m, 1H), 2.19 (m, 1H), 1.68 (m, 4H), 1.40 (m, 2H). Mass spectrum (LCMS, ESI pos) Calcd. for C$_{28}$H$_{24}$N$_2$O$_4$ICl: 614.0; Found: 614.9(M+H).

Example 52

[3-(4-Chloro-phenyl)-1-cyclopentylmethyl-7-iodo-2,5-dioxo-1,2,3,5-tetrahydro-benzo[e][1,4]diazepin4-yl]-phenyl-acetic acid $^1$H NMR (400 MHz, DMSO-d$_6$): δ 7.66 (m, 1H), 7.53 (m, 3H), 7.38 (s, 1H), 7.25 (s, 4H), 7.02 (m, 3H), 6.85 (m, 1H), 6.34 (s, 0.7H), 6.10 (br s, 1H), 5.44 (s, 0.3H), 4.02 (m, 1.3H), 3.48 (m, 0.7H), 1.34 (m, 6H), 0.77 (m, 2H). Mass spectrum (LCMS, ESI pos) Calcd. for C$_{29}$H$_{26}$N$_2$O$_4$ICl: 628.1; Found: 628.9(M+H).

Example 53

[3-(4-Chloro-phenyl)-1-cyclohexylmethyl-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 7.64 (m, 1H), 7.53 (m, 3H), 7.35 (s, 1H), 7.27 (s, 4H), 7.05 (m, 2H), 6.85 (m, 1H), 6.34 (s, 0.7H), 6.06 (br s, 1H), 5.47 (s, 0.3H), 4.98 (m, 0.7H), 3.23 (m, 1.3H), 1.53–0.6 (m, 11H). Mass spectrum (LCMS, ESI pos) Calcd. for C$_{30}$H$_{28}$N$_2$O$_4$ICl: 642.9; Found: 643.0 (M).

Example 54

[3-(4-Chloro-phenyl)-7-iodo-1-(2-methyl-benzyl)-2,5-dioxo-1,2,3,5-tetrahydro-benzo[e][1,4]diazepin-4-yl]-phenyl-acetic acid $^1$H NMR (400 MHz, DMSO-d$_6$): δ 7.68 (s, 0.4H), 7.60 (s, 0.6H), 7.51 (d, J=7.4 Hz, 1H), 7.44 (m, 1H), 7.38 (s, 1H), 7.26 (m, 4H), 7.05 (m, 6H), 6.87 (m, 2H), 6.29 (s, 0.7H), 6.17 (s, 1H), 5.55 (s, 0.3H), 5.34 (d, J=15.8 Hz, 0.3H), 5.27 (d, J=15.8 Hz, 0.7H), 4.93 (d, J=15.8 Hz, 0.3H), 4.68 (d, J=15.8 Hz, 0.7H), 2.20 (s, 1H), 1.98 (s, 2H). Mass spectrum (LCMS, ESI pos) Calcd. for C$_{31}$H$_{24}$N$_2$O$_4$ICl: 650.0; Found: 650.9(M+H).

Example 55

[3-(4-Chloro-phenyl)-7-iodo-1-(3-methyl-benzyl)-2,5-dioxo-1,2,3,5-tetrahydro-benzo[e][1,4]diazepin-4-yl]-phenyl-acetic acid $^1$H NMR (400 MHz, DMSO-d$_6$): δ 7.62 (s, 0.4H), 7.59 (s, 0.6H), 7.52 (d, J=7.0 Hz, 1H), 7.45 (m, 3H), 7.26 (m, 3H), 7.09 (m, 5H), 6.90 (m, 3H), 6.74 (s, 0.6H), 6.34 (s, 0.4H), 6.17 (m, 1H), 5.53 (d, J=15.6 Hz, 0.4H), 5.27 (d, J=15.6 Hz, 0.6H), 4.83 (d, J=15.6 Hz, 0.4H), 4.64 (d, J=15.6 Hz, 0.6H), 2.18 (s, 3H). Mass spectrum (LCMS, ESI pos) Calcd. for C$_{31}$H$_{24}$N$_2$O$_4$ICl: 650.0; Found: 650.9(M+H).

Example 56

[3-(4-Chloro-phenyl)-7-iodo-1-(4-methyl-benzyl)-2,5-dioxo-1,2,3,5-tetrahydro-benzo[e][1,4]diazepin-4-yl]-phenyl-acetic acid $^1$H NMR (400 MHz, DMSO-d$_6$): δ 7.57 (m, 1H), 7.43 (m, 3H), 7.31 (m, 4H), 7.10 (m, 3H), 6.99 (m, 3H), 6.84 (m, 2H), 6.35 (s, 0.4H), 6.19 (s, 1H), 5.55 (d, J=15.1 Hz, 0.4H), 5.42 (s, 0.6H), 5.27 (d, J=15.1 Hz, 0.6H), 4.77 (d, J=15.1 Hz, 0.4H), 4.59 (d, J=15.1 Hz, 0.6H), 2.20 (s, 3H). Mass spectrum (LCMS, ESI pos) Calcd. for C$_{31}$H$_{24}$N$_2$O$_4$ICl: 650.0; Found: 650.9(M+H).

Example 57

[3-(4-Chloro-phenyl)-7-iodo-1-naphthalen-2-ylmethyl-2,5-dioxo-1,2,3,5-tetrahydro-benzo[e][1,4]diazepin-4-yl]-phenyl-acetic acid $^1$H NMR (400 MHz, DMSO-d$_6$): δ 7.79 (m, 4H), 7.58 (m, 2H), 7.46 (m, 4H), 7.31 (m, 2H), 7.15 (s, 2H), 7.05 (m, 1H), 6.90 (m, 1H), 6.36 (m, 0.6H), 6.23 (s, 1H), 5.76 (d, J=15.8 Hz, 0.4H), 5.47 (d, J=15.8 Hz, 0.6H), 5.44 (s, 0.4H), 5.00 (d, J=15.8 Hz, 0.4H), 4.84 (d, J=15.8 Hz, 0.6H), 2.20 (s, 3H).

Mass spectrum (LCMS, ESI pos) Calcd. for $C_{34}H_{24}N_2O_4ICl$: 686.0; Found: 686.9(M+H).

Example 58

[3-(4-Chloro-phenyl)-7-iodo-2,5-dioxo-1-pyridin-2-ylmethyl-1,2,3,5-tetrahydro-benzo[e][1,4]diazepin-4-yl]-phenyl-acetic acid $^1$H NMR (400 MHz, DMSO-d$_6$): δ 8.48 (m, 1H), 7.73 (m, 2H), 7.65 (m, 2H), 7.53 (m, 4H), 7.34 (m, 4H), 7.09 (m, 2H), 6.90 (m, 1H), 6.32 (s, 0.6H), 6.20 (s, 1H), 5.89 (br s, 0.4H), 5.36–4.89 (m, 2H). Mass spectrum (LCMS, ESI pos) Calcd. for $C_{29}H_{21}N_3O_4ICl$: 637.0; Found: 638.0(M+H).

Example 59

[3-(4-Chloro-phenyl)-7-iodo-2,5-dioxo-1-pyridin-3-ylmethyl-1,2,3,5-tetrahydro-benzo[e][1,4]diazepin-4-yl]-phenyl-acetic acid $^1$H NMR (400 MHz, DMSO-d$_6$): δ 8.40 (m, 1H), 7.52 (m, 3H), 7.27 (m, 4H), 7.11 (m, 4H), 6.96 (m, 2H), 6.82 (m, 2H), 6.33 (s, 0.6H), 6.24 (s, 0.4H), 6.15 (s, 0.6H), 5.69 (m, 0.4H), 5.35 (m, 0.6H), 5.31 (m, 0.4H), 4.85 (m, 1H). Mass spectrum (LCMS, ESI pos) Calcd. for $C_{29}H_{21}N_3O_4ICl$: 637.0; Found: 638.1(M+H).

Example 60

[3-(4-Chloro-phenyl)-7-iodo-2,5-dioxo-1-pyridin-4-ylmethyl-1,2,3,5-tetrahydro-benzo[e][1,4]diazepin-4-yl]-phenyl-acetic acid $^1$H NMR (400 MHz, DMSO-d$_6$): δ 8.41 (br s, 1H), 7.64 (m, 1H), 7.48 (m, 4H), 7.32 (m, 4H), 7.11 (m, 3H), 6.91 (m, 3H), 6.34 (s, 0.6H), 6.23 (s, 0.4H), 6.16 (s, 0.4H), 5.60 (d, J=15.5 Hz, 0.4H), 5.38 (s, 0.6H), 5.26 (d, J=15.5 Hz, 0.6H), 4.90 (d, J=15.5 Hz, 0.4H), 4.77 (d, J=15.5 Hz, 0.6H). Mass spectrum (LCMS, ESI pos) Calcd. for $C_{29}H_{21}N_3O_4ICl$: 637.0; Found: 638.1(M+H).

Example 61

(4-Chloro-phenyl)-[3-(4-chloro-phenyl)-7-iodo-2,5-dioxo-1,2,3,5-tetrahydro-benzo[e][1,4]diazepin-4-yl]-acetic acid methyl ester $^1$H NMR (400 MHz, CDCl$_3$): δ 8.04 (m, 1.7H), 7.87 (m, 0.3H), 7.50 (s, 1H), 7.42–7.10 (m, 6H), 7.00 (m, 1H), 6.83 (s, 0.8H), 6.73 (d, J=8.4 Hz, 1.2H), 6.44 (d, J=8.4 Hz, 0.8H), 6.37 (d, J=8.4 Hz, 0.2H), 5.34 (m, 0.2H), 5.28 (s, 0.8H), 3.84 (s, 0.6H), 3.83 (s, 2.4H). Mass spectrum (LCMS, ESI pos) Calcd. for $C_{24}H_{17}N_2O_4ICl_2$: 594.0; Found: 594.8(M+H).

Example 62

(4-Chloro-phenyl)-[3-(4-chloro-phenyl)-7-iodo-2,5-dioxo-1,2,3,5-tetrahydro-benzo[e][1,4]diazepin-4-yl]-acetic acid $^1$H NMR (400 MHz, DMSO-d$_6$): δ 10.64 (s, 0.6H), 10.53 (s, 0.4H), 7.81 (s, 1H) 7.73 (s, 0.4H), 7.52–7.15 (m, 4H), 7.07 (d, J=7.9 Hz, 3H), 6.81 (m, 2H), 6.63 (d, J=8.6 Hz, 0.6H), 6.54 (d, J=8.6 Hz, 0.4H), 6.25 (s, 1H), 5.81 (br s, 0.4H), 5.22 (s, 0.6H). Mass spectrum (LCMS, ESI pos) Calcd. for $C_{23}H_{15}N_2O_4ICl_2$: 579.9; Found: 580.8(M+H).

Example 63

[3-(4-Chloro-phenyl)-7-iodo-1-methyl-2,5-dioxo-1,2,3,5-tetrahydro-benzo[e][1,4]diazepin-4-yl]-phenyl-acetic acid $^1$H NMR (400 MHz, DMSO-d$_6$): δ 7.63 (m, 2H), 7.49 (m, 1H), 7.29 (m, 4H), 7.09 (s, 2H), 7.00 (d, J=7.7 Hz, 1H), 6.82 (m, 1H), 6.72 (m, 1H), 6.28 (m, 1H), 5.92 (s, 0.5H) 5.31 (s, 0.5H), 3.12 (s, 3H). Mass spectrum (LCMS, ESI pos) Calcd. for $C_{24}H_{18}N_2O_4ICl$: 560.0; Found: 560.9(M+H).

Example 64

[3-(4-Chloro-phenyl)-7-iodo-2,5-dioxo-1-(3-phenyl-propyl)-1,2,3,5-tetrahydro-benzo[e][1,4]diazepin-4-yl]-phenyl-acetic acid $^1$H NMR (400 MHz, DMSO-d$_6$): δ 7.70 (m, 1H), 7.49 (m, 3H), 7.17 (m, 11H), 6.80 (s, 2H), 6.36 (m, 0.6H), 6.15 (s, 0.4H), 6.01 (s, 0.6H), 5.31 (s, 0.4H), 4.50 (m, 1H), 4.34 (m, 1H), 2.31 (m, 1H), 2.24 (m, 1H), 1.58, (m, 1H), 1.45 (m, 1H). Mass spectrum (LCMS, ESI pos) Calcd. for $C_{32}H_{26}N_2O_4ICl$: 664.1; Found: 665.2(M+H).

Example 65

2-{2-(4-Chloro-phenyl)-2-[3-(4-chloro-phenyl)-7-iodo-2,5-dioxo-1,2,3,5-tetrahydro-benzo[e][1,4]diazepin-4-yl]-acetylamino}-3-methyl-butyric acid $^1$H NMR (400 MHz, DMSO-d$_6$): δ 7.80–7.75 (m, 1H), 7.58–7.40 (m, 5H), 7.17–7.11 (m, 2H), 6.97 (d, J=8.0 Hz, 1H), 6.92 (d, J=8.0 Hz, 1H), 6.67–6.52 (m, 2H), 5.15 (s, 0.5H) 4.94 (s, 0.5H), 4.07–3.95 (m, 1H), 2.05 (s 1H), 0.84 (d, J=6 Hz, 3H), 0.79–0.71 (m, 3H). Mass spectrum (LCMS, ESI pos) Calcd. for $C_{28}H_{24}Cl_2IN_3O_5$: 679.01; Found: 679.69 (M+H).

Example 66

3-[3-(4-Chloro-phenyl)-7-iodo-2,5-dioxo-1,2,3,5-tetrahydro-benzo[e][1,4]diazepin-4-yl]-3-phenyl-propionic acid $^1$H NMR (400 MHz, DMSO-d$_6$): δ 10.90 (s, 0.8H), 10.71 (s, 0.2H), 7.81 (s, 1H) 7.66 (m, 1H), 7.61–7.53 (m, 3H), 7.42–7.27 (m, 4H), 6.99 (d, J=8.8 Hz, 1.6H), 6.61 (d, J=8.7 Hz, 0.4H), 6.50 (m, 2H), 5.24 (s, 1H), 3.18 (m 2H). Mass spectrum (LCMS, ESI pos) Calcd. for $C_{24}H_{18}N_2O_4ICl$: 560.0; Found: 560.9(M+H).

Example 67

2-[3-(4-Chloro-phenyl)-7-iodo-2,5-dioxo-1,2,3,5-tetrahydro-benzo[e][1,4]diazepin-4-yl]-N-methyl-2-phenyl-acetamide $^1$H NMR (400 MHz, CDCl$_3$): δ 8.06 (d, J=2.1 Hz, 0.8H), 8.02 (m, 0.6H), 7.98 (s, 0.6H), 7.50–7.30 (m, 6H), 716–7.07 (m, 4H), 6.50 (m, 1H), 6.34 (d, J=8.4 Hz, 1H), 5.96 (m, 0.5H), 5.61 (s, 0.5H), 2.91 (s, 1.5H), 2.90 (s, 1.5H). Mass spectrum (LCMS, ESI pos) Calcd. for $C_{24}H_{19}N_3O_3ICl$: 559.0; Found: 559.9(M+H).

Example 68

(7-Iodo-2,5-dioxo-3-pyridin-2-yl-1,2,3,5-tetrahydro-benzo[e][1,4]diazepin-4-yl)-phenyl-acetic acid $^1$H NMR (400 MHz, DMSO-d$_6$): δ 10.60 (s, 0.6H), 10.52 (s, 0.4H), 8.56 (m, 0.4H), 8.46 (m, 0.6H), 8.06 (s, 0.4H), 7.85 (m, 1H), 7.76 (dd, J=2.2 Hz, 8.2 Hz, 1H), 7.61 (m, 0.6H), 7.51 (m, 1H), 7.40 (m, 2H), 7.30 (m, 1H), 7.10 (m, 2H), 6.70 (m, 2H), 6.63 (d, J=8.6 Hz, 0.6H), 6.56 (d, J=8.6 Hz, 0.4H), 5.67 (s, 0.4H), 5.58 (s, 0.6H). Mass spectrum (LCMS, ESI pos) Calcd. for C$_{22}$H$_{16}$N$_3$O$_4$I: 513.0; Found: 514.0(M+H).

Example 69

(7-Iodo-2,5-dioxo-3-pyridin-3-yl-1,2,3,5-tetrahydro-benzo[e][1,4]diazepin-4-yl)-phenyl-acetic acid $^1$H NMR (400 MHz, DMSO-d$_6$): δ 10.72 (s, 0.5H), 10.56 (s, 0.5H), 8.33 (m, 1H), 8.35–7.00 (m, 10H), 6.63 (d, J=8.6 Hz, 0.6H), 6.56 (d, J=8.6 Hz, 0.4H), 6.35 (s, 1H), 5.82 (s, 0.4H), 5.30(s, 0.6H). Mass spectrum (LCMS, ESI pos) Calcd. for C$_{22}$H$_{16}$N$_3$O$_4$I: 513.0; Found: 514.1(M+H).

Example 70

(7-Iodo-2,5-dioxo-3-thiophen-3-yl-1,2,3,5-tetrahydro-benzo[e][1,4]diazepin-4-yl)-phenyl-acetic acid $^1$H NMR (400 MHz, DMSO-d$_6$): δ 10.59 (s, 0.9H), 10.43 (s, 0.1H), 7.78 (s, 1H), 7.54 (m, 3H), 7.35 (m, 4H), 715 (m, 1H), 6.72 (m, 1H), 6.38 (s, 1H), 6.30 (s, 1H), 5.15 (s, 0.1H), 5.12 (s, 0.9H). Mass spectrum (LCMS, ESI pos) Calcd. for C$_{21}$H$_{15}$N$_2$O$_4$IS: 518.0; Found: 518.9(M+H).

Example 71

[7-Iodo-3-(5-methyl-thiophen-2-yl)-2,5-dioxo-1,2,3,5-tetrahydro-benzo[e][1,4]diazepin-4-yl]-phenyl-acetic acid $^1$H NMR (400 MHz, DMSO-d$_6$): δ 10.56 (s, 1H), 7.83 (s, 1H), 7.61 (m, 1H), 7.45 (m, 2H), 7.33 (m, 3H), 6.76 (d, J=8.6 Hz, 1H), 6.33 (s, 1H), 6.23 (m, 1H), 6.02 (s, 1H), 5.24 (s, 1H), 2.11 (s, 3H). Mass spectrum (LCMS, ESI pos) Calcd. for C$_{22}$H$_{17}$N$_2$O$_4$IS: 532.0; Found: 532.9(M+H).

Example 72

[7-Iodo-3-(3-methyl-thiophen-2-yl)-2,5-dioxo-1,2,3,5-tetrahydro-benzo[e][1,4]diazepin-4-yl]-phenyl-acetic acid $^1$H NMR (400 MHz, DMSO-d$_6$): δ 10.54 (s, 1H), 7.99 (s, 1H), 7.68 (m, 1H), 7.34 (m, 4H), 7.00 (m, 1H), 6.77 (m, 1H), 6.39 (m, 1H), 6.27 (s, 1H), 6.02 (s, 1H), 5.36 (s, 1H), 1.69 (s, 3H). Mass spectrum (LCMS, ESI pos) Calcd. for C$_{22}$H$_{17}$N$_2$O$_4$IS: 532.0; Found: 532.8(M+H).

Example 73

[3-(4-Bromo-thiophen-2-yl)-7-iodo-2,5-dioxo-1,2,3,5-tetrahydro-benzo[e][1,4]diazepin-4-yl]-phenyl-acetic acid $^1$H NMR (400 MHz, DMSO-d$_6$): δ 10.71 (s, 0.7H), 10.57 (s, 0.3H), 7.83 (d, J=2.2 Hz, 0.7H), 7.77 (d, J=2.2 Hz, 0.3H), 7.65 (m, 1H), 7.47 (d, J=7.0 Hz, 2H), 7.33 (m, 4H), 7.00 (m, 1H), 6.78 (d, J=8.6 Hz, 0.7H), 6.68 (d, J=8.6 Hz, 0.3H), 6.36 (s, 0.7H), 6.24 (s, 0.3H), 5.87 (s, 0.3H), 5.32 (s, 0.7H). Mass spectrum (LCMS, ESI pos) Calcd. for C$_{21}$H$_{14}$N$_2$O$_4$ISBr: 595.9; Found: 596.8(M+H).

Example 74

(3-[2,2']Bithiophenyl-5-yl-7-iodo-2,5-dioxo-1,2,3,5-tetrahydro-benzo[e][1,4]diazepin-4-yl)-phenyl-acetic acid $^1$H NMR (400 MHz, DMSO-d$_6$): δ 10.73 (s, 0.8H), 10.57 (s, 0.2H), 7.86 (d, J=2.0 Hz, 0.8H), 7.79 (d, J=2.0 Hz, 0.2H), 7.63 (m, 1H), 7.52 (d, J=7.4 Hz, 2H), 7.39 (m, 5H), 7.01 (m, 1H), 6.79 (m, 2H), 6.40 (s, 1H), 6.27 (m, 1H), 5.88 (s, 0.2H), 5.30 (s, 0.8H). Mass spectrum (LCMS, ESI pos) Calcd. for C$_{25}$H$_{17}$N$_2$O$_4$IS$_2$: 600.0; Found: 601.9(M+H).

Example 75

[7-Iodo-3-(3-methyl-benzo[b]thiophen-2-yl)-2,5-dioxo-1,2,3,5-tetrahydro-benzo[e][1,4]diazepin-4-yl]-phenyl-acetic acid $^1$H NMR (400 MHz, DMSO-d$_6$): δ 10.74 (s, 0.5H), 10.56 (s, 0.5H), 8.00 (s, 1H), 7.69 (m, 2H), 7.46 (m, 2H), 7.26 (m, 4H), 6.94 (m, 1H), 6.77 (m, 1H), 6.70 (s, 0.5H), 6.63 (d, J=8.6 Hz, 1H), 6.28 (s, 0.5H), 5.60 (s, 0.5H), 5.48 (s, 0.5H), 1.90 (s, 3H). Mass spectrum (LCMS, ESI pos) Calcd. for C$_{26}$H$_{19}$N$_2$O$_4$IS: 582.0; Found: 583.9(M+H).

Example 76

{3-[5-(2-Chloro-phenyl)-furan-2-yl]-7-iodo-2,5-dioxo-1,2,3,5-tetrahydro-benzo[e][1,4]diazepin-4-yl}-phenyl-acetic acid $^1$H NMR (400 MHz, DMSO-d$_6$): δ 10.70 (s, 0.8H), 10.59 (s, 0.2H), 7.90 (d, J=2.1 Hz, 1H), 7.70 (dd, J=2.1 Hz, 8.3 Hz, 2H), 7.37 (m, 5H), 6.85 (m, 4H), 6.67 (d, J=3.5 Hz 1H), 6.41 (s, 1H), 5.62 (s, 1H), 5.32 (s, 1H.). Mass spectrum (LCMS, ESI pos) Calcd. for C$_{27}$H$_{18}$N$_2$O$_5$ICl: 612.0; Found: 613.1 (M+H).

Example 77

{3-[5-(3-Chloro-phenyl)-furan-2-yl]-7-iodo-2,5-dioxo-1,2,3,5-tetrahydro-benzo[e][1,4]diazepin-4-yl}-phenyl-acetic acid $^1$H NMR (400 MHz, DMSO-d$_6$): δ 10.70 (s, 1H), 7.91 (d, J=2.3 Hz, 2H), 7.68 (dd, J=2.1 Hz, 8.3 Hz, 2H), 7.49 (d, J=7.2 Hz, 2H), 7.30 (m, 5H), 6.89 (d, J=8.6 Hz, 1H), 6.63 (d, J=3.5 Hz, 1H), 6.44 (s, 1H), 5.49 (s, 1H), 5.35 (s, 1H.). Mass spectrum (LCMS, ESI pos) Calcd. for C$_{27}$H$_{18}$N$_2$O$_5$ICl: 612.0; Found: 612.9(M+H).

Example 78

(7-Iodo-2,5-dioxo-3-quinolin-3-yl-1,2,3,5-tetrahydro-benzo[e][1,4]diazepin-4-yl)-phenyl-acetic acid $^1$H NMR (400 MHz, DMSO-d$_6$): δ 10.72 (s, 0.8H), 10.61 (s, 0.2H), 9.02 (d, J=2.0 Hz, 1.5H), 8.82 (d, J=2.0 Hz, 0.5H), 8.45 (s, 1.5H), 8.36 (s, 0.5H), 8.05 (d, J=8.5 Hz, 1.5H), 7.98 (d, J=8.5 Hz, 0.5H), 7.84–6.84 (m, 7H), 6.72 (s, 0.8H), 6.62 (d, J=8.6 Hz, 0.8H), 6.56 (d, J=8.6 Hz, 0.2H), 6.45 (s, 0.2H), 5.68 (s, 0.2H), 5.10 (s, 0.8H.). Mass spectrum (LCMS, ESI pos) Calcd. for $C_{26}H_{18}N_3O_4I$: 563.0; Found: 564.1(M+H).

Example 79

[7-Bromo-3-(4-chloro-phenyl)-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): δ 10.79 (s, 0.5H), 10.63 (s, 0.5H), 7.58 (m, 1H) 7.52 (d, J=8.6 Hz 1H), 7.41 (m, 4H), 7.17 (m, 3H), 6.98 (m, 1H), 6.79 (d, J=8.6 Hz, 0.5H), 6.72 (d, J=8.6 Hz, 0.5H), 6.29 (s, 0.5H), 6.24 (s, 0.5H), 5.68 (s, 0.5H), 5.23 (s, 0.5H). Mass spectrum (LCMS, ESI pos) Calcd. for $C_{23}H_{15}N_2O_4BrCl_2$: 534.0; Found: 534.9(M+H).

Example 80

2-[7-Bromo-3-(4-chloro-phenyl)-2,5-dioxo-1,2,3,5-tetrahydro-benzo[e][1,4]diazepin-4-yl]-3-(4-trifluoromethyl-phenyl)-propionic acid $^1$H NMR (400 MHz, DMSO-d$_6$): δ 10.77 (s, 0.8H), 10.51 (s, 0.2H), 7.30–7.20 (m, 6H), 7.35 (m, 1H), 7.15 (m, 3H), 6.96 (m, 2H), 6.72 (m, 1H), 5.60 (br s, 2H). Mass spectrum (LCMS, ESI pos) Calcd. for $C_{25}H_{17}N_2O_4BrF_3Cl$: 580.0; Found: 581.0(M+H).

Example 81

2-[7-Bromo-3-(4-chloro-phenyl)-2,5-dioxo-1,2,3,5-tetrahydro-benzo[e][1,4]diazepin-4-yl]-3-phenyl-propionic acid $^1$H NMR (400 MHz, DMSO-d$_6$): δ 10.81 (s, 0.8H), 10.56 (s, 0.2H), 7.48 (s, 1H) 7.42–7.30 (m, 4H), 7.22 (m, 3H), 7.13 (m, 2H), 6.95 (m, 1H), 6.69 (m, 1H), 5.54(m, 1.4H), 5.40 (s, 0.3H), 5.30 (br s, 0.3H), 3.40 (m, 1.5H), 3.20 (m, 0.5H). Mass spectrum (LCMS, ESI pos) Calcd. for $C_{24}H_{18}N_2O_4BrCl$: 512.0; Found: 513.0(M+H).

Example 82

2-[7-Bromo-3-(4-chloro-phenyl)-2,5-dioxo-1,2,3,5-tetrahydro-benzo[e][1,4]diazepin-4-yl]-3-(4-chloro-phenyl)-propionic acid $^1$H NMR (400 MHz, DMSO-d$_6$): δ 10.80 (s, 0.8H), 10.58 (s, 0.2H), 7.50 (s, 1H), 7.43–7.37 (m, 3H), 7.22–7.12 (m, 4H), 6.92 (m, 2H), 6.69 (m, 1H), 5.57(m, 0.8H), 5.53 (s, 0.8H), 5.37 (s, 0.2H), 5.16 (br s, 0.2H), 3.40 (m, 1.5H), 3.20 (m, 0.5H). Mass spectrum (LCMS, ESI pos) Calcd. for $C_{24}H_{17}N_2O_4BrCl_2$: 546.0; Found: 547.0 (M+H).

Example 83

2-(4-Chloro-phenyl)-2-[3-(4-chloro-phenyl)-7-iodo-2,5-dioxo-1,2,3,5-tetrahydro-benzo[e][1,4]diazepin-4-yl]-acetamide $^1$H NMR (400 MHz, DMSO-d$_6$): δ 10.75 (s, 0.6H), 10.65 (s, 0.4H), 7.77 (m, 1H), 7.71 (m, 1H), 7.56 (m, 1H), 7.52–7.45 (m, 3H), 7.38–7.07 (m, 4H), 6.91 (d, J=8.4 Hz, 1H), 6.64–6.55 (m, 1H), 6.41 (s, 0.6H), 5.51 (s, 0.4H), 4.96 (s, 0.6H), 4.70 (s, 0.4H). Mass spectrum (LCMS, ESI pos) Calcd. for $C_{23}H_{16}N_3O_3ICl_2$: 579.0; Found: 580.1(M+H).

Example 84

[7-Chloro-3-(4-chloro-phenyl)-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): δ 10.77 (s, 0.8H), 10.61 (s, 0.2H), 7.52 (m, 1H) 7.46–7.39 (m, 4H), 7.32 (m, 2H), 7.15 (d, J=9.0 Hz, 2H), 6.97 (m, 1H), 6.86 (d, J=8.4 Hz, 0.6H), 6.78 (d, J=8.4 Hz, 0.4H), 6.28 (s, 0.4H), 6.23 (s, 0.6H), 5.72 (br s, 0.4H), 5.23 (s, 0.6H). Mass spectrum (LCMS, ESI pos) Calcd. for $C_{23}H_{15}N_2O_4Cl_3$: 488.0; Found: 489.0(M+H).

Example 85

(4-Chloro-phenyl)-[3-(4-chloro-phenyl)-7-methyl-2,5-dioxo-1,2,3,5-tetrahydro-benzo[e][1,4]diazepin-4-yl]-acetic acid $^1$H NMR (400 MHz, DMSO-d$_6$): δ 10.53 (s, 0.6H), 10.37 (s, 0.4H), 7.50 (d, J=8.4 Hz, 1H), 7.41–7.29 (m, 4H), 7.17–7.00 (m, 4H), 6.91 (m, 1H), 6.72 (d, J=8.4 Hz, 0.6H), 6.64 (d, J=8.4 Hz, 0.4H), 6.34 (s, 0.4H), 6.25 (s, 0.6H), 5.71 (s, 0.4H), 5.25 (s, 0.6H), 2.14 (s, 2H), 2.12 (s, 1H). Mass spectrum (LCMS, ESI pos) Calcd. for $C_{24}H_{18}N_2O_4Cl_2$: 468.1; Found: 469.0(M+H).

Example 86

(4-Chloro-phenyl)-[3-(4-chloro-phenyl)-2,5-dioxo-1,2,3,5-tetrahydro-naphtho[2,3-e][1,4]diazepin-4-yl]-acetic acid $^1$H NMR (400 MHz, DMSO-d$_6$): δ 10.79 (s, 0.6H), 10.64 (s, 0.4H), 8.21 (s, 0.6H), 8.17 (s, 0.4H), 7.88 (m, 3H), 7.69 (m, 1H), 7.55 (d, J=8.4 Hz, 1H), 7.49–7.39 (m, 4H), 7.29 (s, 1H), 7.21 (m, 1H), 7.01 (m, 2H), 6.41 (s, 0.4H), 632 (s, 0.6H), 5.81 (s, 0.4H), 5.32 (s, 0.6H). Mass spectrum (LCMS, ESI pos) Calcd. for $C_{27}H_{18}N_2O_4Cl_2$: 504.1; Found: 505.0 (M+H).

Example 87

[8-Chloro-3-(4-chloro-phenyl)-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): δ 10.73 (s, 0.8H), 10.58 (s, 0.2H), 7.52 (m, 2H), 7.40 (m, 1H), 7.14 (m, 4H), 7.00 (m, 1H), 6.91 (m, 3H), 6.30 (s 0.2H), 6.25 (s, 0.8H) 5.76 (s, 0.2H), 5.22 (s, 0.8H). Mass spectrum (LCMS, ESI pos) Calcd. for $C_{23}H_{15}N_2O_4Cl_3$: 488.0; Found: 489.0(M+H).

Example 88

(4-Chloro-phenyl)-[3-(4-chloro-phenyl)-7-ethynyl-2,5-dioxo-1,2,3,5-tetrahydro-benzo[e][1,4]diazepin-4-yl]-acetic acid $^1$H NMR (400 MHz, DMSO-d$_6$): δ 10.83 (s, 0.5H), 10.66 (s, 0.5H), 7.52 (m, 2H) 7.43–7.29 (m, 4H), 7.15 (m, 3H), 6.96 (m, 1H), 6.83 (d, J=8.4 Hz, 0.6H), 6.75 (d, J=8.4 Hz, 0.4H), 6.29 (s, 0.4H), 6.23 (s, 0.6H), 5.74 (br s, 0.4H), 5.21 (s, 0.6H), 4.16 (s, 0.6H), 4.14 (s, 0.4H). Mass spectrum (LCMS, ESI pos) Calcd. for $C_{23}H_{16}N_2O_4ICl_2$: 478.0; Found: 479.0(M+H).

Example 89

[3-(4-Chloro-phenyl)-7-iodo-2,5-dioxo-1,2,3,5-tetrahydro-benzo[e][1,4]diazepin-4-yl]-p-tolyl-acetic acid $^1$H NMR (400 MHz, DMSO-d$_6$): δ 10.64 (s, 0.8H), 10.46 (s, 0.2H), 7.81 (s, 1H), 7.50 (m, 2H), 7.36 (d, J=7.9 Hz, 2H), 7.20 (m, 1H), 7.08 (m, 3H), 6.81 (d, J=8.4 Hz, 1H), 6.63 (d, J=8.6 Hz, 1H), 6.27 (s, 1H), 5.83 (br s, 0.2H), 5.16 (s, 0.8H), 2.22 (s, 3H). Mass spectrum (LCMS, ESI pos) Calcd. for C$_{24}$H$_{18}$N$_2$O$_4$ICl: 560.0; Found: 561.0(M+H).

Example 90

(4-Chloro-3-fluoro-phenyl)-[3-(4-chloro-phenyl)-7-iodo-2,5-dioxo-1,2,3,5-tetrahydro-benzo[e][1,4]diazepin-4-yl]-acetic acid $^1$H NMR (400 MHz, DMSO-d$_6$): δ 10.65 (s, 0.9H), 10.60 (s, 0.1H), 7.79 (s, 1H), 7.52 (m, 3H), 7.35 (m, 2H), 7.13 (m, 2H), 6.95 (d, J=8.0 Hz, 1H), 6.63 (d, J=8.6 Hz, 1H), 6.29 (s, 0.1H), 6.14 (s, 0.9H), 5.80 (s, 0.1H), 5.29 (s, 0.9H). Mass spectrum (LCMS, ESI pos) Calcd. for C$_{23}$H$_{14}$N$_2$O$_4$ICl$_2$F: 597.9; Found: 598.9(M+H).

Example 91

[3-(4-Chloro-phenyl)-7-iodo-2,5-dioxo-1,2,3,5-tetrahydro-benzo[e][1,4]diazepin-4-yl]-(2-fluoro-4-trifluoromethyl-phenyl)-acetic acid $^1$H NMR (400 MHz, DMSO-d$_6$): δ 10.65 (br s, 1H), 7.80 (s, 1H), 7.74–7.53 (m, 5H), 7.12 (d, J=8.8 Hz, 2H), 6.85 (d, J=8.1 Hz, 1H), 6.63 (d, J=8.6 Hz, 1H), 6.45 (s, 1H), 5.60 (s, 0.1H), 5.24 (s, 0.9H). Mass spectrum (LCMS, ESI pos) Calcd. for C$_{24}$H$_{14}$N$_2$O$_4$IClF$_4$: 632.0; Found: 633.0(M+H).

Example 92

(4-Chloro-phenyl)-[3-(4-chloro-phenyl)-7-ethyl-2,5-dioxo-1,2,3,5-tetrahydro-benzo[e][1,4]diazepin-4-yl]-acetic acid $^1$H NMR (400 MHz, DMSO-d$_6$): δ 10.50 (s, 0.8H), 10.32 (s, 0.2H), 7.52 (d, J=8.4 Hz, 1H), 7.36 (m, 3H), 7.17–7.03 (m, 4H), 6.83 (d, J=8.0 Hz, 1H), 6.63 (d, J=8.6 Hz, 1H), 6.72 (d, J=8.4 Hz, 1H), 6.37 (s, 0.2H), 6.29 (m, 0.8H), 5.74 (s, 0.2H), 5.26 (s, 0.8H), 2.42 (m, 2H), 1.00 (m, 3H). Mass spectrum (LCMS, ESI pos) Calcd. for C$_{25}$H$_{20}$N$_2$O$_4$Cl$_2$: 482.1; Found: 483.1(M+H).

Example 93

(4-Chloro-phenyl)-[3-(4-chloro-phenyl)-7-isopropyl-2,5-dioxo-1,2,3,5-tetrahydro-benzo[e][1,4]diazepin-4-yl]-acetic acid $^1$H NMR (400 MHz, DMSO-d$_6$): δ 10.49 (s, 0.8H), 10.27 (s, 0.2H), 7.53 (d, J=8.4 Hz, 1H) 7.36 (m, 2H), 7.17–7.03 (m, 3H), 6.98 (d, J=8.4 Hz, 1H), 6.78 (d, J=8.1 Hz, 1H), 6.72 (d, J=8.4 Hz, 1H), 6.38 (s, 0.2H), 6.31 (m, 0.8H), 5.76 (s, 0.2H), 5.29 (s, 0.8H), 2.72 (m, 1H), 1.02 (m, 6H). Mass spectrum (LCMS, ESI pos) Calcd. for C$_{25}$H$_2$O$_4$N$_2$O$_4$Cl$_2$: 496.1; Found: 497.1(M+H).

Example 94

[7-tert-Butyl-3-(4-chloro-phenyl)-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): δ 10.45 (s, 0.8H), 10.25 (s, 0.2H), 7.52 (d, J=8.4 Hz, 1H), 7.44 (m, 1H), 7.40–7.31 (m, 3H), 7.22–7.03 (m, 3H), 6.98 (d, J=8.6 Hz, 1H), 6.78 (d, J=8.4 Hz, 1H), 6.72 (d, J=8.6 Hz, 1H), 6.37 (s, 0.2H), 6.29 (m, 0.8H), 5.75 (s, 0.2H), 5.27 (s, 0.8H), 1.13 (s, 8H), 1.11 (s, 1H). Mass spectrum (LCMS, ESI pos) Calcd. for C$_{27}$H$_{24}$N$_2$O$_4$Cl$_2$: 510.1; Found: 511.1(M+H).

Example 95

[3-(4-Chloro-phenyl)-7-ethyl-2,5-dioxo-1,2,3,5-tetrahydro-benzo[e][1,4]diazepin-4-yl]-phenyl-acetic acid $^1$H NMR (400 MHz, DMSO-d$_6$): δ 10.58 (s, 1H), 7.48 (d, J=7.0 Hz, 1H), 7.35 (m, 6H), 7.09 (d, J=8.6 Hz, 2H), 6.92 (d, J=8.1 Hz, 2H), 6.74 (d, J=8.1 Hz, 1H), 6.32 (s, 1H), 5.12 (s, 1H), 2.43 (q, J=7.7 Hz, 2H), 1.00 (t, J=7.5 Hz, 3H). Mass spectrum (LCMS, ESI pos) Calcd. for C$_{25}$H$_{21}$N$_2$O$_4$Cl$_2$: 448.1; Found: 449.1(M+H).

Example 96

[3-(4-Chloro-phenyl)-7-isopropyl-2,5-dioxo-1,2,3,5-tetrahydro-benzo[e][1,4]diazepin-4-yl]-phenyl-acetic acid $^1$H NMR (400 MHz, DMSO-d$_6$): δ 10.55 (s, 1H), 7.48 (d, J=7.0 Hz, 2H), 7.35(m, 3H), 7.07 (m, 3H), 6.91 (d, J=8.4 Hz, 2H), 6.73 (d, J=8.4 Hz, 2H), 6.31 (s, 1H), 5.11 (s, 1H), 2.74 (m, 1H), 1.03 (d, J=7.0 Hz, 6H). Mass spectrum (LCMS, ESI pos) Calcd. for C$_{26}$H$_{23}$N$_2$O$_4$Cl: 462.1; Found: 463.1(M+H).

Example 97

[7-tert-Butyl-3-(4-chloro-phenyl)-2,5-dioxo-1,2,3,5-tetrahydro-benzo[e][1,4]diazepin-4-yl]-phenyl-acetic acid $^1$H NMR (400 MHz, DMSO-d$_6$): δ 10.54 (s, 1H), 7.50 (d, J=7.0 Hz, 2H), 7.37 (m, 3H), 7.24 (dd, J=2.4, 8.6 Hz, 2H), 7.06 (d, J=8.6 Hz, 2H), 6.90 (d, J=7.9 Hz, 2H), 6.72 (d, J=8.6 Hz, 1H), 6.32 (s, 1H), 5.10 (m, 1H), 1.13 (s, 9H). Mass spectrum (LCMS, ESI pos) Calcd. for C$_{27}$H$_{25}$N$_2$O$_4$Cl$_2$: 476.2; Found: 477.1(M+H).

Example 98

[7-sec-Butyl-3-(4-chloro-phenyl)-2,5-dioxo-1,2,3,5-tetrahydro-benzo[e][1,4]diazepin-4-yl]-phenyl-acetic acid $^1$H NMR (400 MHz, DMSO-d$_6$): δ 10.51 (s, 1H), 7.49 (d, J=7.0 Hz, 2H), 7.36 (m, 4H), 7.20 (m, 1H), 7.03 (m, 3H), 6.86 (m, 1H), 6.73 (m, 1H), 6.31 (s, 1H), 5.11 (s, 1H), 2.45 (m, 1H), 1.44 (m, 1H), 1.28 (m, 1H), 1.06 (m, 3H), 0.45 (m, 3H). Mass spectrum (LCMS, ESI pos) Calcd. for C$_{27}$H$_{25}$N$_2$O$_4$Cl: 476.2; Found: 477.1(M+H).

Example 99

[7-sec-Butyl-3-(4-chloro-phenyl)-2,5-dioxo-1,2,3,5-tetrahydro-benzo[e][1,4]diazepin-4-yl]-(4-chloro-phenyl)-acetic acid $^1$H NMR (400 MHz, DMSO-$d_6$): δ 10.54 (s, 1H), 7.53 (d, J=8.6 Hz, 2H), 7.44 (m, 3H), 7.21–6.99 (m, 5H), 6.71 (m, 1H), 6.19 (s, 1H), 5.23 (s, 1H), 2.44 (m, 1H), 1.45 (m, 1H), 1.29 (m, 1H), 1.05 (m, 3H), 0.45 (m, 3H). Mass spectrum (LCMS, ESI pos) Calcd. for $C_{27}H_{24}N_2O_4Cl_2$: 510.1; Found: 511.1(M+H).

Example 100

(4-Bromo-phenyl)-[3-(4-chloro-phenyl)-7-isopropyl-2,5-dioxo-1,2,3,5-tetrahydro-benzo[e][1,4]diazepin-4-yl]-acetic acid $^1$H NMR (400 MHz, DMSO-$d_6$): δ 10.53 (s, 0.7H), 10.34 (s, 0.3H), 7.54 (m, 2H), 7.46 (d, J=8.6 Hz, 2H), 7.36–7.24 (m, 2H), 7.09 (m, 3H), 6.96 (m, 1H), 6.72 (d, J=8.4 Hz, 0.7H), 6.64 (d, J=8.4 Hz, 0.3H), 6.30 (s, 0.3H), 6.17 (s, 0.7H), 5.65 (s, 0.3H), 5.24 (s, 0.7H), 2.72 (m, 1H), 1.03 (m, 6H). Mass spectrum (LCMS, ESI pos) Calcd. for $C_{26}H_{22}N_2O_4ClBr$: 540.0; Found: 541.0(M+H).

Example 101

[3-(4-Bromo-phenyl)-7-isopropyl-2,5-dioxo-1,2,3,5-tetrahydro-benzo[e][1,4]diazepin-4-yl]-(4-chloro-phenyl)-acetic acid $^1$H NMR (400 MHz, DMSO-$d_6$): δ 10.52 (s, 0.7H), 10.34 (s, 0.3H), 7.52 (d, J=8.4 Hz, 1H), 7.41 (m, 3H), 7.28–7.21 (m, 3H), 7.12–7.03 (m, 2H), 6.91 (m, 1H), 6.72 (d, J=8.6 Hz, 0.7H), 6.64 (d, J=8.6 Hz, 0.3H), 6.30 (s, 0.3H), 6.17 (s, 0.7H), 5.65 (s, 0.3H), 5.24 (s, 0.7H), 2.73 (m, 1H), 1.03 (m, 6H). Mass spectrum (LCMS, ESI pos) Calcd. for $C_{26}H_{22}N_2O_4ClBr$: 540.0; Found: 541.0(M+H).

Example 102

(4-Chloro-phenyl)-[3-(4-chloro-phenyl)-7-cyclopropyl-2,5-dioxo-1,2,3,5-tetrahydro-benzo[e][1,4]diazepin-4-yl]-acetic acid $^1$H NMR (400 MHz, DMSO-$d_6$): δ 10.53 (s, 0.7H), 10.35 (s, 0.3H), 7.50 (d, J=8.4 Hz, 1H), 7.39 (m, 2H), 7.21–7.09 (m, 4H), 6.92 (m, 3H), 6.70 (d, J=8.4 Hz, 0.7H), 6.61 (d, J=8.4 Hz, 0.3H), 6.31 (s, 0.3H), 6.22 (s, 0.7H), 5.67 (s, 0.3H), 5.23 (s, 0.7H), 1.80 (m, 1H), 0.86 (m, 2H), 0.5 (m, 1H), 0.42 (m, 1H). Mass spectrum (LCMS, ESI pos) Calcd. for $C_{26}H_{20}N_2O_4Cl_2$: 494.1; Found: 495.0(M+H).

Example 103

[3-(4-Chloro-phenyl)-7-cyclopropyl-2,5-dioxo-1,2,3,5-tetrahydro-benzo[e][1,4]diazepin-4-yl]-phenyl-acetic acid $^1$H NMR (400 MHz, DMSO-$d_6$): δ 10.51 (s, 0.7H), 10.30 (s, 0.3H), 7.47 (d, J=7.0 Hz, 2H), 7.38–7.08 (m, 5H), 7.04 (d, J=8.6 Hz, 2H), 6.88 (m, 2H), 6.70 (d, J=8.4 Hz, 0.7H), 6.61 (d, J=8.4 Hz, 0.3H), 6.34 (br s, 1H), 5.71 (s, 0.3H), 5.16 (s, 0.7H), 1.79 (m, 1H), 0.85 (m, 2H), 0.53 (m, 1H), 0.44 (m, 1H). Mass spectrum (LCMS, ESI pos) Calcd. for $C_{26}H_{21}N_2O_4Cl$: 460.1; Found: 461.1(M+H).

Example 104

[3-(4-Chloro-3-fluoro-phenyl)-7-iodo-2,5-dioxo-1,2,3,5-tetrahydro-benzo[e][1,4]diazepin-4-yl]-(4-chloro-phenyl)-acetic acid $^1$H NMR (400 MHz, DMSO-$d_6$): δ 10.56 (s, 0.9H), 10.36 (s, 0.1H), 7.50 (m, 3H), 7.34 (m, 2H), 7.17 (m, 2H), 7.05–6.80 (m, 3H), 6.37 (s, 1H), 5.19 (s, 1H). Mass spectrum (LCMS, ESI pos) Calcd. for $C_{23}H_{14}N_2O_4Cl_2F$: 597.9; Found: 598.9(M+H).

Example 105

(2,5-Dioxo-3-phenyl-1,2,3,5-tetrahydro-benzo[e][1,4]diazepin-4-yl)-phenyl-acetic acid $^1$H NMR (400 MHz, DMSO-$d_6$): δ 10.79 (s, 0.9H), 10.61 (s, 0.1H), 7.77 (s, 1H), 7.53 (m, 4H), 7.38 (m, 4H), 7.03 (m, 2H), 6.81 (m, 2H), 6.67 (d, J=8.6 Hz, 0.9H), 6.58 (d, J=8.6 Hz, 0.1H), 6.27 (s, 0.1H), 6.16 (s, 0.9H), 5.64 (s, 0.1H), 5.30 (s, 0.9H). Mass spectrum (LCMS, ESI pos) Calcd. for $C_{23}H_{18}N_2O$: 386.1; Found: 387.1(M+H).

Example 106

[3-(4-Chlorophenyl)-7-phenyl-2,5-dioxo-1,2,3,5-tetrahydro-benzo[e][1,4]diazepin-4-yl]-phenylacetic acid $^1$H NMR (400 MHz, DMSO-$d_6$): δ 10.60 (s, 0.8H), 10.50 (s, 0.2H), 7.82 (s, 1H), 7.52 (m, 4H), 7.41 (m, 2H), 7.33 (m, 5H), 7.02 (d, J=8.2 Hz, 2H), 6.91 (d, J=8.3 Hz, 1H), 6.82 (m, 2H), 6.39 (bs, 1H), 5.25 (bs, 1H). Mass spectrum (LCMS, ESI pos.) Calcd. For $C_{29}H_{21}ClN_2O_4$: 496.10. Found: 497.0 (M+H).

Example 107

[3-(4-Chlorophenyl)-7-(4-methylphenyl)-2,5-dioxo-1,2,3,5-tetrahydro-benzo[e][1,4]diazepin-4-yl]-phenylacetic acid $^1$H NMR (400 MHz, DMSO-$d_6$): δ 10.67 (bs, 1H), 7.77 (m, 1H), 7.49 (m, 3H), 7.41 (m, 4H), 7.25 (m, 4H), 7.06 (m, 2H), 6.90 (d, J=8.9 Hz, 2H), 6.39 (bs, 1H), 5.20 (bs 1H), 2.32 (s, 3H). Mass spectrum (LCMS, ESI pos.) Calcd. For $C_{30}H_{23}ClN_2O_4$: 510.10. Found: 511.0 (M+H).

Example 108

[3-(4-Chlorophenyl)-7-(3-methylphenyl)-2,5-dioxo-1,2,3,5-tetrahydro-benzo[e][1,4]diazepin-4-yl]-phenylacetic acid $^1$H NMR (400 MHz, DMSO-$d_6$): δ 10.60 (bs, 1H), 7.92 (m, 1H), 7.63 (m, 2H), 7.43 (m, 4H), 7.29 (m, 5H), 7.16 (m, 1H), 7.04 (m, 1H), 6.89 (m, 2H), 6.53 (bs, 1H), 5.40 (bs, 1H), 2.40 (s, 3H). Mass spectrum (LCMS, ESI pos.) Calcd. For $C_{30}H_{23}ClN_2O_4$: 510.10. Found: 511.0 (M+H).

Example 109

[3-(4-Chlorophenyl)-7-(4-hydroxyphenyl)-2,5-dioxo-1,2,3,5-tetrahydro-benzo[e][1,4]diazepin-4-yl]-phenylacetic acid $^1$H NMR (400 MHz, DMSO-d$_6$): δ 10.73 (bs, 0.85H), 10.56 (s, 0.15H), 9.62 (s, 1H), 7.68 (s, 1H), 7.52 (m, 3H), 7.36 (m, 4H), 7.17 (m, 1H), 7.10 (m, 2H), 6.97 (d, J=7.7 Hz, 2H), 6.87 (d, J=8.5 Hz, 2H), 6.81 (d, J=8.6 Hz, 2H), 6.37 (bs, 1H), 5.14 (bs, 1H), 2.40. Mass spectrum (LCMS, ESI pos.) Calcd. For C$_{29}$H$_{21}$ClN$_2$O$_5$: 512.15. Found: 513.1 (M+H).

Example 110

[3-(4-Chlorophenyl)-7-(4-hydroxycarbonylphenyl)-2,5-dioxo-1,2,3,5-tetrahydro-benzo[e][1,4]diazepin-4-yl]-phenylacetic acid $^1$H NMR (400 MHz, DMSO-d$_6$): δ 13.1 (bs, 1H), 10.80 (bs, 0.4H), 10.59 (s, 0.6H), 7.98 (d, J=6.5 Hz, 2H), 7.85 (d, J=9.5 Hz, 1H), 7.65 (m, 3H), 7.50 (d, J=8.0 Hz, 1H), 7.34 (m, 4H), 7.24 (d, J=7.2 Hz, 1H), 7.14 (d, J=8.6 Hz, 1H), 7.07 (d, J=7.7 Hz, 1H), 6.94 (m, 1H), 6.37 (d, J=14.8 Hz, 1H), 5.76 (s, 1H). Mass spectrum (LCMS, ESI pos.) Calcd. For C$_{30}$H$_{21}$ClN$_2$O$_6$: 540.16. Found: 541.0 (M+H).

Example 111

(4-Chlorophenyl)-[3-(4-chlorophenyl)-7-iodo-5-oxo-1,2,3,5-tetrahydro-benzo[e][1,4]diazepin-4-yl]acetic acid $^1$H NMR (400 MHz, d$_6$-DMSO): Major (75%): δ 8.25 (d, J=2.2 Hz, 1H), 7.22 (d, J=8.4 Hz, 2H), 7.19 (dd, J=8.8 Hz, J=2.2 Hz, 1H), 7.08 (d, J=8.3 Hz, 2H), 6.99 (d, J=8.4 Hz, 2H), 6.93 (br m, 1H), 6.77 (d, J=7.9 Hz, 2H), 6.27 (d, J=8.7 Hz, 1H), 6.15 (br s, 1H), 5.02 (s, 1H), 3.89 (br m, 2H). Minor (25%): 7.97 (d, J=2.1 Hz, 1H), 7.43 (d, J=8.6 Hz, 2H), 7.36 (d, J=8.5 Hz, 1H), 7.14 (d, J=8.4 Hz, 2H), 7.11 (dd, J=8.8 Hz, J=2.2 Hz, 2H), 6.93 (br m, 1H), 6.19 (d, J=8.8 Hz, 1H), 6.15 (br s, 1H), 5.23 (s, 1H), 3.89 (br m, 2H). Mass Spectrum (LCMS, ESI pos.): Calcd. For C$_{23}$H$_{17}$Cl$_2$IN$_2$O$_3$: 565.97; found: 566.94 (M+H).

Example 112

[3-(4-Chlorophenyl)-2,5-dioxo-8-phenyl-1,2,3,5-tetrahydro-benzo[e][1,4]diazepin-4-yl]-phenylacetic acid $^1$H NMR (400 MHz, d$_6$-DMSO): δ 10.41 (s, 1H), 7.73–7.61 (m, 1H), 7.57–7.32 (m, 8H), 7.28–7.02 (m, 5H), 6.98 (d, J=8.7 Hz, 1H), 6.72 (d, J=7.8 Hz, 1H), 6.32 (s, 1H), 5.29 (s, 1H). Mass Spectrum (LCMS, ESI pos.): Calcd. for C$_{29}$H$_{21}$ClN$_2$O$_4$: 496.12; found: 497.12 (M+H).

Example 113

[7-Benzo[1,3]dioxol-5-yl-2,5-dioxo-3-(4-trifluoromethyl-phenyl)-1,2,3,5-tetrahydro-benzo[e][1,4]diazepin-4-yl]-phenylacetic acid $^1$H NMR (400 MHz, d$_6$-DMSO): Major (67%): δ 10.84 (s, 1H), 7.65 (d, J=2.1 Hz, 1H), 7.56–7.34 (m, 9H), 7.23 (d, J=8.1 Hz, 1H), 7.05 (s, 1H), 6.99–6.93 (m, 2H), 6.86 (d, J=8.5 Hz, 1H), 6.37 (s, 1H), 5.20 (s, 1H). Minor (33%): 10.69 (s, 1H), 7.70 (d, J=2.1 Hz, 1H), 7.56–7.34 (m, 9H), 7.23 (d, J=8.1 Hz, 1H), 7.09 (s, 1H), 6.99–6.93 (m, 2H), 6.81 (d, J=8.3 Hz, 1H), 6.34 (s, 1H), 5.40 (s, 1H). Mass Spectrum (LCMS, ESI pos.): Calcd. for C$_{31}$H$_{21}$F$_3$N$_2$O$_6$: 574.14; found: 574.98 (M+H).

Example 114

3-(4-Chloro-phenyl)-3-[3-(4-chloro-phenyl)-7-iodo-5-oxo-1,2,3,5-tetrahydro-benzo[e][1,4]diazepin-4-yl]-propionic acid $^1$H NMR (400 MHz, DMSO-d$_6$): δ 8.17 (d, J=2.0 Hz, 1H), 7.33 (d, J=8.8 Hz, 2H), 7.19–6.96 (m, 4H), 6.75 (d, J=8.8 Hz, 1H), 6.39–6.29 (m, 1H), 6.21 (d, J=8.8 Hz, 1H), 4.92 (d, J=5.2 Hz, 1H), 4.08–3.96 (m, 1H), 3.46–3.36 (m, 2H), 2.93–2.75 (m, 2H).

Mass spectrum (LCMS, ESI pos) Calcd. for C$_{24}$H$_{19}$Cl$_2$IN$_2$O$_3$: 579.98; Found 580.8 (M+H).

Example 115

2-[3-(4-Chloro-phenyl)-7-iodo-2,5-dioxo-1,2,3,5-tetrahydro-benzo[e][1,4]diazepin-4-yl]-3-naphthalen-2-yl-propionic acid $^1$H NMR (400 MHz, DMSO-d$_6$): δ 10.77 (s, 0.7H), 10.42 (s, 0.3H), 7.87–7.84 (m, 1.0H), 7.82–7.68 (m, 3.0 Hz), 7.66–7.62 (m, 0.7H), 7.58 (bs, 0.3H), 7.55 (d, J=2.0 Hz, 1.0H), 7.51–7.36 (m, 3.0H), 7.20–7.07 (m, 3.0H), 6.92 (bs, 1.0H), 6.56–6.52 (m, 1.0H), 5.80 (bs, 0.7H), 5.58 (bs, 0.7H), 5.44 (bs, 0.3H), 5.38 (bs, 0.3H) 3.62–3.08 (m, 2.0H). Mass spectrum (LCMS, ESI pos.) Calcd. For C$_{28}$H$_{20}$ClIN$_2$O$_4$: 610.02 Found: 610.94 (M+H).

Example 116

2-[7-Iodo-2,5-dioxo-3-(4-trifluoromethoxy-phenyl)-1,2,3,5-tetrahydro-benzo[e][1,4]diazepin-4-yl]-3-naphthalen-2-yl-propionic acid $^1$H NMR (400 MHz, DMSO-d$_6$): δ 10.77 (s, 0.7H), 10.44 (s, 0.3H), 7.92–7.55 (m, 5.0H), 7.56–7.36 (m, 4.0H), 7.31–7.19 (bs, 1.0H), 7.12–6.96 (m, 2.0H), 6.93–6.82 (m, 1.0H), 6.58–6.46 (m, 1.0H), 5.80 (bs, 0.7H), 5.67–5.57 (m, 0.7H), 5.49 (s, 0.3H), 5.43–5.35 (m, 0.3H), 3.71–3.52 (m, 1.0H), 3.21–3.08 (m, 1.0H). Mass spectrum (LCMS, ESI pos.) Calcd. For C$_{29}$H$_{20}$F$_3$IN$_2$O$_5$: 660.04. Found: 660.98 (M+H).

Example 117

2-[3-(4-Chloro-phenyl)-7-iodo-2,5-dioxo-1,2,3,5-tetrahydro-benzo[e][1,4]diazepin-4-yl]-3-naphthalen-1-yl-propionic acid $^1$H NMR (400 MHz, DMSO-d$_6$): δ 10.94 (s, 0.7H), 10.39 (s, 0.3H), 8.32 (d, J=8.8 Hz, 0.7H), 8.27–8.15 (m, 0.3H), 7.97–7.83 (m, 1.0H), 7.84–7.73 (m, 0.3H), 7.73–7.65 (m, 0.7H), 7.62–7.44 (m, 3.0H), 7.40–7.23 (m, 3.0H), 7.22–7.07 (m, 3.0H), 6.64–6.54 (m, 1.0H), 5.87 (bs, 1.0H), 5.62 (bs, 1.0H), 5.36 (bs, 0.6H), 5.20 (bs, 0.4H), 3.89–3.52 (m, 2.0H). Mass spectrum (LCMS, ESI pos.) Calcd. For C$_{28}$H$_{20}$ClIN$_2$O$_4$: 610.02. Found: 610.92 (M+H).

Example 118

2-[7-Iodo-2,5-dioxo-3-(4-trifluoromethoxy-phenyl)-1,2,3,5-tetrahydro-benzo[e][1,4]diazepin-4-yl]-3-naphthalen-1-yl-propionic acid $^1$H NMR (400 MHz, DMSO-d$_6$): δ 10.94 (s, 0.7H), 10.40 (s, 0.3H), 8.34 (d, J=8.4 Hz, 0.7H), 8.21 (bs, 0.3H), 7.88 (d, J=8.0 Hz, 1.0H), 7.78 (d, J=7.2 Hz, 0.3H), 7.69 (d, J=8.4 Hz, 0.7H), 7.72–7.68 (m, 5.0H), 7.67–7.22 (m, 4.0H), 7.07 (d, J=8.4 Hz, 1.0H), 7.04–7.00 (m, 0.3H), 6.58 (d, J=8.8 Hz, 0.7H), 5.90 (bs, 0.7H), 5.70–5.63 (m, 0.7H), 5.46–5.37 (m, 0.3H), 5.26–5.16 (m, 0.3H), 3.97–3.60 (m, 2.0H). Mass spectrum (LCMS, ESI pos.) Calcd. For C$_{29}$H$_{20}$F$_3$IN$_2$O$_5$: 660.04; Found: 660.99(M+H).

Example 119

[3-(4-Chloro-phenyl)-7-iodo-2,5-dioxo-1,2,3,5-tetrahydro-benzo[e][1,4]diazepin-4-yl]-(4-fluoro-phenyl)-acetic acid $^1$H NMR (400 MHz, DMSO-d$_6$): δ 10.62 (s, 0.6H), 10.50 (s, 0.4H), 7.80 (d, J=2 Hz, 0.6H), 7.72 (d, J=2.4 Hz, 0.4H), 7.58–7.47 (m, 2.0H), 7.44–7.32 (m, 1.0H), 7.25–7.03 (m, 4.0H), 6.87–6.75 (m, 1.0H), 6.64 (d, J=8.4 Hz, 0.6H), 6.55 (d, J=8.4 Hz, 0.4H), 6.29 (d, J=6 Hz, 1.0H), 5.80 (s, 0.6H), 5.76 (s, 0.4H), 5.22 (1.0H). Mass spectrum (LCMS, ESI pos.) Calcd. For C$_{23}$H$_{15}$ClFIN$_2$O$_4$: 563.97; Found: 564.84 (M+H).

Example 120

(4-Fluoro-phenyl)-[7-iodo-2,5-dioxo-3-(4-trifluoromethoxy-phenyl)-1,2,3,5-tetrahydrobenzo[e][1,4]diazepin-4-yl]-acetic acid $^1$H NMR (400 MHz, DMSO-d$_6$): δ 10.63 (s, 0.7H), 10.48 (s, 0.3H), 7.75 (d, J=2 Hz, 0.7H), 7.67 (d, J=2 Hz, 0.3H), 7.59–7.46 (m, 2.3H), 7.43–7.36 (m, 0.7H), 7.29 (d, J=8.4 Hz, 0.7H), 7.16–7.06 (m, 2.3H), 7.03–6.97 (d, J=8.4 Hz, 1.0H), 6.93–6.87 (d, J=8.4 Hz, 1.0H), 6.63 (d, J=8.8 Hz, 0.7H), 6.53 (d, J=8.8 Hz, 0.3H), 6.32 (d, 0.3H), 6.28 (s, 0.7H), 5.83 (s, 1.0H), 5.76 (s, 0.3H), 5.25 (s, 0.7H). Mass spectrum (LCMS, ESI pos.) Calcd. For C$_{24}$H$_{15}$F$_4$IN$_2$O$_5$: 614.00; Found: 614.94(M+H).

Example 121

2-[7-Iodo-2,5-dioxo-3-(4-trifluoromethoxy-phenyl)-1,2,3,5tetrahydrobenzo[e][1,4]diazepin-4-yl]-3-(4-iodo-phenyl)-propionic acid $^1$H NMR (400 MHz, DMSO-d$_6$): δ 10.72 (s, 0.8H), 10.49 (s, 0.2H), 7.68 (s, 0.4H), 7.60–7.49 (m, 2.6H), 7.49–7.43 (m, 0.1H), 7.27–7.20 (m, 3.0H), 7.11–7.04 (m, 3.0H), 7.00 (d, J=8 Hz, 0.2H), 6.53 (d, J=8.8 Hz, 0.8H), 5.73 (s, 1.0H), 5.56–5.45 (m, 0.8H), 5.40 (s, 0.2H), 2.95–2.84 (m, 2.0H). Mass spectrum (LCMS, ESI pos.) Calcd. For C$_{25}$H$_{17}$F$_3$I$_2$N$_2$O$_5$: 735.92. Found: 736.83 (M+H).

Example 122

3-(4-Bromo-phenyl)-2-[7-iodo-2,5-dioxo-3-(4-trifluoromethoxy-phenyl)-1,2,3,5-tetrahydro-benzo[e][1,4]diazepin-4-yl]-propionic acid $^1$H NMR (400 MHz, DMSO-d$_6$): δ 10.70 (s, 0.4H), 10.47 (s, 0.6H), 7.69 (d, J=2 Hz, 0.6H), 7.48 (d, J=2 Hz, 0.4H), 7.51–7.43 (m, 1.0H), 7.39–7.33 (m, 2.0H), 7.29–7.12 (m, 3.0H), 7.09–6.99 (m, 2.0H), 6.60–6.50 (m, 1.0H), 5.76 (s, 1.0H), 5.53 (bs, 0.6H), 5.39 (s, 0.4H), 5.10 (bs, 1.0H), 3.17 (d, J=5.12 Hz, 2.0H). Mass spectrum (LCMS, ESI pos.) Calcd. For C$_{25}$H$_{17}$BrF$_3$IN$_2$O$_5$: 687.93. Found: 688.80 (M+H).

Example 123

3-(4-Bromo-phenyl)-2-[3-(4-chloro-phenyl)-7-iodo-2,5-dioxo-1,2,3,5-tetrahydro-benzo[e][1,4]diazepin-4-yl]-propionic acid $^1$H NMR (400 MHz, DMSO-d$_6$): δ 10.73 (s, 0.6H), 10.50 (s, 0.4H), 7.73 (d, J=2 Hz, 0.4H), 7.60 (d, J=2 Hz, 0.6H), 7.55–7.45 (m, 1.0H), 7.41–7.32 (m, 2.0H), 7.25–7.03 (m, 6.0H), 6.55 (d, J=8.4 Hz, 1.0H), 5.70 (s, 0.6H), 5.55–5.46 (m, 0.6H), 5.35 (s, 0.4H), 5.10 (bs, 0.4H), 3.20–2.84 (m, 2.0H). Mass spectrum (LCMS, ESI pos.) Calcd. For C$_{24}$H$_{17}$BrClIN$_2$O$_4$: 637.91. Found: 638.82(M+H).

Example 124

2-[7-Iodo-2,5-dioxo-3-(4-trifluoromethoxy-phenyl)-1,2,3,5-tetrahydro-benzo[e][1,4]diazepin-4-yl]-3-thiophen-2-yl-propionic acid $^1$H NMR (400 MHz, DMSO-d$_6$): δ 10.83 (s, 0.7H), 10.59 (s, 0.3H), 7.73 (bs, 0.3H), 7.70–7.66 (m, 0.7H), 7.60–7.55 (m, 0.3H), 7.51 (dd, J=2.0 Hz, 8.0 Hz, 0.7H), 7.32 (d, J=5.2 Hz, 0.3H), 7.30–7.25 (m, 1.7H), 7.19–7.04 (m, 4.0H), 6.92–6.84 (m, 2.0H), 5.69 (s, 0.7H), 5.48–5.41 (m, 1.0H), 5.19 (bs, 0.3H), 3.56–3.15 (m, 2.0H). Mass spectrum (LCMS, ESI pos.) Calcd. For C$_{23}$H$_{16}$F$_3$IN$_2$O$_5$S: 615.98. Found: 616.75 (M+H).

Example 125

[3-(4-Chloro-phenyl)-7-iodo-2,5-dioxo-1,2,3,5-tetrahydro-benzo[e][1,4]diazepin-4-yl]-(4-trifluoromethyl-phenyl)-acetic acid $^1$H NMR (400 MHz, DMSO-d$_6$): δ 10.61 (s, 0.6H), 10.58 (s, 0.4H), 7.80 (d, J=2.4 Hz, 0.6H), 7.73 (d, J=2.0 Hz, 0.4H), 7.72–7.62 (m, 3.0H), 7.58–7.50 (m, 2.0H), 7.18 (s, 2.0H), 7.06 (d, J=8.4 Hz, 1.0H), 6.88–6.82 (m, 1.0H), 6.63 (d, J=8.4 Hz, 0.6H), 6.53 (d, J=8.4 Hz, 0.4H), 6.37 (s, 0.4H), 6.27 (s, 0.6H), 5.76 (s, 0.4H), 5.28 (s, 0.6H). Mass spectrum (LCMS, ESI pos.) Calcd. For C$_{24}$H$_{15}$ClF$_3$N$_2$O$_4$: 613.97. Found: 614.86 (M+H).

Example 126

2-[3-(4-Chloro-phenyl)-7-iodo-2,5-dioxo-1,2,3,5-tetrahydro-benzo[e][1,4]diazepin-4-yl]-3-thiophen-2-yl-propionic acid $^1$H NMR (400 MHz, DMSO-d$_6$): δ 10.85 (s, 0.7H), 10.59 (s, 0.3H), 7.75–7.71 (m, 1.0H), 7.70–7.66 (m, 1.0H), 7.60–7.49 (m, 1.0H), 7.32 (d, J=5.2 Hz, 0.3H), 7.30–7.25 (m, 0.7H), 7.19–7.03 (m, 3.0H), 6.93–6.84 (m, 1.0H), 6.78 (d, J=8.0 Hz, 0.7H), 6.65 (d, J=8.8 Hz, 0.3H), 6.58 (d, J=8.4 Hz, 1.0H), 5.57 (s, 0.7H), 5.53–5.47 (m, 0.7H), 5.41 (s, 0.3H), 5.28–5.21 (bs, 0.3H), 3.62–3.54 (m, 2.0H). Mass spectrum (LCMS, ESI pos.) Calcd. For C$_{22}$H$_{16}$ClIN$_2$O$_4$S: 565.96. Found: 566.90 (M+H), 591.32 (M+Na).

Example 127

[7-Iodo-2,5-dioxo-3-(4-trifluoromethoxy-phenyl)-1,2,3,5-tetrahydro benzo[e][1,4]diazepin-4-yl]-(4-trifluoromethyl-phenyl)-acetic acid $^1$H NMR (400 MHz, DMSO-d$_6$): δ 10.66 (s, 0.8H), 10.57 (s, 0.2H), 7.79–7.74 (d, J=2.0 Hz, 1.0H), 7.73–7.61 (m, 4.0H), 7.56–7.49 (dd, J=1.6 Hz, 8.4 Hz, 1.0H), 7.03–6.92 (m, 3.0H), 6.62 (d, J=8.4 Hz, 2.0H), 6.27 (bs, 1.0H), 5.93 (s, 0.4H), 5.38 (s, 0.6H). Mass spectrum (LCMS, ESI pos.) Calcd. For C$_{25}$H$_{15}$F$_6$IN$_2$O$_5$: 663.99. Found 664.89 (M+H).

Example 128

(4-Chloro-phenyl)-[7-iodo-2,5-dioxo-3-(4-trifluoromethoxy-phenyl)-1,2,3,5-tetrahydrobenzo[e][1,4]diazepin-4-yl]-acetic acid $^1$H NMR (400 MHz, DMSO-d$_6$): δ 10.53 (s, 0.6H), 10.49 (s, 0.4H), 7.74 (d, J=2.3 Hz, 0.6H), 7.66 (d, J=2.1 Hz, 0.4H), 7.53–7.47 (m, 2.0H), 7.38–7.32 (m, 2.0H), 7.28 (d, J=8.8 Hz, 1.0H), 7.09 (d, J=8.8 Hz, 1.0H), 7.05–6.88 (m, 3.0H), 6.62 (d, J=8.8 Hz, 0.6H), 6.53 (d, J=9.6 Hz, 0.4H), 6.28 (s, 0.4H), 6.20 (s, 0.6H), 5.89 (s, 0.4H), 5.23 (s, 0.6H). Mass spectrum (LCMS, ESI pos.) Calcd. For C$_{24}$H$_{15}$ClF$_3$IN$_2$O$_5$: 629.97. Found 630.89 (M+H).

Example 129

(4-Chloro-phenyl)-[7-iodo-2,5-dioxo-3-(4-trifluoromethyl-phenyl)-1,2,3,5-tetrahydrobenzo[e][1,4]diazepin-4-yl]-acetic acid $^1$H NMR (400 MHz, DMSO-d$_6$): δ 10.60 (s, 0.6H), 10.53 (s, 0.4H), 7.78 (d, J=2.0 Hz, 0.6H), 7.70 (d, J=2.0 Hz, 0.4H), 7.56–7.45 (m, 3.0H), 7.43–7.31 (m, 4.0H), 7.10–7.00 (m, 1.0H), 6.62 (d, J=8.8 Hz, 1.0H), 6.52 (d, J=8.8 Hz, 0.6H), 6.31 (s, 0.4H), 6.24 (s, 0.6H), 6.02–5.96 (m, 0.4H), 5.31–5.25 (m, 1.0H). Mass spectrum (LCMS, ESI pos.) Calcd. For C$_{24}$H$_{15}$ClF$_3$IN$_2$O$_4$: 613.97. Found 614.86(M+H).

Example 130

[3-(4-Bromo-phenyl)-7-iodo-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): δ 10.60 (s, 0.7H), 10.48 (s, 0.3H), 7.80 (d, J=2.4 Hz, 0.7H), 7.72 (d, J=2.0 Hz, 0.3H), 7.56–7.45 (m, 2.0H), 7.40–7.27 (m, 3.0H), 7.25–7.18 (m, 1.0H), 7.15–7.09 (m, 1.0H), 6.77 (m, 1.0H), 6.63 (d, J=8.8 Hz, 0.3H), 6.54 (d, J=4.8 Hz, 0.7H), 6.27 (s, 0.3H), 6.22 (s, 0.7H), 5.84 (bs, 1.0H), 5.16 (s, 1.0H). Mass spectrum (LCMS, ESI pos.) Calcd. For C$_{23}$H$_{15}$BrClIN$_2$O$_4$: 623.89. Found 626.77 (M+H).

Example 131

[3-(4-Bromo-phenyl)-2,5-dioxo-7-phenyl-1,2,3,5-tetrahydro-benzo[e][1,4]diazepin-4-yl]-(4-chlorophenyl)-acetic acid $^1$H NMR (400 MHz, DMSO-d$_6$): δ 10.67 (s, 0.7H), 10.53 (s, 0.3H), 7.82 (d, J=2.0 Hz, 0.7H), 7.74 (d, J=2.0 Hz, 0.3H), 7.58–7.49 (m, 4.0H), 7.47–7.40 (m, 3.0H), 7.38–7.30 (m, 3.0H), 7.29–7.24 (m, 1.0H), 7.21–7.14 (m, 2.0H), 6.91 (d, J=8.4 Hz, 1.0H), 6.86–6.79 (m, 1.0H), 6.40 (s, 0.3H), 6.34 (s, 0.7H), 5.81 (s, 0.3H), 5.26 (s, 0.7H). Mass spectrum (LCMS, ESI pos.) Calcd. For C$_{29}$H$_{20}$BrClN$_2$O$_4$: 574.03. Found 574.90 (M+H).

Example 132

(4-Chloro-phenyl)-[2,5-dioxo-7-phenyl-3-(4-trifluoromethyl-phenyl)-1,2,3,5-tetrahydro-benzo[e][1,4]diazepin-4-yl]-acetic acid $^1$H NMR (400 MHz, DMSO-d$_6$): δ 10.69 (s, 0.5H), 10.55 (s, 0.5H), 7.79–7.68 (m, 2.0H), 7.58–7.29 (m, 11.0H), 7.16 (bs, 2.0H), 6.94–6.85 (m, 0.5H), 6.80 (d, J=8.4 Hz, 0.5H), 6.40 (bs, 0.5H), 6.30 (bs, 0.5H), 5.95 (bs, 0.5H), 5.33 (bs, 0.5H). Mass spectrum (LCMS, ESI pos.) Calcd. For C$_{30}$H$_{20}$ClF$_3$N$_2$O$_4$: 564.11. Found 565.02 (M+H).

Example 133

(4-Chloro-phenyl)-[2,5-dioxo-7-phenyl-3-(4-trifluoromethoxy-phenyl)-1,2,3,5-tetrahydro-benzo[e][1,4]diazepin-4-yl]-acetic acid $^1$H NMR (400 MHz, DMSO-d$_6$): δ 10.63 (s, 0.4H), 10.50 (s, 0.6H), 7.73 (d, J=2.4 Hz, 0.4H), 7.66 (d, J=2.4 Hz, 0.6H), 7.60–7.28 (m, 11.0H), 7.05 (d, J=8.4 Hz, 2.0H), 6.99 (s, 1.0H), 6.90 (d, J=8.0 Hz, 0.6H), 6.80 (d, J=8.4 Hz, 0.4H), 6.40 (bs, 0.6H), 6.29 (bs, 0.4H), 5.87 (bs, 0.6H), 5.30 (bs, 0.4H). Mass spectrum (LCMS, ESI pos.) Calcd. For C$_{30}$H$_{20}$ClF$_3$N$_2$O$_5$: 580.10. Found 581.00 (M+H).

Example 134

(4-Chloro-phenyl)-[3-(4-chloro-phenyl)-2,5-dioxo-7-phenyl-1,2,3,5-tetrahydro-benzo[e][1,4]diazepin-4-yl]-acetic acid $^1$H NMR (400 MHz, DMSO-d$_6$): δ 10.62 (s, 0.4H), 10.51 (s, 0.6H), 7.81 (d, J=1.6 Hz, 0.4H), 7.73 (d, J=2.4 Hz, 0.6H), 7.59–7.48 (m, 4.0H), 7.47–7.30 (m, 5.0H), 7.23 (d, J=8.4 Hz, 1.0H), 7.13 (d, J=8.4 Hz, 2.0H), 7.06 (d, J=8.8 Hz, 2.0H), 6.91 (d, J=8.0 Hz, 1.0H), 6.82 (d, J=8.4 Hz, 1.0H), 6.39 (bs, 0.6H), 6.33 (bs, 0.4H), 5.84 (bs, 0.4H), 5.27 (bs, 0.6H). Mass spectrum (LCMS, ESI pos.) Calcd. For C$_{29}$H$_{20}$Cl$_2$N$_2$O$_4$: 530.08. Found 531.01(M+H).

Example 135

[3-(4-Chloro-phenyl)-7-iodo-2,5-dioxo-1,2,3,5-tetrahydro-benzo[e][1,4]diazepin-4-yl]-thiophen-2-yl-acetic acid $^1$H NMR (400 MHz, DMSO-d$_6$): δ 10.62 (s, 0.8H), 10.52 (s, 0.2H), 7.80 (d, J=2.4 Hz, 0.8H), 7.73 (d, J=2.4 Hz, 0.2H), 7.56–7.51 (m, 1.0H), 7.37 (d, J=8.4 Hz, 1.0H), 7.19–7.15 (m, 1.0H), 7.10 (d, J=8.6 Hz, 2.0H), 6.95–6.91 (m, 1.0H), 6.80 (d, J=8.4 Hz, 2.0H), 6.65 (d, J=8.6 Hz, 0.8H), 6.58 (d, J=8.4 Hz, 0.2H), 6.44 (bs, 0.6H), 5.85 (bs, 0.4H), 5.50 (bs, 1.0H). Mass spectrum (LCMS, ESI pos.) Calcd. For C$_{21}$H$_{14}$ClIN$_2$O$_4$S: 551.94. Found 552.83 (M+H).

Example 136

[7-Iodo-2,5-dioxo-3-(4-trifluoromethoxy-phenyl)-1,2,3,5-tetrahydro-benzo[e][1,4]diazepin-4-yl]-thiophen-2-yl-acetic acid $^1$H NMR (400 MHz, DMSO-d$_6$): δ 10.65 (s, 0.8H), 10.52 (s, 0.2H), 7.74 (d, 2.0 Hz, 0.8H), 7.68 (d, J=2.0 Hz, 0.2H), 7.55–7.49 (m, 1.0H), 7.42–7.37 (m, 1.0H), 7.28 (d, J=8.4 Hz, 0.2H), 7.20 (d, J=2.8 Hz, 0.8H), 7.13–6.99 (m, 2.0H), 6.96–6.87 (m, 3.0H), 6.64 (d, J=8.8 Hz, 0.8H), 6.56 (d, J=8.8 Hz, 0.2H), 6.44 (bs, 0.8H), 5.88 (bs, 0.2H), 5.55 (bs, 1.0H). Mass spectrum (LCMS, ESI pos.) Calcd. For C$_{22}$H$_{14}$F$_3$N$_2$O$_5$S: 601.96. Found 602.81(M+H).

Example 137

(3-Biphenyl-4-yl-7-iodo-2,5-dioxo-1,2,3,5-tetrahydro-benzo[e][1,4]diazepin-4-yl)-(4-chloro-phenyl)-acetic acid $^1$H NMR (400 MHz, DMSO-d$_6$): δ 10.63 (s, 0.7H), 10.52 (s, 0.3H), 7.82 (d, J=2.0 Hz, 0.7H), 7.74 (d, J=2.4 Hz, 0.3H), 7.57–7.22 (m, 12.0H), 6.86 (d, J=7.6 Hz, 2.0H), 6.66 (d, J=7.6 Hz, 0.7H), 6.56 (d, J=8.8 Hz, 0.3H), 6.33 (bs, 0.7H), 5.95 (bs, 0.3H), 5.29 (bs, 1.0H). Mass spectrum (LCMS, ESI pos.) Calcd. For C$_{29}$H$_{20}$ClN$_2$O$_4$: 622.02. Found 622.91 (M+H).

Example 138

[3-(4-Chloro-phenyl)-7-iodo-2,5-dioxo-1,2,3,5-tetrahydro-benzo[e][1,4]diazepin-4-yl]-(4-ethyl-phenyl)-acetic acid $^1$H NMR (400 MHz, DMSO-d$_6$): δ 10.68 (s, 0.8H), 10.51 (s, 0.2H), 7.79 (d, J=2.0 Hz, 0.8H), 7.73 (d, J=2.0 Hz, 0.2H), 7.56–7.49 (m, 1.01H), 7.39 (d, J=8.0 Hz, 2.0H), 7.29–7.15 (m, 1.0H), 7.12 (d, J=8.0 Hz, 2.0H), 7.06 (d, J=8.4 Hz, 1.0H), 6.77 (d, J=8.0 Hz, 2.0H), 6.64 (d, J=8.4 Hz, 0.8H), 6.55 (d, J=8.8 Hz, 0.2H), 6.30 (bs, 1.0H), 5.82 (bs, 0.2H), 5.21 (bs, 0.8H), 2.62–2.51 (m, 2.0H), 1.21–1.14 (m, 3.0H). Mass spectrum (LCMS, ESI pos.) Calcd. For C$_{25}$H$_{20}$ClIN$_2$O$_4$: 574.02. Found 574.94 (M+H).

Example 139

[3-(4-Chloro-phenyl)-7-iodo-2,5-dioxo-1,2,3,5-tetrahydro-benzo[e][1,4]diazepin-4-yl]-(3,4-dichloro-phenyl)-acetic acid $^1$H NMR (400 MHz, DMSO-d$_6$): δ 10.70 (s, 0.6H), 10.64 (s, 0.4H), 7.79 (d, J=2.0 Hz, 1.0H), 7.81–7.78 (m, 1.0H), 7.61–7.46 (m, 2.0H), 7.40–7.31 (m, 1.0H), 7.18 (s, 1.0H), 7.13 (d, J=8.4 Hz, 1.0H), 7.04–7.00 (m, 1.0H), 6.63 (d, J=8.4 Hz, 1.0H), 6.56 (d, J=8.8 Hz, 0.6H), 6.29 (bs, 0.4H), 6.12 (bs, 0.6H), 5.80 (bs, 0.4H), 5.32 (bs, 1.0H). Mass spectrum (LCMS, ESI pos.) Calcd. For C$_{23}$H$_{14}$Cl$_3$IN$_2$O$_4$: 613.91. Found 614.84 (M+H).

Example 140

(2-Chloro-phenyl)-[3-(4-chloro-phenyl)-7-iodo-2,5-dioxo-1,2,3,5-tetrahydro-benzo[e][1,4]diazepin-4-yl]-acetic acid $^1$H NMR (400 MHz, DMSO-d$_6$): δ 10.61 (s, 0.2H), 10.55 (s, 0.8H), 7.77 (d, J=2.4 Hz, 1.0H), 7.60–7.49 (m, 2.0H), 7.44–7.30 (m, 4.0H), 7.16 (d, J=8.8 Hz, 1.0H), 7.11 (d, J=8.4 Hz, 0.2H), 6.89 (d, J=8.0 Hz, 0.8H), 6.61 (d, J=8.8 Hz, 1.0H), 6.55 (d, J=8.8 Hz, 1.0H), 6.29 (bs, 1.0H), 5.23 (bs, 0.8H), 5.10 (bs, 0.2H). Mass spectrum (LCMS, ESI pos.) Calcd. For C$_{23}$H$_{15}$Cl$_2$IN$_2$O$_4$: 579.95. Found 580.92 (M+H).

Example 141

(4-tert-Butyl-phenyl)-[3-(4-chloro-phenyl)-7-iodo-2,5-dioxo-1,2,3,5-tetrahydro-benzo[e][1,4]diazepin-4-yl]-acetic acid $^1$H NMR (400 MHz, DMSO-d$_6$): δ 10.62 (s, 0.7H), 10.55 (s, 0.3H), 7.77 (d, J=2.0 Hz, 0.7H), 7.75–7.67 (m, 0.3H), 7.55–7.48 (m, 1.0H), 7.39 (d, J=8.4 Hz, 2.0H), 7.29 (d, J=8.4 Hz, 2.0H), 7.25–7.14 (m, 1.0H), 7.02 (d, J=8.0 Hz, 2.0H), 6.92 (d, J=8.0 Hz, 0.3H), 6.73–6.62 (m, 3.0H), 6.54 (d, J=8.4 Hz, 0.7H), 6.27 (s, 1.0H), 5.92 (bs, 0.3H), 5.27 (bs, 0.7H), 1.27 (s, 1.0H), 1.20 (s, 9.0H). Mass spectrum (LCMS, ESI pos.) Calcd. For C$_{27}$H$_{24}$ClIN$_2$O$_4$: 602.05. Found 602.99 (M+H).

Example 142

[3-(4-Chloro-phenyl)-7-iodo-2,5-dioxo-1,2,3,5-tetrahydro-benzo[e][1,4]diazepin-4-yl]-(4-isopropyl-phenyl)-acetic acid $^1$H NMR (400 MHz, DMSO-d$_6$): δ 10.69 (s, 0.8H), 10.54 (s, 0.2H), 7.79 (d, J=2.0 Hz, 0.8H), 7.73 (d, J=2.0 Hz, 0.2H), 7.57–7.50 (m, 1.0H), 7.39 (d, J=8.0 Hz, 2.0H), 7.27 (d, J=8.0 Hz, 0.8H), 7.21 (d, J=8.4 Hz, 0.2H), 7.14 (d, J=8.0 Hz, 2.0H), 7.03 (d, J=8.4 Hz, 2.0H), 6.72 (d, J=8.8 Hz, 1.0H), 6.65 (d, J=8.8 Hz, 1.0H), 6.54 (d, J=8.8 Hz, 0.2H), 6.30 (bs, 0.8H), 5.86 (bs, 0.2H), 5.27 (bs, 0.8H), 2.88–2.76 (m, 1.0H), 1.18 (d, J=8.8 Hz, 1.2H), 1.11 (d, J=6.8 Hz, 6.0H). Mass spectrum (LCMS, ESI pos.) Calcd. For C$_{26}$H$_{22}$ClIN$_2$O$_4$: 588.03. Found 588.95 (M+H).

Example 143

(3-Chloro-phenyl)-[3-(4-chloro-phenyl)-7-iodo-2,5-dioxo-1,2,3,5-tetrahydro-benzo[e][1,4]diazepin-4-yl]-acetic acid $^1$H NMR (400 MHz, DMSO-d6): δ 10.69 (s, 0.7H), 10.60 (s, 0.3H), 7.80 (d, J=2.0 Hz, 0.7H), 7.73 (d, J=2.4 Hz 0.3H), 7.57–7.50 (m, 2.0H), 7.49–7.44 (m, 0.7H), 7.41 (s, 0.3H), 7.35–7.29 (m, 3.0H), 7.18 (s, 1.0H), 6.92 (d, J=8.0 Hz, 2.0H), 6.63 (d, J=8.8 Hz, 0.7H), 6.56 (d, J=8.4 Hz, 0.3H), 6.31 (bs, 0.3H), 6.23 (bs, 0.7H), 5.84 (bs, 0.3H), 5.26 (bs, 0.7H). Mass spectrum (LCMS, ESI pos.) Calcd. For C$_{23}$H$_{15}$Cl$_2$IN$_2$O$_4$: 579.95. Found 581.00 (M+H).

Example 144

[3-(4-Chloro-phenyl)-7-iodo-2,5-dioxo-1,2,3,5-tetrahydro-benzo[e][1,4]diazepin-4-yl]-(4-trifluoromethoxy-phenyl)-acetic acid $^1$H NMR (400 MHz, DMSO-d$_6$): δ 10.72 (s, 0.8H), 10.59 (s, 0.2H), 7.80 (d, J=2.0 Hz, 0.8H), 7.74 (d, J=2.0 Hz, 0.2H), 7.61 (d, J=8.8 Hz, 2.0H), 7.57–7.48 (m, 2.0H), 7.28 (d, J=8.4 Hz, 2.0H), 7.18 (s, 1.0H), 7.07 (d, J=8.4 Hz, 1.0H), 6.85–6.12 (m, 1.0H), 6.65 (d, J=8.4 Hz, 0.8H), 6.55 (d, J=8.4 Hz, 0.2H), 6.35 (bs, 0.2H), 6.31 (bs, 0.8H), 5.77 (bs, 0.2H), 5.31 (bs, 0.8H). Mass spectrum (LCMS, ESI pos.) Calcd. For C$_{24}$H$_{15}$ClF$_3$IN$_2$O$_5$: 629.97. Found 630.95 (M+H).

Example 145

(4-Bromo-phenyl)-[3-(4-chloro-phenyl)-7-iodo-2,5-dioxo-1,2,3,5-tetrahydro-benzo[e][1,4]diazepin-4-yl]-acetic acid $^1$H NMR (400 MHz, DMSO-d$_6$): δ 10.69 (s, 0.7H), 10.56 (s, 0.3H), 7.79 (d, J=2.0 Hz, 0.7H), 7.73 (d, J=2.0 Hz, 0.3H), 7.58–7.41(m, 5.0H), 7.32 (d, J=8.4 Hz, 1.0H), 7.23 (s, 1.0H), 7.11 (d, J=8.8 Hz, 1.0H), 6.94–6.85 (m, 1.0H), 6.64 (d, J=8.4 Hz, 0.7H), 6.55 (d, J=8.0 Hz, 0.3H), 6.29 (bs, 0.3H), 6.23 (bs, 0.7H), 5.78 (bs, 0.3H), 5.23 (bs, 0.7H). Mass spectrum (LCMS, ESI pos.) Calcd. For C$_{23}$H$_{15}$BrClIN$_2$O$_4$: 623.89. Found 624.90 (M+H).

Example 146

[3-(4-Chloro-phenyl)-7-iodo-2,5-dioxo-1,2,3,5-tetrahydro-benzo[e][1,4]diazepin-4-yl]-(3-hydroxy-phenyl)-acetic acid $^1$H NMR (400 MHz, DMSO-d$_6$): δ 10.48 (s, 1.0H), 9.50, (s, 1.0H), 7.78 (d, J=2.0 Hz, 1.0H), 7.54 (dd, J=2.0 Hz, 8.0 Hz, 1.0H), 7.08 (d, J=8.4 Hz, 3.0H), 6.91 (s, 2.0H), 6.84–6.76 (m, 2.0H), 6.69–6.59 (m, 2.0H), 6.26 (bs, 1.0H), 5.24 (bs, 1.0H). Mass spectrum (LCMS, ESI pos.) Calcd. For C$_{23}$H$_{16}$ClIN$_2$O$_5$: 561.98. Found 562.89 (M+H).

Example 147

[3-(4-Chloro-phenyl)-7-iodo-2,5-dioxo-1,2,3,5-tetrahydro-benzo[e][1,4]diazepin-4-yl]-(4-hydroxy-phenyl)-acetic acid $^1$H NMR (400 MHz, DMSO-d$_6$): δ 10.58 (s, 0.7H), 10.43 (s, 0.3H), 9.43 (s, 0.7H), 9.38 (s, 0.3H) 7.76 (d, J=2.4 Hz, 1.0H), 7.70 (d, J=1.6 Hz, 0.3H), 7.50 (m, 0.7H), 7.25 (d, J=8.4 Hz, 2.0H), 7.23–7.11 (m, 3.0H), 7.07 (d, J=2.4 Hz, 1.0H), 6.83–6.76 (m, 1.0H), 6.68–6.60 (m, 2.0H), 6.22 (bs, 1.0H), 6.17 (bs, 0.3H), 5.14 (bs, 0.7H). Mass spectrum (LCMS, ESI pos.) Calcd. For C$_{23}$H$_{16}$ClIN$_2$O$_5$: 561.98. Found 562.80 (M+H).

Example 148

(4-Chloro-phenyl)-[3-(4-chloro-3-trifluoromethyl-phenyl)-7-iodo-2,5-dioxo-1,2,3,5-tetrahydro-benzo[e][1,4]diazepin-4-yl]-acetic acid $^1$H NMR (400 MHz, DMSO-d$_6$): δ 10.80 (s, 0.6H), 10.63 (s, 0.4H), 7.76–7.69 (m, 1.0H), 7.61–7.44 (m, 3.0H), 7.40 (s, 1.0H), 7.36–7.21 (m, 1.0H), 7.17 (d, J=8.0 Hz, 1.0H), 6.67–6.51 (m, 2.0H), 6.38–6.19 (m, 1.0H), 5.63 (bs, 0.4H), 5.50 (bs, 0.6H), 5.17 (bs, 1.0H). Mass spectrum (LCMS, ESI pos.) Calcd. For C$_{24}$H$_{14}$Cl$_2$F$_3$IN$_2$O$_4$: 647.93. Found 648.91 (M+H).

Example 149

[3-(4-Chloro-phenyl)-7-iodo-2,5-dioxo-1,2,3,5-tetrahydro-benzo[e][1,4]diazepin-4-yl]-cyclohexyl-acetic acid $^1$H NMR (400 MHz, DMSO-d$_6$): δ 10.99 (s, 1.0H), 7.74 (d, J=1.6 Hz, 1.0H), 7.57 (dd, J=2.0 Hz, 8.4 Hz, 1.0H), 7.22 (d, J=8.8 Hz, 2.0H), 6.96 (d, J=8.4 Hz, 2.0H), 6.62 (d, J=8.8 Hz, 1.0H), 5.90 (bs, 1.0H), 5.17–5.10 (m, 1.0H), 1.89–0.87 (m, 1.0H). Mass spectrum (LCMS, ESI pos.) Calcd. For C$_{23}$H$_{22}$ClIN$_2$O$_4$: 552.03. Found 552.90 (M+H).

Example 150

(4-Chloro-phenyl)-[3-(4-chloro-phenyl)-7-iodo-8-methyl-2,5-dioxo-1,2,3,5-tetrahydro-benzo[e][1,4]diazepin-4-yl]-acetic acid $^1$H NMR (400 MHz, DMSO-d$_6$): δ 10.63 (s, 0.4H), 10.51 (s, 0.6H), 7.93 (s, 0.4H), 7.85 (s, 0.6H), 7.50 (d, J=8.8 Hz, 1.0H), 7.41–7.31 (m, 3.0H), 7.18 (s, 2.0H), 7.09 (d, J=8.8 Hz, 1.0H), 6.86–6.81 (m, 0.6H), 6.77 (s, 0.4H), 6.68 (s, 1.0H), 6.35–6.27 (m, 1.0H), 5.78 (bs, 0.6H), 5.25 (bs, 0.4H) 2.18 (s, 1.8H), 2.17 (s, 1.2H). Mass spectrum (LCMS, ESI pos.) Calcd. For C$_{24}$H$_{17}$Cl$_2$IN$_2$O$_4$: 593.96 (M+H). Found 594.89.

Example 151

[3-(4-Chloro-phenyl)-7,8-difluoro-2,5-dioxo-1,2,3,5-tetrahydro-benzo[e][1,4]diazepin-4-yl]-phenyl-acetic acid $^1$H -NMR (400 MHz, DMSO-d$_6$): δ 7.6–7.7 (m, 2H), 7.4–7.5 (m, 1H), 7.2–7.4 (m, 4H), 6.9–7.0 (m, 2H), 6.6–6.8 (m, 4H), 5.7 (s, 0.13H), 5.4 (s, 0.87H). Mass spectrum (LCMS, ESI pos) Calcd. for C$_{23}$H$_{15}$ClF$_2$N$_2$O$_4$: 456.1; Found: 457.0 (M+H).

Example 152

[7,8-Difluoro-2,5-dioxo-3-(4-trifluoromethoxy-phenyl)-1,2,3,5-tetrahydro-benzo[e][1,4]diazepin-4-yl]-phenyl-acetic acid $^1$H-NMR (400 MHz, DMSO-d$_6$): δ 7.6 (m, 2H), 7.2–7.5 (m, 5H), 6.6–6.9 (m, 6H), 5.8 (s, 0.1H), 5.4 (s, 0.9H). (LCMS, ESI pos) Calcd. for C$_{24}$H$_{15}$F$_5$N$_2$O$_5$: 506.1; Found: 507.1 (M +H).

Example 153

[3-(4-Chloro-phenyl)-7-fluoro-2,5-dioxo-1,2,3,5-tetrahydro-benzo[e][1,4]diazepin-4-yl]-phenyl-acetic acid $^1$H-NMR (400 MHz, DMSO-d$_6$): δ 7.6–7.7 (m, 2H), 7.2–7.4 (m, 5H), 6.9–7.1 (m, 2H), 6.6–6.9 (m, 6H), 5.7 (m, 0.1H), 5.4–5.5 (s, 0.9H). Mass spectrum (LCMS, ESI pos) Calcd. for C$_{23}$H$_{16}$ClFN$_2$O$_4$: 438.1; Found: 439.0 (M+H).

Example 154

[7-Fluoro-2,5-dioxo-3-(4-trifluoromethoxy-phenyl)-1,2,3,5-tetrahydro-benzo[e][1,4]diazepin-4-yl]-phenyl-acetic acid $^1$H-NMR (400 MHz, DMSO-d$_6$): δ 7.6–7.7 (m, 2H), 7.4–7.5 (m, 1H), 7.2–7.4 (m, 5H), 6.9–7.0 (m, 2H), 6.6–6.9 (m, 7H), 5.7 (s, 0.2H), 5.5 (s, 0.8H). ). Mass spectrum (LCMS, ESI pos) Calcd. for C$_{24}$H$_{16}$F$_4$N$_2$O$_5$: 488.1; Found: 489.1 (M+H).

Example 155

[7-Acetylamino-3-(4-chloro-phenyl)-2,5-dioxo-1,2,3,5-tetrahydro-benzo[e][1,4]diazepin-4-yl]-phenyl-acetic acid $^1$H-NMR (400 MHz, DMSO-d$_6$): δ 7.4–7.9 (m, 5H), 7.0–7.3 (m, 3H), 6.6–6.9 (m, 7H), 5.4–5.8 (m, 1H), 1.9–2.2 (s, 3H). Mass spectrum (LCMS, ESI pos) Calcd. for C$_{25}$H$_{20}$ClN$_3$O$_5$: 477.1; Found: 478.0 (M+H).

Example 156

[7-Acetylamino-2,5-dioxo-3-(4-trifluoromethoxy-phenyl)-1,2,3,5-tetrahydro-benzo[e][1,4]diazepin-4-yl]-phenyl-acetic acid $^1$H-NMR (400 MHz, DMSO-d$_6$): δ 7.6–7.9 (m, 3H), 7.2–7.5 (m, 5H), 6.6–6.9 (m, 6H), 5.7 (br s, 1H), 1.9–2.2 (s, 1H). (LCMS, ESI pos) Calcd. for C$_{26}$H$_{20}$F$_3$N$_3$O$_6$: 527.1; Found: 528.1 (M+H).

Example 157

[3-(4-Chloro-phenyl)-7-(3-chloro-phenyl)-2,5-dioxo-1,2,3,5-tetrahydro-benzo[e][1,4]diazepin-4-yl]-phenyl-acetic acid $^1$H-NMR (400 MHz, DMSO-d$_6$): δ 7.8–7.9 (s, 1H), 7.6–7.7 (m, 2H), 7.2–7.5 (m, 8H), 6.8–6.9 (m, 3H), 6.7–6.8 (m, 3H), 5.4 (s, 1H). Mass spectrum (LCMS, ESI pos) Calcd. for C$_{29}$H$_{20}$Cl$_2$N$_2$O$_4$: 530.1; Found: 531.0 (M+H).

Example 158

[3-(4-Chloro-phenyl)-7-(4-methyl-thiophen-2-yl)-2,5-dioxo-1,2,3,5-tetrahydro-benzo[e][1,4]diazepin-4-yl]-phenyl-acetic acid $^1$H-NMR (400 MHz, DMSO-d$_6$): δ 7.8 (s, 1H), 7.6–7.7 (s, 1H), 7.4–7.5 (m, 5H), 7.2–7.4 (m, 2H), 6.6–6.9 (m, 5H), 5.7 (s, 0.4H), 5.4–5.5 (s, 0.6H), 2.2 (3H, s). Mass spectrum (LCMS, ESI pos) Calcd. for C$_{28}$H$_{21}$ClN$_2$O$_4$S: 516.1; Found: 517.0 (M+H).

Example 159

[3-(4-Chloro-phenyl)-2,5-dioxo-7-thiophen-3-yl-1,2,3,5-tetrahydro-benzo[e][1,4]diazepin-4-yl]-phenyl-acetic acid $^1$H-NMR (400 MHz, DMSO-d$_6$): δ 7.9 (s, 1H), 7.6 (s, 1H), 7.4–7.55 (m, 4H), 7.2–7.4 (m, 5H), 7.0–7.1 (m, 1H), 6.8–6.9 (m, 2H), 6.7–6.8 (m, 2H), 5.7 (s, 0.5H), 5.4 (s, 0.5H). Mass spectrum (LCMS, ESI pos) Calcd. for C$_{27}$H$_{19}$ClN$_2$O$_4$S: 502.1; Found: 503.0 (M+H).

Example 160

[3-(4-Chloro-phenyl)-7-furan-3-yl-2,5-dioxo-1,2,3,5-tetrahydro-benzo[e][1,4]diazepin-4-yl]-phenyl-acetic acid methyl ester $^1$H-NMR (400 MHz, DMSO-d$_6$): δ 7.9 (s, 1H), 7.8 (s, 1H), 7.4–7.7 (m, 8H), 7.0–7.3 (m, 3H), 6.7–6.9 (m, 3H), 5.3 (s, 0.4H), 5.2 (s, 0.6H,), 3.8 (s, 3H). Mass spectrum (LCMS, ESI pos) Calcd. for C$_{28}$H$_{21}$ClN$_2$O$_5$: 500.0; Found: 501.0 (M+H).

Example 161

[3-(4-Chloro-phenyl)-7-furan-3-yl-2,5-dioxo-1,2,3,5-tetrahydro-benzo[e][1,4]diazepin-4-yl]-phenyl-acetic acid $^1$H-NMR (400 MHz, DMSO-d$_6$): δ 7.8–7.9 (m, 2H), 7.6–7.7 (m, 1H), 7.2–7.5 (m, 7H), 7.0–7.1 (m, 1H), 6.6–6.9 (m, 5H), 5.7 (s, 0.4H), 5.5 (m, 0.6H). Mass spectrum (LCMS, ESI pos) Calcd. for C$_{27}$H$_{19}$ClN$_2$O$_5$: 486.1; Found: 487.0 (M+H).

Example 162

[3,7-Bis-(4-chloro-phenyl)-2,5-dioxo-1,2,3,5-tetrahydro-benzo[e][1,4]diazepin-4-yl]-phenyl-acetic acid methyl ester $^1$H-NMR (400 MHz, DMSO-d$_6$): δ 7.8–7.9 (s, 1H), 7.4–7.7 (m, 11H), 7.1–7.2 (m, 1H), 6.8–7.0 (m, 4H), 6.7 (m, 1H), 5.3 (s, 0.18H), 5.25 (s, 0.82H), 3.8 (s, 3H). Mass spectrum (LCMS, ESI pos) Calcd. for C$_{30}$H$_{22}$Cl$_2$N$_2$O$_4$: 544.1; Found: 545.0 (M+H).

Example 163

[3,7-Bis-(4-chloro-phenyl)-2,5-dioxo-1,2,3,5-tetrahydro-benzo[e][1,4]diazepin-4-yl]-phenyl-acetic acid $^1$H-NMR (400 MHz, DMSO-d$_6$): δ 7.8–7.9 (m, 1H), 7.6–7.7 (m, 1H), 7.4–7.5 (m, 4H), 7.2–7.4 (m, 6H), 7.0–7.1 (m, 1H), 6.7–6.9 (m, 4H), 5.7 (s, 0.5H), 5.45 (s, 0.5H). Mass spectrum (LCMS, ESI pos) Calcd. for C$_{29}$H$_{20}$Cl$_2$N$_2$O$_4$: 530.1; Found: 531.0 (M+H).

Example 164

[7-(3-Amino-phenyl)-3-(4-chloro-phenyl)-2,5-dioxo-1,2,3,5-tetrahydro-benzo[e][1,4]diazepin-4-yl]-phenyl-acetic acid $^1$H-NMR (400 MHz, DMSO-d$_6$): δ 7.8–7.9 (m, 1H), 7.6–7.7 (s, 1H), 7.2–7.5 (m, 5H), 7.0–7.1 (m, 4H), 6.5–6.9 (m, 6H), 5.7 (s, 0.4H), 5.5 (br s, 0.6H). Mass spectrum (LCMS, ESI pos) Calcd. for C$_{29}$H$_{22}$ClN$_3$O$_4$: 511.1; Found: 512.1 (M+H).

Example 165

[3-(4-Chloro-phenyl)-7-(3-isopropyl-phenyl)-2,5-dioxo-1,2,3,5-tetrahydro-benzo[e][1,4]diazepin-4-yl]-phenyl-acetic acid $^1$H-NMR (400 MHz, DMSO-d$_6$): δ 7.8–7.9 (m, 1H), 7.6–7.7 (m, 1H), 7.4–7.5 (m, 3H), 7.2–7.4 (m, 6H), 7.0–7.1 (m, 1H), 6.6–6.9 (m, 5H), 5.7 (s, 0.3H), 5.5 (s, 0.7H), 2.9–3.0 (m, 1H), 1.2–1.3 (m, 6H). Mass spectrum (LCMS, ESI pos) Calcd. for C$_{32}$H$_{27}$ClN$_2$O$_4$: 538.2; Found: 539.1 (M+H).

Example 166

(4-Chloro-phenyl)-[3-(4-chloro-phenyl)-7-iodo-5-oxo-2-thioxo-1,2,3,5-tetrahydro-benzo[e][1,4]diazepin-4-yl]-acetic acid $^1$H-NMR (400 MHz, DMSO-d$_6$): δ 12.3–12.5 (br s, 1H), 7.7–7.8 (m, 1H), 7.5–7.6 (m, 2H), 7.2–7.4 (m, 6H), 7.1–7.2 (m, 2H), 6.6–6.8 (m, 1H), 6.4 (s, 0.7H), 6.2 (s, 0.7H), 5.7 (m, 0.6H). Mass spectrum (LCMS, ESI pos) Calcd. for C$_{23}$H$_{15}$Cl$_2$IN$_2$O$_3$S : 595.9; Found: 596.9 (M+H).

Example 167

(4-Chloro-phenyl)-[3-(4-chloro-phenyl)-2,5-dioxo-7-vinyl-1,2,3,5-tetrahydro-benzo[e][1,4]diazepin-4-yl]-acetic acid $^1$H NMR (400 MHz, DMSO-d$_6$): 10.67 (s, 0.6H), 10.52 (s, 0.4H), 7.54–7.36 (m, 6H), 7.19–7.05 (m, 3H), 6.95 (m, 1H), 6.82 (d, J=8.4 Hz, 0.6H), 6.7 (d, J=8.4 Hz, 0.4H), 6.64–6.55 (m, 1H), 6.32 (br s, 0.6H), 6.25 (br s, 0.4H), 5.73 (brs, 0.4H), 5.70–5.66 (m, 1H), 5.26 (s, 0.6H), 5.19–5.16 (m, 1H). Mass spectrum (LCMS, ESI pos) Calcd. for C$_{25}$H$_{18}$N$_2$O$_4$Cl$_2$: 480.06; Found: 481.07(M+H).

Example 168

(4-Chloro-phenyl)-[3-(4-chloro-phenyl)-7-cyano-2,5-dioxo-1,2,3,5-tetrahydro-benzo[e][1,4]diazepin-4-yl]-acetic acid $^1$H NMR (400 MHz, DMSO-d$_6$): 11.13 (s, 0.7H), 10.97 (s, 0.3H), 7.88 (m, 1H), 7.68 (m, 1H), 7.50–7.41 (m, 4H), 7.17 (m, 3H), 7.01 (m, 2H), 6.28 (br s, 0.3H), 6.27 (br s, 0.7H), 5.70 (brs, 0.3H), 5.25 (s, 0.7H). Mass spectrum (LCMS, ESI pos) Calcd. for C$_{24}$H$_{15}$N$_3$O$_4$Cl$_2$: 479.04; Found: 479.9(M+H).

Example 169

[3-(1-Chloro-cuban-4-yl)-7-iodo-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): 10.64 (s, 1H), 8.03 (d, J=2.2 Hz, 1H), 7.86 (dd, J=8.4 Hz and J=2.2 Hz, 1H), 7.47 (d, J=8.7 Hz, 2H), 7.37 (d, J=8.8 Hz, 2H), 6.88 (d, J=8.7 Hz, 1H), 4.62 (s, 1H), 4.16 (s, 1H), 3.80–3.73 (m, 3H), 3.70–3.64 (m, 3H). Mass spectrum (LCMS, ESI pos.): Calcd. for C$_{25}$H$_{17}$Cl$_2$IN$_2$O$_4$: 605.96; found: 606.99 (M+H).

Example 170

3-(4-Chloro-phenyl)-4-[1-(4-chloro-phenyl)-2-hydroxy-ethyl]-7-iodo-1,3,4,5-tetrahydro-benzo[e][1,4]diazepin-2-one $^1$H NMR (400 MHz, CDCl$_3$): 7.50 (br s, 1H), 7.45 (dd, J=8.3 Hz and J=2.0 Hz, 1H), 7.33 (d, J=8.4 Hz, 2H), 7.29 (d, J=8.8 Hz, 2H), 7.26 (d, J=8.8 Hz, 2H), 7.23 (d, J=8.5 Hz, 2H), 7.12 (d, J=1.9 Hz, 1H), 6.49 (d, J=8.3 Hz, 1H), 5.14 (s, 1H), 4.08–4.00 (m, 1H), 3.95–3.85 (m, 2H), 3.89 (d, J=14.9 Hz, 1H), 3.58 (d, J=14.8 Hz, 1H), 2.02–1.99 (m, 1H). Mass spectrum (LCMS, ESI pos.): Calcd. for C$_{23}$H$_{19}$Cl$_2$IN$_2$O$_2$: 551.99; found: 552.90 (M+H).

Example 171

3-(4-Chloro-phenyl)-4-[1-(4-chloro-phenyl)-2-hydroxy-ethyl]-7-iodo-1,2,3,4-tetrahydro-benzo[e][1,4]diazepin-5-one $^1$H NMR (400 MHz, CDCl$_3$): 8.52 (d, J=2.1 Hz, 1H), 7.36 (dd, J=8.6 Hz and J=2.2 Hz, 1H), 7.20–7.14 (m, 4H), 7.08 (d, J=8.5 Hz, 2H), 6.81 (d, J=8.4 Hz, 2H), 6.18 (d, J=8.6 Hz, 1H), 5.48–5.45 (m, 1H), 4.73 (d, J=6.0 Hz, 1H), 4.47–4.40 (m, 1H), 4.33–4.24 (m, 1H), 4.22–4.15 (m, 1H), 3.83–3.75 (m, 1H), 3.71–3.64 (m, 1H), 3.14–3.08 (m, 1H). Mass spectrum (LCMS, ESI pos.): Calcd. for C$_{23}$H$_{19}$Cl$_2$IN$_2$O$_2$: 551.99; found: 552.84 (M+H).

Example 172

3-(4-Chlorophenyl)-4-(2-hydroxy-1-phenyl-ethyl)-7-iodo-3,4-dihydro-1H-benzo[e][1,4]diazepine-2,5-dione $^1$H NMR (400 MHz, DMSO-d$_6$): 10.82 (br s, 1H), 7.80 (d, J=2.1 Hz, 1H), 7.55 (dd, J=8.5 Hz and J=2.1 Hz, 1H), 7.51 (d, J=7.4 Hz, 2H), 7.40–7.26 (m, 3H), 7.03 (d, J=8.6 Hz, 2H), 6.64–6.58 (m, 3H), 6.13–6.05 (m, 1H), 5.17 (s, 1H), 5.05 (t, J=5.0 Hz, 1H), 4.11–3.97 (m, 2H). Mass spectrum (LCMS, ESI pos.): Calcd. for C$_{23}$H$_{18}$ClIN$_2$O$_3$: 532.01; found: 532.95 (M+H).

Example 173

3-(4-Chloro-phenyl)-4-(3-hydroxy-1-phenyl-propyl)-7-iodo-3,4-dihydro-1H-benzo[e][1,4]diazepine-2,5-dione $^1$H NMR (400 MHz, DMSO-d$_6$): 10.94 (s, 1H), 7.80 (d, J=2.1 Hz, 1H), 7.59 (d, J=7.3, 2H), 7.54 (dd, J=8.5 Hz and J=2.1 Hz, 1H), 7.37 (t, J=7.4 Hz, 2H), 7.30 (t, J=7.3 Hz, 1H), 6.99 (d, J=8.6 Hz, 2H), 6.64 (d, J=8.5 Hz, 1H), 6.45 (d, J=8.7 Hz, 2H), 6.33 (t, J=7.7 Hz, 1H), 5.25 (s, 1H), 4.61 (t, J=4.9 Hz, 1H), 3.48–3.39 (m, 2H), 2.28–2.20 (m, 2H). Mass spectrum (LCMS, ESI pos.): Calcd. for C$_{24}$H$_{20}$ClIN$_2$O$_3$: 546.02; found: 546.91 (M+H).

Example 174

2-(4-Chloro-phenyl)-2-[3-(4-chloro-phenyl)-7-iodo-2,5-dioxo-1,2,3,5-tetrahydro-benzo[e][1,4]diazepin-4-yl]-N-(2-hydroxy-ethyl)-acetamide $^1$H NMR (400 MHz, DMSO-d$_6$): 10.73 (s, 1H), 8.25 (t, J=5.6 Hz, 1H), 7.78 (d, J=2.1 Hz, 1H), 7.56 (dd, J=8.5 Hz and J=2.1 Hz, 1H), 7.50–7.43 (m, 4H), 7.13 (d, J=8.6 Hz, 2H), 6.91 (d, J=7.8 Hz, 2H), 6.64 (d, J=8.5 Hz, 1H), 6.48 (s, 1H), 5.00 (s, 1H), 4.65 (t, J=5.3 Hz, 1H), 3.42–3.37 (m, 2H), 3.29–3.05 (m, 2H). Mass spectrum (LCMS, ESI pos.): Calcd. for C$_{25}$H$_{20}$Cl$_2$IN$_3$O$_4$: 622.99; found: 623.75 (M+H).

Example 175

3-(4-Chloro-phenyl)-3-[3-(4-chloro-phenyl)-7-iodo-2,5-dioxo-1,2,3,5-tetrahydro-benzo[e][1,4]diazepin-4-yl]-propionic acid $^1$H NMR (400 MHz, DMSO-d$_6$): δ 10.90 (s, 1H), 7.81 (d, J=2.4 Hz, 1H), 7.64 (d, J=8.4 Hz, 2H), 7.56 (dd, J=8.0 Hz, 2.0 Hz, 1H), 7.41 (d, J=8.4 Hz, 2H), 7.05 (d, J=8.4 Hz, 2H), 6.61 (d, J=8.4 Hz, 1H), 6.54 (d, J=8.8 Hz, 2H), 6.42 (t, J=8.0 Hz, 1H), 5.31 (s, 1H), 3.15 (d, J=7.2 Hz, 1H). Mass spectrum (LCMS, ESI pos) Calcd. for C$_{24}$H$_{17}$Cl$_2$IN$_2$O$_4$: 593.96; Found 594.90 (M+H).

Example 176

[3-(4-Chloro-phenyl)-7-iodo-2,5-dioxo-1,2,3,5-tetrahydro-benzo[e][1,4]diazepin-4-yl]-(6-chloro-pyridin-3-yl)-acetic acid $^1$H NMR (400 MHz, DMSO-d$_6$): δ 10.64 (s, 0.7H), 10.61 (s, 0.3H), 8.46 (d, J=2.4 Hz, 0.7H), 8.34 (d, J=2.4 Hz, 0.3H), 7.93–7.90 (m, 0.7H), 7.81–7.80 (m, 0.3H), 7.78 (d, J=2 Hz, 0.7H), 7.71 (d, J=2.4 Hz, 0.3H), 7.54–7.51 (m, 1H), 7.46–7.41 (m, 1H), 7.19–7.13 (m, 2.6H), 7.04–7.02 (m, 1.4H), 6.62 (d, J=8.8 Hz, 0.7H), 6.56 (d, J=8.8 Hz, 0.3H), 6.25 (s, 0.3H), 6.04 (s, 0.7H), 5.81 (s, 0.3H), 5.40 (s, 0.7H). Mass spectrum (LCMS, ESI pos) Calcd. for C$_{22}$H$_{14}$Cl$_2$IN$_3$O$_4$: 580.94; Found 581.93 (M+H).

Example 177

2-(4-Chloro-phenyl)-2-[3-(4-chloro-phenyl)-7-iodo-2,5-dioxo-1,2,3,5-tetrahydro-benzo[e][1,4]diazepin-4-yl]-N-hydroxy-acetamide $^1$H NMR (400 MHz, DMSO-d$_6$): δ 10.83 (s, 1H), 7.73 (d, J=2.0 Hz, 1H), 7.76 (dd, J=8.0 Hz, 2.0 Hz, 1H), 7.52–7.45 (m, 3H), 7.20 (d, J=8.8 Hz, 2H), 7.07 (d, J=8.8 Hz, 2H), 6.64 (d, J=8.4 Hz, 1H), 6.20 (s, 1H), 5.24 (s, 1H). Mass spectrum (LCMS, ESI neg) Calcd. for C$_{23}$H$_{16}$Cl$_2$IN$_3$O$_4$: 594.96; Found 578.9.

Example 178

[7-Bromo-3-(4-chloro-phenyl)-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): δ 10.68 (s, 1H), 7.60 (d, J=2.4 Hz, 1H), 7.50 (d, J=8.4 Hz, 2H), 7.44–7.39 (m, 3H), 7.10 (d, J=8.8 Hz, 2H), 6.93–6.85 (m, 2H), 6.78 (d, J=8.8 Hz, 1H), 6.24 (s, 1H), 5.22 (s, 1H). Mass spectrum (LCMS, ESI pos) Calcd. for C$_{23}$H$_{15}$BrCl$_2$N$_2$O$_4$: 531.96; Found 532.90 (M+H).

Example 179

[8-Chloro-3-(4-chloro-phenyl)-7-iodo-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): δ 10.78 (s, 1H), 7.98 (s, 1H), 7.49 (d, J=8.4 Hz, 2H), 7.33 (d, J=8.4 Hz, 2H), 7.10 (d, J=8.4 Hz, 2H), 7.04 (s, 1H), 6.82 (d, J=8.4 Hz, 2H), 6.26 (s, 1H), 5.21 (s, 1H). Mass spectrum (LCMS, ESI pos) Calcd. for C$_{23}$H$_{14}$Cl$_3$IN$_2$O$_4$: 613.91; Found 614.8 (M+H).

Example 180

2-{2-(4-Chloro-phenyl)-2-[3-(4-chloro-phenyl)-7-iodo-2,5-dioxo-1,2,3,5-tetrahydro-benzo[e][1,4]diazepin-4-yl]-acetylamino}-3-methyl-butyric acid $^1$H NMR (400 MHz, DMSO-d$_6$): δ 10.80–10.69 (m, 1H), 8.58–8.47 (m, 1H), 7.62–7.29 (m, 3H), 7.25–6.83 (m, 5H), 6.80–6.50 (m, 2H), 5.04 (s, 0.5H), 4.86 (s, 0.5H), 4.27–4.08 (m, 1H), 2.07–1.97 (m, 1H), 0.92–0.81 (m, 6H). Mass spectrum (LCMS, ESI pos) Calcd. for C$_{28}$H$_{24}$Cl$_2$IN$_3$O$_5$: 679.01; Found 679.66 (M+H).

Example 181

3-(4-Chloro-phenyl)-3-[3-(4-chloro-phenyl)-7-iodo-2,5-dioxo-1,2,3,5-tetrahydro-benzo[e][1,4]diazepin-4-yl]-propionic acid $^1$H NMR (400 MHz, DMSO-d$_6$): δ 10.88 (s, 1H), 7.80 (d, J=2.4 Hz, 1H), 7.59–7.50 (m, 3H), 7.35 (d, J=8.0 Hz, 2H), 7.05 (d, J=8.0 Hz, 2H), 6.64–6.58 (m, 3H), 6.42–6.36 (m, 1H), 5.10 (s, 1H), 2.95–2.86 (m, 1H), 2.4–2.34 (m, 1H).

Example 182

5-{2-(4-Chloro-phenyl)-2-[3-(4-chloro-phenyl)-7-iodo-2,5-dioxo-1,2,3,5-tetrahydro-benzo[e][1,4]diazepin-4-yl]-acetylamino}-pentanoic acid $^1$H NMR (400 MHz, DMSO-d$_6$): δ 12.00 (s, 1H), 10.72 (s, 1H), 8.25 (t, J=5.6 Hz, 1H), 7.77 (d, J=2.0 Hz, 1H), 7.60–7.52 (m, 1H), 7.50–7.41 (m, 4H), 7.13 (dd, J=8.0 Hz, 2.0 Hz, 2H), 6.90 (dd, J=8.0 Hz, 1.2 Hz, 2H), 6.64 (d, J=8.4 Hz, 1H), 6.42 (s, 1H), 4.98 (s, 1H), 3.22–2.98 (m, 2H), 2.23–2.17 (m, 2H), 1.52–1.34 (m, 4H). Mass spectrum (LCMS, ESI pos) Calcd. for C$_{28}$H$_{24}$Cl$_2$IN$_3$O$_5$: 679.01; Found 679.86 (M+H).

Example 183

3-{2-(4-Chloro-phenyl)-2-[3-(4-chloro-phenyl)-7-iodo-2,5-dioxo-1,2,3,5-tetrahydro-benzo[e][1,4]diazepin-4-yl]-acetylamino}-propionic acid $^1$H NMR (400 MHz, DMSO-d$_6$): δ 10.73 (s, 1H), 8.37–8.28 (m, 1H), 7.77 (d, J=2.0 Hz, 1H), 7.58–7.53 (m, 1H), 7.46–7.42 (m, 4H), 7.13 (d, J=8.4 Hz, 2H), 6.91 (d, J=8.4 Hz, 2H), 6.64 (d, J=8.4 Hz, 1H), 6.43 (s, 1H), 4.97 (s, 1H), 3.17 (d, J=5.6 Hz, 2H), 2.42–2.38 (m, 2H). Mass spectrum (LCMS, ESI pos) Calcd. for C$_{26}$H$_{20}$Cl$_2$IN$_3$O$_5$: 650.98; Found 651.68 (M+H).

Example 184

(4-Chloro-phenyl)-[7-iodo-2,5-dioxo-3-(4-trifluoromethylsulfanyl-phenyl)-1,2,3,5-tetrahydro-benzo[e][1,4]diazepin-4-yl]-acetic acid Mass spectrum (LCMS, ESI pos) Calcd. for C$_{24}$H$_{15}$ClF$_3$IN$_2$O$_4$S: 645.94; Found 646.96 (M+H).

Example 185

(4-Chloro-phenyl)-[3-(4-chloro-phenyl)-2,5-dioxo-7-(1H-pyrrol-3-yl)-1,2,3,5-tetrahydro-benzo[e][1,4]diazepin-4-yl]-acetic acid $^1$H NMR (400 MHz, DMSO-d$_6$): δ 10.94 (s, 1H), 10.60 (s, 1H), 7.66–7.35 (m, 6H), 7.22–7.03 (m, 5H), 6.79–6.72 (m, 2H), 6.34–6.28 (m, 1H), 6.21 (s, 1H), 5.25 (s, 1H).
Mass spectrum (LCMS, ESI pos) Calcd. for C$_{27}$H$_{19}$Cl$_2$N$_3$O$_4$: 519.08; Found 520.00 (M+H).

Example 186

3-[4-[Carboxy-(4-chloro-phenyl)-methyl]-3-(4-chloro-phenyl)-7-iodo-2,5-dioxo-2,3,4,5-tetrahydro-benzo[e][1,4]diazepin-1-yl]-propionic acid $^1$H NMR (400 MHz, CD$_3$OD-d$_6$): δ 8.06–7.89 (m, 1.2H), 7.83 (d, J=8.4 Hz, 0.6H), 7.74–7.68 (m, 0.6H), 7.56 (d, J=8.0 Hz, 1H), 7.47–7.24 (m, 3H), 7.08–6.93 (m, 2H), 6.82–6.57

(m, 2H). Mass spectrum (LCMS, ESI pos) Calcd. for C$_{26}$H$_{19}$Cl$_2$IN$_2$O$_6$: 651.97; Found 652.90 (M+H).

Example 187

6-{2-(4-Chloro-phenyl)-2-[3-(4-chloro-phenyl)-7-iodo-2,5-dioxo-1,2,3,5-tetrahydro-benzo[e][1,4]diazepin-4-yl]-acetylamino}-hexanoic acid $^1$H NMR (400 MHz, DMSO-d$_6$): δ 11.98 (s, 1H), 10.72 (s, 1H), 8.29–8.15 (m, 1H), 7.77 (d, J=2.0 Hz, 1H), 7.59–7.53 (m, 1H), 7.51–7.42 (m, 4H), 7.13 (d, J=8.8 Hz, 2H), 6.91 (d, J=7.6 Hz, 2H), 6.64 (d, J=8.4 Hz, 1H), 6.41 (s, 1H), 4.98 (s, 1H), 3.20–2.95 (m, 2H), 2.16 (t, J=7.6 Hz, 2H), 1.53–1.31 (m, 4H), 1.26–1.15 (m, 2H). Mass spectrum (LCMS, ESI pos) Calcd. for C$_{29}$H$_{26}$Cl$_2$IN$_3$O$_5$: 693.03; Found 693.82 (M+H).

Example 188

[1-(2-tert-Butoxycarbonylamino-ethyl)-3-(4-chloro-phenyl)-7-iodo-2,5-dioxo-1,2,3,5-tetrahydro-benzo[e][1,4]diazepin-4-yl]-(4-chloro-phenyl)-acetic acid $^1$H NMR (400 MHz, CD$_3$OD): δ 7.94 (d, J=2.0 Hz, 1H), 7.53 (d, J=8.4 Hz, 2H), 7.47 (dd, J=8.4 Hz, 2.0 Hz, 1H), 7.29 (d, J=8.0 Hz, 2H), 6.93 (d, J=8.8 Hz, 2H), 6.73 (dd, J=8.0 Hz, 1.6 Hz, 2H), 6.61 (d, J=8.4 Hz, 1H), 6.50 (s, 1H), 5.27 (s, 1H), 3.55–3.49 (m, 2H), 3.50–3.45 (m, 1H), 3.15–3.10 (m, 1H). Mass spectrum (LCMS, ESI pos) Calcd. for C$_{30}$H$_{28}$Cl$_2$IN$_3$O$_6$: 723.04; Found 723.70 (M+H).

Example 189

(4-Chloro-phenyl)-{7-iodo-2,5-dioxo-3-[5-(3-trifluoromethyl-phenyl)-furan-2-yl]-1,2,3,5-tetrahydro-benzo[e][1,4]diazepin-4-yl}-acetic acid $^1$H NMR (400 MHz, DMSO-d$_6$): δ 8.03 (s, 1H), 7.68–7.56 (m, 4H), 7.57–7.44 (m, 4H), 7.40–7.33 (m, 2H), 6.79 (d, J=8.4 Hz, 1H), 6.73 (s, 1H), 6.48 (d, J=3.2 Hz, 1H), 5.61–5.57 (m, 1H), 5.49 (s, 1H). Mass spectrum (LCMS, ESI pos) Calcd. for C$_{28}$H$_{17}$ClF$_3$IN$_2$O$_5$: 679.98; Found 680.77 (M+H).

Example 190

(4-Chloro-phenyl)-[3-(4-chloro-phenyl)-7-iodo-2,5-dioxo-1-(2-pyridin-2-yl-ethyl)-1,2,3,5-tetrahydro-benzo[e][1,4]diazepin-4-yl]-acetic acid Mass spectrum (LCMS, ESI pos) Calcd. for C$_{30}$H$_{22}$Cl$_2$IN$_3$O$_4$: 685.00; Found 686.18 (M+H).

Example 191

(4-Chloro-phenyl)-[3-(4-chloro-phenyl)-7-iodo-1-methylcarbamoylmethyl-2,5-dioxo-1,2,3,5-tetrahydro-benzo[e][1,4]diazepin-4-yl]-acetic acid $^1$H NMR (400 MHz, DMSO-d$_6$): δ 7.84–7.81 (m, 1H), 7.52–7.46 (m, 3H), 7.33–7.27 (m, 2H), 6.91 (d, J=8.4 Hz, 2H), 6.80 (d, J=8.4 Hz, 1H), 6.69 (d, J=8.8 Hz, 2H), 6.57 (s, 1H), 5.33 (s, 1H), 4.50 (m, 1H). Mass spectrum (LCMS, ESI pos) Calcd. for C$_{26}$H$_{20}$Cl$_2$IN$_3$O$_5$: 650.98; Found 651.94 (M+H).

Example 192

(4-Chloro-phenyl)-[3-(4-difluoromethoxy-phenyl)-7-iodo-2,5-dioxo-1,2,3,5-tetrahydro-benzo[e][1,4]diazepin-4-yl]-acetic acid $^1$H NMR (400 MHz, CD$_3$OD): δ 7.93 (d, J=2.0 Hz, 0.6H), 7.89 (d, J=2.0 Hz, 0.4H), 7.59 (d, J=8.0 Hz, 1H), 7.54–7.48 (m, 1H), 7.45 (d, J=8.4 Hz, 0.6H), 7.37–7.30 (m, 2.4H), 7.13–7.05 (m, 0.4H), 6.85 (d, J=8.4 Hz, 0.6H), 6.82–6.70 (m, 2.3H), 6.68–6.65 (m, 0.6H), 6.64–6.58 (m, 1H), 5.70 (s, 0.3H), 5.37 (s, 1H). Mass spectrum (LCMS, ESI pos) Calcd. for C$_{24}$H$_{16}$ClF$_2$IN$_2$O$_5$: 611.98; Found 612.80 (M+H).

Example 193

[1-(2-tert-Butoxycarbonylamino-ethyl)-3-(4-chloro-phenyl)-7-iodo-2,5-dioxo-1,2,3,5-tetrahydro-benzo[e][1,4]diazepin-4-yl]-(4-chloro-phenyl)-acetic acid $^1$H NMR (400 MHz, CD$_3$OD): δ 7.84 (d, J=2.0 Hz, 1H), 7.57–7.45 (m, 3H), 7.37 (d, J=8.4 Hz, 2H), 7.12 (d, J=8.4 Hz, 2H), 7.00 (d, J=8.8 Hz, 2H), 6.82 (d. J=8.8 Hz, 1H), 6.56 (s, 1H), 5.76 (s, 1H), 4.11–3.98 (m, 1H), 3.78–3.65 (m, 1H), 3.16–3.08 (m, 2H), 1.39 (s, 9H). Mass spectrum (LCMS, ESI pos) Calcd. for C$_{30}$H$_{28}$Cl$_2$IN$_3$O$_6$: 723.04; Found 745.90 (M+Na)

Example 194

(3-Benzofuran-2-yl-7-iodo-2,5-dioxo-1,2,3,5-tetrahydro-benzo[e][1,4]diazepin-4-yl)-(4-chloro-phenyl)-acetic acid $^1$H NMR (400 MHz, CD$_3$OD): δ 8.01 (d, J=1.6 Hz, 1H), 7.64 (d, J=8.8 Hz, 2H), 7.58–7.51 (m, 1H), 7.49–7.44 (m, 1H), 7.40–7.32 (m, 2H), 7.26–6.95 (m, 4H), 6.83–6.72 (m, 1H), 5.92 (s, 0.7H), 5.80 (s, 0.3H), 5.64 (s 0.3H), 5.56 (s, 0.7H). Mass spectrum (LCMS, ESI pos) Calcd. for C$_{25}$H$_{16}$ClIN$_2$O$_5$: 585.98; Found 586.93 (M+H).

Example 195

(4-Chloro-phenyl)-[3-(4-chloro-phenyl)-7-iodo-1-methyl-2,5-dioxo-1,2,3,5-tetrahydro-benzo[e][1,4]diazepin-4-yl]-acetic acid $^1$H NMR (400 MHz, CD$_3$OD): δ 7.84 (d, J=2.0 Hz, 1H), 7.62–7.54 (m, 3H), 7.34 (d, J=8.4 Hz, 2H), 6.95 (d, J=8.8 Hz, 2H), 6.82 (d, J=8.8 Hz, 1H), 6.68 (dd, J=8.8 Hz, 1.2 Hz, 2H), 6.53 (s, 1H), 5.38 (s, 1H), 3.44 (s, 3H). Mass spectrum (LCMS, ESI pos) Calcd. for C$_{24}$H$_{17}$Cl$_2$IN$_2$O$_4$: 593.96; Found 594.95 (M+H).

Example 196

(4-Chloro-phenyl)-[3-(4-cyano-phenyl)-7-iodo-2,5-dioxo-1,2,3,5-tetrahydro-benzo[e][1,4]diazepin-4-yl]-acetic acid $^1$H NMR (400 MHz, CD$_3$OD): δ 7.91 (d, J=2.0 Hz, 1H), 7.59 (d, J=8.4 Hz, 1H), 7.55–7.42 (m, 3H), 7.39–7.27 (m, 3H), 6.98 (d, J=8.4 Hz, 1H), 6.65 (d, J=7.6 Hz, 1H), 6.59 (d, J=8.4 Hz, 0.5H), 6.51 (d, J=8.8 Hz, 0.5H), 5.77 (s, 0.5H), 5.44 (s, 0.5H).
Mass spectrum (LCMS, ESI pos) Calcd. for C$_{24}$H$_{15}$ClIN$_3$O$_4$: 570.98; Found 571.80 (M+H).

Example 197

[1-Carboxymethyl-3-(4-chloro-phenyl)-7-iodo-2,5-dioxo-1,2,3,5-tetrahydro-benzo[e][1,4]diazepin-4-yl]-(4-chloro-phenyl)-acetic acid methyl ester $^1$H NMR (400 MHz, DMSO-d$_6$): δ 7.73–6.75 (m, 11H), 6.24 (s, 1H), 5.42 (s, 1H), 4.53–4.25 (m, 1H), 4.16–3.86 (m, 1H), 3.78 (s, 3H). Mass spectrum (LCMS, ESI pos) Calcd. for C$_{26}$H$_{19}$Cl$_2$IN$_2$O$_6$: 651.97; Found 652.87 (M+H).

Example 198

(4-Chloro-phenyl)-[3-(4-chloro-phenyl)-7-(2-hydroxy-ethyl)-2,5-dioxo-1,2,3,5-tetrahydro-benzo[e][1,4]diazepin-4-yl]-acetic acid $^1$H NMR (400 MHz, DMSO-d$_6$): δ 10.46 (s, 1H), 7.62–7.26 (m, 4H), 7.08–6.96 (m, 3H), 6.82–6.66 (m, 3H), 6.30 (s, 1H), 5.29 (s, 1H), 4.59 (s, 1H), 3.45–3.39 (m, 2H), 2.55 (t, J=8.8 Hz, 2H). Mass spectrum (LCMS, ESI pos) Calcd. for C$_{25}$H$_{20}$Cl$_2$N$_2$O$_5$: 498.07; Found 498.95 (M+H).

Example 199

(4-Chloro-phenyl)-[3-(4-chloro-phenyl)-1-(2(R),3-dihydroxy-propyl)-7-iodo-2,5-dioxo-1,2,3,5-tetrahydro-benzo[e][1,4]diazepin-4-yl]-acetic acid Mass spectrum (LCMS, ESI pos) Calcd. for C$_{26}$H$_{21}$Cl$_2$IN$_2$O$_6$: 653.98; Found 654.81 (M+H).

Example 200

(4-Chloro-phenyl)-[3-(6-chloro-pyridin-3-yl)-7-iodo-2,5-dioxo-1,2,3,5-tetrahydro-benzo[e][1,4]diazepin-4-yl]-acetic acid $^1$H NMR (400 MHz, CD$_3$OD): δ 7.63–7.57 (m, 2H), 7.30 (d, J=8.4 Hz, 2H), 7.00–6.89 (m, 3H), 6.78–6.65 (m, 4H), 5.41 (s, 1H).

Example 201

(4-Chloro-phenyl)-[3-(4-chloro-phenyl)-7-hydroxymethyl-2,5-dioxo-1,2,3,5-tetrahydro-benzo[e][1,4]diazepin-4-yl]-acetic acid $^1$H NMR (400 MHz, DMSO-d$_6$): δ 10.52 (s, 1H), 7.57–7.42 (m, 2H), 7.41–7.23 (m, 3H), 7.22–6.96 (m, 4H), 6.87–6.67 (m, 3H), 6.33 (s, 1H), 5.18 (s, 1H), 4.38–4.27 (m, 2H).
Mass spectrum (LCMS, ESI pos) Calcd. for C$_{24}$H$_{18}$Cl$_2$N$_2$O$_5$: 484.06; Found 485.00 (M+H).

Example 202

(4-Chloro-phenyl)-{7-iodo-2,5-dioxo-3-[4-(1,1,2,2-tetrafluoro-ethoxy)-phenyl]-1,2,3,5-tetrahydro-benzo[e][1,4]diazepin-4-yl}-acetic acid $^1$H NMR (400 MHz, CD$_3$OD): δ 7.96 (d, J=2.0 Hz, 0.4H), 7.80 (d, J=2.0 Hz, 0.6H), 7.54–7.47 (m, 1H), 7.39 (d, J=8.4 Hz, 2H), 7.29–7.12 (m, 5H), 7.06 (d, J=8.4 Hz, 2H), 6.85 (t, J=8.0 Hz, 1.8H), 6.62 (s, 0.7H), 5.96 (s, 0.6H), 5.79 (s, 0.4H), 5.36–5.28 (m, 1H). Mass spectrum (LCMS, ESI pos) Calcd. for C$_{25}$H$_{16}$ClF$_4$IN$_2$O$_5$: 661.97; Found 662.90 (M+H).

Example 203

(4-Chloro-phenyl)-[7-iodo-3-(4-methylsulfanyl-phenyl)-2,5-dioxo-1,2,3,5-tetrahydro-benzo[e][1,4]diazepin-4-yl]-acetic acid $^1$H NMR (400 MHz, CD$_3$OD): δ 7.92 (s, 0.7H), 7.88 (s, 0.3H), 7.58 (d, J=8.0 Hz, 1H), 7.56–7.41 (m, 1.7H), 7.38=7.29 (m, 1.7H), 7.20 (d, J=8.0 Hz, 0.7H), 7.08 (d, J=8.0 $_{Hz}$, 0.3H), 7.02–6.89 (m, 1H), 6.86–6.69 (m, 1H), 6.70–6.63 (m, 1.3H), 6.60 (d, J=8.8 Hz, 0.7H), 6.51 (d, J=8.8 Hz, 0.3H), 5.70 (s, 0.3H), 5.35 (s, 0.7H), 2.34 (s, 1H), 2.29 (s, 2H). Mass spectrum (LCMS, ESI pos) Calcd. for C$_{24}$H$_{18}$ClIN$_2$O$_4$S: 591.97; Found 592.90 (M+H).

Example 204

(4-Chloro-phenyl)-[7-iodo-2,5-dioxo-3-(4-pyrrolidin-1-yl-phenyl)-1,2,3,5-tetrahydro-benzo[e][1,4]diazepin-4-yl]-acetic acid $^1$H NMR (400 MHz, CD$_3$OD): δ 8.18–8.08 (m, 1H), 7.98–7.85 (m, 1H), 7.59 (d, J=1.2 Hz, 1H), 7.52–7.42 (m, 2H), 7.39–7.28 (m, 3H), 7.06 (d, J=8.0 Hz, 1H), 6.74–6.45 (m, 1H), 6.29 (d, J=8.4 Hz, 1H), 6.09 (dd, J=8.0 Hz, 1.2 Hz, 1H), 5.66 (s, 0.5H), 5.36 (s, 0.5H), 3.17–3.02 (m, 4H), 1.99–1.87 (m, 4H). Mass spectrum (LCMS, ESI pos) Calcd. for C$_{27}$H$_{23}$ClIN$_3$O$_4$: 615.04; Found 616.07 (M+H).

Example 205

2-(4-Chloro-phenyl)-2-[3-(4-chloro-phenyl)-7-iodo-2,5-dioxo-1,2,3,5-tetrahydro-benzo[e][1,4]diazepin-4-yl]-N,N-bis-(2-hydroxy-ethyl)-acetamide $^1$H NMR (400 MHz, DMSO-d$_6$): δ 8.65 (s, 0.5H), 8.20 (s, 0.5H), 8.00 (d, J=1,6 Hz, 0.5H), 7.94 (d, J=2.0 Hz, 0.5H), 7.52–7.42 (m, 2.5H), 7.37 (d, J=8.8 Hz, 1H), 7.24 (dd, J=5.6 Hz, 1h), 7.10–6.99 (m, 2H), 6.95 (s, 1H), 6.85 (d, J=8.0 Hz, 0.5H), 6.46–6.35 (m, 1H), 5.32 (s, 0.5H), 5.12 (s, 0.5H), 4.04–3.06 (m, 8H). Mass spectrum (LCMS, ESI pos) Calcd. for C$_{27}$H$_{24}$Cl$_2$IN$_3$O$_5$: 667.01; Found 667.85 (M+H).

Example 206

(4-Chloro-phenyl)-{7-iodo-2,5-dioxo-3-[4-(1,1,2,2-tetrafluoro-ethoxy)-phenyl]-1,2,3,5-tetrahydro-benzo[e][1,4]diazepin-4-yl}-acetic acid $^1$H NMR (400 MHz, CD$_3$OD): δ 7.83–7.74 (m, 0.7H), 7.60 (d, J=8.4 Hz, 0.6H), 7.52–7.45 (m, 0.7H), 7.42–7.30 (m, 2H), 7.27 (d, J=8.4 Hz, 1H), 7.17 (d, J=7.6 Hz, 2H), 7.09–6.97 (m, 3H), 6.89–6.78 (m, 2H), 6.63 (s, 0.6H), 6.46 (s, 0.4H), 5.97 (s, 0.5H), 5.60–5.51 (m, 0.6H), 5.37–5.27 (m, 0.7H), 4.66–4.58 (m, 0.5H). Mass spectrum (LCMS, ESI pos) Calcd. for C$_{25}$H$_{16}$ClF4IN$_2$O$_5$: 661.97; Found 662.89 (M+H).

Example 207

[3-(4-Chloro-phenyl)-7-iodo-2,5-dioxo-1,2,3,5-tetrahydro-benzo[e][1,4]diazepin-4-yl]-(6-methyl-pyridin-3-yl)-acetic acid $^1$H NMR (400 MHz, DMSO-d$_6$): δ 10.76 (s, 1H), 8.53 (d, J=2.0 Hz, 1H), 7.78–7.72 (m, 2H), 7.60–7.53 (m, 1H), 7.26–7.16 (m, 3H), 7.10–7.03 (m, 2H), 6.65 (d, J=8.8 Hz, 1H), 6.16 (s, 1H), 5.33 (s, 1H), 2.42 (s, 3H). Mass spectrum (LCMS, ESI pos) Calcd. for $C_{23}H_{17}ClIN_3O_4$: 561.00; Found 562.01 (M+H).

Example 208

3-{2-(4-Chloro-phenyl)-2-[3-(4-chloro-phenyl)-7-iodo-2,5-dioxo-1,2,3,5-tetrahydro-benzo[e][1,4]diazepin-4-yl]-acetylamino}-propionic acid methyl ester $^1$H NMR (400 MHz, DMSO-d$_6$): δ 10.74 (s, 1H), 8.35 (t, J=6.0 Hz, 1H), 7.77 (d, J=2.0 Hz, 1H), 7.61–7.51 (m, 1H), 7.45 (s, 2H), 7.13 (d, J=8.4 Hz, 2H), 6.91 (d, J=7.8 Hz 2H), 6.64 (d, J=7.8 Hz, 1H), 6.42 (s, 1H), 4.98 (s, 1H), 3.56 (s, 3H), 3.48–3.36 (m, 1H), 3.31–3.21 (m, 1H), 2.48–2.40 (m, 2H). Mass spectrum (LCMS, ESI pos) Calcd. for $C_{27}H_{22}Cl_2IN_3O_5$: 665.00; Found 665.70 (M+H).

Example 209

[7-Amino-3-(4-chloro-phenyl)-2,5-dioxo-1,2,3,5-tetrahydro-benzo[e][1,4]diazepin-4-yl]-(4-chloro-phenyl)-acetic acid $^1$H NMR (400 MHz, DMSO-d$_6$): δ 12.00 (s, 1H), 10.20 (s, 1H), 7.53–7.35 (m, 3H), 7.27 (d, J=8.4 Hz, 0.4H), 7.19–6.96 (m, 2.8H), 6.88–6.66 (m, 1.2H0, 6.54–6.39 (m, 1.4H), 6.10 (s, 0.7H), 5.18 (s, 0.8H), 5.00 (s, 1.0H), 4.42 (s, 0.4H). Mass spectrum (LCMS, ESI pos) Calcd. for $C_{23}H_{17}Cl_2N_3O_4$: 469.06; Found 470.00 (M+H).

Example 210

2-(4-Chloro-phenyl)-2-[3-(4-chloro-phenyl)-7-iodo-2,5-dioxo-1,2,3,5-tetrahydro-benzo[e][1,4]diazepin-4-yl]-N-(2-hydroxyguanidino-ethyl)-acetamide $^1$H NMR (400 MHz, DMSO-d$_6$): δ 10.95 (s, 1H), 10.75 (s, 1H), 8.41 (m, 1H), 7.77 (d, J=2.0 Hz, 1H), 7.57 (dd, J=8.4 Hz, 2.4 Hz, 1H), 7.53–7.44 (m, 3H), 7.14 (d, J=8.8 Hz, 2H), 6.93 (d, J=8.4 Hz, 2H), 6.65 (d, J=8.8 Hz 1H), 6.43 (s, 1H), 4.99 (s, 1H), 3.80 (t, J=5.6 Hz, 2H), 3.46–3.36 (m, 4H). Mass spectrum (LCMS, ESI pos) Calcd. for $C_{26}H_{23}Cl_2IN_6O_4$: 680.02; Found 681.00 (M+H).

Example 211

(4-Chloro-phenyl)-[3-(5-chloro-thiophen-2-yl)-7-iodo-2,5-dioxo-1,2,3,5-tetrahydro-benzo[e][1,4]diazepin-4-yl]-acetic acid $^1$H NMR (400 MHz, CD$_3$OD): δ 7.99–7.89 (m, 1H), 7.67–7.51 (m, 2H), 7.44–7.32 (m, 2H), 7.27–6.99 (m, 1H), 6.90–6.82 (m, 0.5H), 6.73 (d, J=8.4 Hz, 0.5H), 6.67–6.41 (m, 2H), 6.23–6.18 (m, 0.5H), 5.44–5.38 (m, 0.5H). Mass spectrum (LCMS, ESI pos) Calcd. for $C_{21}H_{13}Cl_2IN_2O_4S$: 585.90; Found 586.72 (M+H).

Example 212

(4-Chloro-phenyl)-[7-iodo-3-(4-isopropenyl-cyclohex-1-enyl)-2,5-dioxo-1,2,3,5-tetrahydro-benzo[e][1,4]diazepin-4-yl]-acetic acid $^1$H NMR (400 MHz, DMSO-d$_6$): δ 10.31 (s, 0.8H), 10.15 (s, 0.2H), 7.93–7.78 (m, 1H), 7.72–7.64 (m, 1H), 7.44–7.24 (m, 4H), 6.83–6.73 (m, 2H), 6.20–6.11 (m, 1H), 5.05–4.93 (m, 1H), 4.57–4.44 (m, 2H), 4.35–4.24 (m, 1H), 1.71–1.21 (m, 10H). Mass spectrum (LCMS, ESI pos) Calcd. for $C_{26}H_{24}ClIN_2O_4$: 590.05; Found 591.00 (M+H).

Example 213

(4-Chloro-phenyl)-[3-(4-chloro-phenyl)-1-(2(S),3-dihydroxy-propyl)-7-iodo-2,5-dioxo-1,2,3,5-tetrahydro-benzo[e][1,4]diazepin-4-yl]-acetic acid $^1$H NMR (400 MHz, CD$_3$OD): δ 7.87–7.80 (m, 1H), 7.61–7.45 (m, 3H), 7.38–7.28 (m, 2H), 7.19–6.91 (m, 4H), 6.80–6.71 (m, 1H), 6.62 (s, 0.3H), 5.89 (s, 0.6H), 4.30–3.38 (m, 5H). Mass spectrum (LCMS, ESI pos) Calcd. for $C_{26}H_{21}Cl_2IN_2O_6$: 653.98; Found 637.20.

Example 214

5-[4-[Carboxy-(4-chloro-phenyl)-methyl]-3-(4-chloro-phenyl)-7-iodo-2,5-dioxo-2,3,4,5-tetrahydro-benzo[e][1,4]diazepin-1-yl]-pentanoic acid $^1$H NMR (400 MHz, DMSO-d$_6$): δ 7.97–7.91 (m, 1H), 7.66 (d, J=8.4 Hz, 1H), 7.46–7.41 (m, 4H), 7.03 (d, J=8.4 Hz, 2H), 6.73 (d, J=8.4 Hz, 1H), 6.67 (s, 1H), 6.64 (d, J=8.4 Hz, 2H), 5.48 (s, 1H), 4.57–4.45 (m, 1H), 3.75–3.65 (m, 1H), 2.49–2.39 (m, 2H), 1.75–1.55 (m, 4H). Mass spectrum (LCMS, ESI pos) Calcd. for $C_{28}H_{23}Cl_2IN_2O_6$: 680.00; Found 680.85 (M+H).

Example 215

5-{3-(4-Chloro-phenyl)-4-[1-(4-chloro-phenyl)-2-hydroxy-ethyl]-7-iodo-2,5-dioxo-2,3,4,5-tetrahydro-benzo[e][1,4]diazepin-1-yl}-pentanoic acid $^1$H NMR (400 MHz, DMSO-d$_6$): δ 7.85 (d, J=2 Hz, 1H), 7.61–7.52 (m, 3H), 7.38 (d, J=8.4 Hz, 2H), 6.97–6.87 (m, 3H), 6.58 (dd, J=2.0 Hz, 8.0 Hz, 2H), 6.28–6.20 (m, 1H), 5.39 (s, 1H), 4.36–4.24 (m, 2H), 4.20–4.12 (m, 1H), 3.83–3.72 (m, 1H), 2.23–2.11 (m, 2H), 1.84–1.65 (m, 2H), 1.64–1.52 (m, 2H). Mass spectrum (LCMS, ESI pos) Calcd. for $C_{28}H_{25}Cl_2IN_2O_5$: 666.02; Found 666.97 (M+H).

Example 216

5-{3-(4-Chloro-phenyl)-4-[(4-chloro-phenyl)-diethylcarbamoyl-methyl]-7-iodo-2,5-dioxo-2,3,4,5-tetrahydro-benzo[e][1,4]diazepin-1-yl}-pentanoic acid $^1$H NMR (400 MHz, DMSO-d$_6$): δ 7.65 (d, J=2.4 Hz, 1H), 7.62–7.55 (m, 3H), 7.53–7.48 (m, 2H), 7.12–7.06 (m, 2H), 6.94–6.87 (m, 2H), 6.60 (s, 1H), 4.89 (s, 1H), 4.24–4.14 (m, 1H), 3.74–3.63 (m, 1H), 3.57–3.47 (m, 2H), 3.17–3.08 (m, 2H), 2.23–2.13 (m, 2H), 1.85–1.73 (m, 1H), 1.67–1.58 (m, 1H), 1.49–1.40 (m, 2H), 1.10–0.98 (m, 6H). Mass spectrum (LCMS, ESI pos) Calcd. for $C_{32}H_{32}Cl_2IN_3O_5$: 735.08; Found 735.82 (M+H).

Example 217

Fluorescent Peptide Assay

The inhibition of MDM2 binding to p53 was measured using a p53 peptide analogue binding to MDM2 residues 17–125. The published crystal structure of this complex (Kussie et al., *Science* 274:948–953 (1996)) validates this fragment as containing the p53 binding site, and we have solved the x-ray structure of the p53 peptide analogue MPRFMDYWEGLN, described to be a peptide inhibitor of the MDM2 p53 interaction (Bottger et al., *J. Mol. Biol.* 269:744–756 (1997)). The assay uses N terminal fluorescein RFMDYWEGL peptide (Fl 9 mer).

The mdm2 17–125 was produced as a glutathione S transferase fusion as follows: cDNA encoding residues 17–125 were cloned into pGEX4t-3 (Pharmacia) as follows. PCR was performed using ATCC item number 384988 containing partial human mdm2 sequence as template and the following primers: Forward: 5'-CTC TCT C GGATCCCA GAT TCC AGC TTC GGA ACA AGA G; Reverse: 5'-TAT ATA TCTCGAGTC AGT TCT CAC TCA CAG ATG TAC CTG AG. The PCR product was then digested with BamHI and XhoI (sequence recognition sites underlined in primers), gel purified, and ligated into pGEX4t-3 which had also been digested with BamHI and XhoI. Plasmids were transfected into *E. coli* X90 strain, grown to an OD of 1.0 in TB 0.2% glucose 100 μg/mL ampicillin and induced with 1 mM IPTG. Cells were harvested 5 hours post induction, centrifuged, and resuspended in PBS 10 mL/g cell paste. Cells were lysed in an Avestin microfluidizer, centrifuged, and the supernatant bound to a glutathione sepharose 4B resin (Pharmacia). The resin was washed with PBS and the MDM2 17–125 cleaved from the GST by the addition of 2 μg/mL thrombin (Enzyme Research Labs). The cleaved MDM2 was further purified on Sepharose SP Fast Flow resin (Pharmacia), eluting with 20 mM HEPES pH 7.5 150 mM NaCl. Glutathione was added to 5 mM, and the protein stored at −70° C.

Test compound was incubated for 15 minutes with 30 nM fluorescein peptide Fl 9 mer and 120 nM MDM2 17–125 in 50 mM HEPES pH 7.5, 150 mM NaCl, 3 mM octyl glucoside. The polarization of the fluorescein label was thereafter measured by excitation at 485 nm and emission at 530 nm. Polarization was expressed as a percent of a no compound control, using buffer with Fl 9 mer but without MDM2 as background.

Compounds of the present invention inhibited the binding of p53 to MDM2. The potency of the compounds was measured as $IC_{50}$, which is a measure of the concentration of the test compound required to inhibit 50% binding between MDM2 and p53. The $IC_{50}$ values for compounds of the present invention ranged from 0.1 μM to >100 μM. Table 1 provides representative data for compounds of the invention.

TABLE 1

Inhibition of MDM2 binding to p53

| Example No. | $IC_{50}$ (μM) |
|---|---|
| 1 | 1.7 |
| 4 | 1.8 |
| 10 | 13 |
| 12 | 56 |
| 27 | 7.8 |
| 32 | 10.1 |
| 39 | 11.7 |
| 46 | 10.5 |
| 56 | 1.9 |
| 74 | 10 |
| 88 | 0.87 |
| 102 | 1.7 |
| 111 | 0.58 |
| 125 | 0.62 |
| 130 | 0.47 |
| 145 | 0.62 |

Example 218

Tablet Preparation

Tablets containing 25.0, 50.0, and 100.0 mg, respectively, of the compound of Example 1 ("active compound") are prepared as illustrated below:

TABLET FOR DOSES CONTAINING FROM 25–100 MG OF THE ACTIVE COMPOUND

| | Amount-mg | | |
|---|---|---|---|
| Active compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

Example 219

Intravenous Solution Preparation

An intravenous dosage form of the compound of Example 1 ("active compound") is prepared as follows:

| | |
|---|---|
| Active compound | 0.5–10.0 mg |
| Sodium citrate | 5–50 mg |
| Citric acid | 1–15 mg |
| Sodium chloride | 1–8 mg |
| Water for injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Having now fully described this, invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound of Formula I:

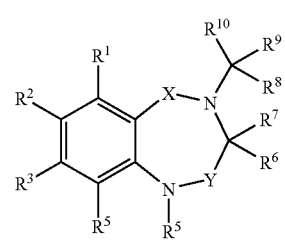

or pharmaceutically acceptable salt thereof; wherein:

X and Y are independently —C(O)—, —CH$_2$— or —C(S)—;

$R^1$, $R^3$, and $R^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or $R^3$ and $R^4$ are taken together to form —(CH$_2$)$_u$—, where u is 3–6, —CH=CH—CH=CH— or —CH$_2$CH=CHCH$_2$—;

$R^2$ is hydrogen, halo, $C_{1-4}$ alkyl, $C_{3-7}$ cycloalkyl, $C_{2-6}$ alkenyl, $C_{2-6}$ alkynyl, acetylamino, $C_{1-6}$ alkoxy, phenyl, halophenyl, hydroxyphenyl, $C_{1-6}$ alkoxyphenyl, $C_{1-6}$ alkylphenyl, aminophenyl, $C_{1-6}$ alkylenedioxyphenyl, hydroxycarbonylphenyl, thienyl, $C_{1-6}$ alkylthienyl, furanyl, pyrrolyl, amino, $C_{1-6}$ hydroxyalkyl or cyano;

$R^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

$R^6$ is cycloalkyl, aryl, heteroaryl, cycloalkylalkyl, heteroarylalkyl, or a saturated or partially unsaturated heterocycle, each of which is optionally substituted;

$R^7$ and $R^8$ are independently hydrogen or alkyl;

$R^9$ is cycloalkyl, aryl, heteroaryl, a saturated or partially unsaturated heterocycle, cycloalkyl(alkyl), aralkyl or heteroarylalkyl, each of which is optionally substituted; and $R^{10}$ is —(CH$_2$)$_n$—CO$_2$R$^b$, —(CH$_2$)$_m$—CO$_2$M, —(CH$_2$)$_i$—OH or —(CH$_2$)$_j$—CONR$^c$R$^d$ where $R^b$ is hydrogen, alkyl, optionally substituted cycloalkyl, or optionally substituted, saturated or partially unsaturated heterocycle;

M is a cation;

$R^c$ and $R^d$ are independently hydrogen, alkyl, hydroxyalkyl, carboxyalkyl, aminoalkyl, optionally substituted cycloalkyl, optionally substituted aryl, optionally substituted aralkyl, optionally substituted heteroaryl, optionally substituted heteroarylalkyl, and an optionally substituted, saturated or partially unsaturated heterocycle; and n is 0–8, m is 0–8, i is 1–8 and j is 0–8.

2. A compound of Formula I:

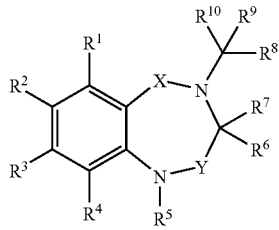

I or pharmaceutically acceptable salt thereof; wherein:

X and Y are independently —C(O)—, —CH$_2$— or —C(S)—;

$R^1$, $R^3$, and $R^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or $R^3$ and $R^4$ are taken together to form —(CH$_2$)$_u$—, where u is 3–6, —CH=CH—CH=CH— or —CH$_2$CH=CHCH$_2$—;

$R^2$ is iodo, fluoro, chloro, bromo, methyl, ethyl, propyl, isopropyl, t-butyl, sec-butyl, cyclopropyl, ethynyl, acetylamino, methoxy, 3-chlorophenyl, 4-chlorophenyl, 4-hydroxyphenyl, 3-methoxyphenyl, 4-methylphenyl, 3-methylphenyl, 3-isopropylphenyl, 3-aminophenyl, 3,4-methylenedioxyphenyl, 4-hydroxycarbonylphenyl thien-3-yl, 4-methylthien-2-yl, furan-2-yl, 1H-pyrrol-3-yl, amino, 2-hydroxyethyl, hydroxymethyl, furan-3-yl, or vinyl;

$R^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

$R^6$ is cycloalkyl, aryl, heteroaryl, cycloalkylalkyl, heteroarylalkyl, or a saturated or partially unsaturated heterocycle, each of which is optionally substituted;

$R^7$ and $R^8$ are independently hydrogen or alkyl;

$R^9$ is cycloalkyl, aryl, heteroaryl, a saturated or partially unsaturated heterocycle, cycloalkyl(alkyl), aralkyl or heteroarylalkyl, each of which is optionally substituted; and $R^{10}$ is —(CH$_2$)$_n$—CO$_2$R$^b$, —(CH$_2$)$_m$—CO$_2$M, —(CH$_2$)$_i$—OH or —(CH$_2$)$_j$—CONR$^c$R$^d$ where $R^b$ is hydrogen, alkyl, optionally substituted cycloalkyl, or optionally substituted, saturated or partially unsaturated heterocycle;

M is a cation;

$R^c$ and $R^d$ are independently hydrogen, alkyl, hydroxyalkyl, carboxyalkyl, aminoalkyl, optionally substituted cycloalkyl, optionally substituted aryl, optionally substituted aralkyl, optionally substituted heteroaryl, optionally substituted heteroarylalkyl, and an optionally substituted, saturated or partially unsaturated heterocycle; and n is 0–8, m is 0–8, i is 1–8 and j is 0–8.

3. The compound of claim 1, wherein $R^2$ is halo or phenyl.

4. The compound of claim 3, wherein $R^2$ is iodo.

5. A compound of Formula I:

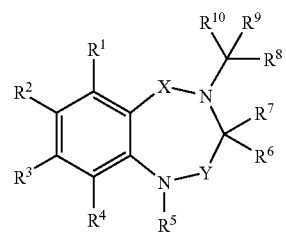

I or pharmaceutically acceptable salt thereof; wherein:

X and Y are independently —C(O)—, —CH$_2$— or —C(S)—;

$R^1$, $R^2$, and $R^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or $R^1$ and $R^2$ are taken together to form —$(CH_2)_u$—, where u is 3–6, —CH=CH—CH=CH— or —$CH_2$CH=CHCH$_2$—;

$R^3$ is hydrogen, alkyl, phenyl, fluoro, chloro, iodo or methyl;

$R^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

$R^6$ is cycloalkyl, aryl, heteroaryl, cycloalkylalkyl, heteroarylalkyl, or a saturated or partially unsaturated heterocycle, each of which is optionally substituted;

$R^7$ and $R^8$ are independently hydrogen or alkyl;

$R^9$ is cycloalkyl, aryl, heteroaryl, a saturated or partially unsaturated heterocycle, cycloalkyl(alkyl), aralkyl or heteroarylalkyl, each of which is optionally substituted; and $R^{10}$ is —$(CH_2)_n$—$CO_2R^b$, —$(CH_2)_m$—$CO_2M$, —$(CH_2)_i$—OH or —$(CH_2)_j$—CONR$^c$R$^d$ where $R^b$ is hydrogen, alkyl, optionally substituted cycloalkyl, or optionally substituted, saturated or partially unsaturated heterocycle;

M is a cation;

$R^c$ and $R^d$ are independently hydrogen, alkyl, hydroxyalkyl, carboxyalkyl, aminoalkyl, optionally substituted cycloalkyl, optionally substituted aryl, optionally substituted aralkyl, optionally substituted heteroaryl, optionally substituted heteroarylalkyl, and an optionally substituted, saturated or partially unsaturated heterocycle; and n is 0–8, m is 0–8, i is 1–8 and j is 0–8.

6. The compound of claim 5, wherein $R^3$ is hydrogen.

7. A compound of Formula I:

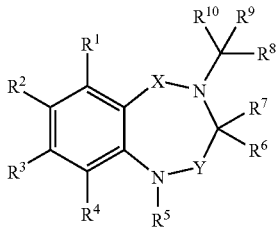

I or pharmaceutically acceptable salt thereof; wherein:

X and Y are independently —C(O)—, —$CH_2$— or —C(S)—;

$R^1$, $R^2$, $R^3$, and $R^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or $R^1$ and $R^2$, or $R^2$ and $R^3$, -or $R^3$ and $R^4$ are taken together to form —$(CH_2)_u$—, where u is 3–6, —CH=CH—CH=CH— or —$CH_2$CH=CHCH$_2$—;

$R^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

$R^6$ is trifluoromethylphenyl, halophenyl, $C_{1-6}$ alkoxyphenyl, halo($C_{1-4}$)alkoxyphenyl, naphthyl, benzyloxyphenyl, phenoxyphenyl, dihydrobenzodioxinyl, trifluoromethyl-halophenyl, pyridyl, thienyl, $C_{1-6}$ alkylthienyl, halothienyl, bithienyl, $C_{1-6}$ alkylbenzothienyl, (halophenyl)furanyl, quinolinyl, biphenyl, indolyl, (trifluoromethylsulfanyl)phenyl, (trifluoromethylphenyl)furanyl, halo($C_{1-4}$)alkoxyphenyl, benzofuranyl, cyanophenyl, halopyridyl, (methylsulfanyl)phenyl, pyrrolidinylphenyl, $C_{2-6}$ alkenyl($C_{3-7}$)cycloalkenyl, cubanyl or halocubanyl;

$R^7$ and $R^8$ are independently hydrogen or alkyl;

$R^9$ is cycloalkyl, aryl, heteroaryl, a saturated or partially unsaturated heterocycle, cycloalkyl(alkyl), aralkyl or heteroarylalkyl, each of which is optionally substituted; and $R^{10}$ is —$(CH_2)_n$—$CO_2R^b$, —$(CH_2)_m$—$CO_2M$, —$(CH_2)_i$—OH or —$(CH_2)_j$—CONR$^c$R$^d$ where $R^b$ is hydrogen, alkyl, optionally substituted cycloalkyl, or optionally substituted, saturated or partially unsaturated heterocycle;

M is a cation;

$R^c$ and $R^d$ are independently hydrogen, alkyl, hydroxyalkyl, carboxyalkyl, aminoalkyl, optionally substituted cycloalkyl, optionally substituted aryl, optionally substituted aralkyl, optionally substituted heteroaryl, optionally substituted heteroarylalkyl, and an optionally substituted, saturated or partially unsaturated heterocycle; and n is 0–8, m is 0–8, i is 1–8 and j is 0–8.

8. A compound of Formula I:

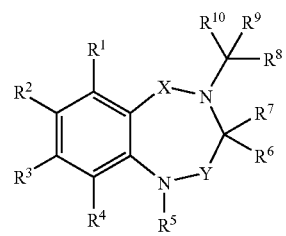

I or pharmaceutically acceptable salt thereof; wherein:

X and Y are independently —C(O)—, —$CH_2$— or —C(S)—;

$R^1$, $R^2$, $R^3$, and $R^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or $R^1$ and $R^2$, or $R^2$ and $R^3$, -or $R^3$ and $R^4$ are taken together to form —$(CH_2)_u$—, where u is 3–6, —CH=CH—CH=CH— or —$CH_2$CH=CHCH$_2$—;

$R^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

$R^6$ is 2-trifluoromethylphenyl, 3-trifluoromethylphenyl, 4-trifluoromethylphenyl, 2-chlorophenyl, 3-chlorophenyl, 4-chlorophenyl, 2-bromophenyl, 3-bromophenyl, 4-bromophenyl, 4-iodophenyl, 4-methylphenyl, 4-ethylphenyl, 4-trifluoromethoxyphenyl, 4-isopropylphenyl, phenyl, 4-methoxy-phenyl, naphthalen-2-yl, 4-tert-butylphenyl, 4-benzyloxyphenyl, 4-phenoxyphenyl, 3,4-dichlorophenyl, 3,4-dimethoxyphenyl, 2,3-dihydrobenzo[1,4]dioxin-6-yl, 4-bromo-2-fluorophenyl, 2-fluoro-4-trifluoromethylphenyl, 3-fluoro-4-trifluoromethylphenyl, 4-chloro-3-trifluoromethylphenyl, 4-chloro-3-fluorophenyl, pyrid-2-yl, pyrid-3-yl, pyrid-4-yl, thien-3-yl, 5-methylthien-2-yl, 3-methylthien-2-yl, 4-bromothien-2-yl, 5-[2,2']bithienyl, 3-methylbenzo[b]thiophen-2-yl, 5-(2-chlorophenyl)-furan-2-yl, 5-(3-chlorophenyl)-furan-2-yl, quinolin-3-yl, biphen-4-yl, indol-2-yl, indol-3-yl, 4-trifluoromethylsulfanylphenyl, 5-(3-trifluoromethylphenyl)furan-2-yl, 4-(1,1,2,2-tetrafluoroethoxy)phenyl, 4-difluoromethoxyphenyl, benzofuran-2-yl, 4-cyanophenyl, 6-chloropyrid-3-yl, 4-methylsulfanylphenyl, 4-pyrrolidin-1-ylphenyl, 5-chlorothien-2-yl, 4-isopropenylcyclohex-1-enyl or 1-chlorocuban-4-yl;

$R^7$ and $R^8$ are independently hydrogen or alkyl;

$R^9$ is cycloalkyl, aryl, heteroaryl, a saturated or partially unsaturated heterocycle, cycloalkyl(alkyl), aralkyl or heteroarylalkyl, each of which is optionally substituted; and $R^{10}$ is $—(CH_2)_n—CO_2R^b$, $—(CH_2)_m—CO_2M$, $—(CH_2)_i—OH$ or $—(CH_2)_j—CONR^cR^d$ where $R^b$ is hydrogen, alkyl, optionally substituted cycloalkyl, or optionally substituted, saturated or partially unsaturated heterocycle;

M is a cation;

$R^c$ and $R^d$ are independently hydrogen, alkyl, hydroxyalkyl, carboxyalkyl, aminoalkyl, optionally substituted cycloalkyl, optionally substituted aryl, optionally substituted aralkyl, optionally substituted heteroaryl, optionally substituted heteroarylalkyl, and an optionally substituted, saturated or partially unsaturated heterocycle; and n is 0–8, m is 0–8, i is 1–8 and j is 0–8.

9. The compound of claim 8, wherein $R^6$ is 4-chlorophenyl, 4-bromophenyl, 4-trifluoromethylphenyl or 4-trifluoromethoxyphenyl.

10. The compound of claim 7, wherein $R^6$ is 4-chlorophenyl.

11. A compound of Formula I:

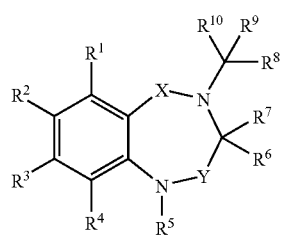

I or pharmaceutically acceptable salt thereof; wherein:

X and Y are independently $—C(O)—$, $—CH_2—$ or $—C(S)—$;

$R^1$, $R^2$, $R^3$, and $R^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or $R^1$ and $R^2$, or $R^2$ and $R^3$, or $R^3$ and $R^4$ are taken together to form $—(CH_2)_u—$, where u is 3–6, $—CH=CH—CH=CH—$ or $—CH_2CH=CHCH_2—$;

$R^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

$R^6$ is cycloalkyl, aryl, heteroaryl, cycloalkylalkyl, hetroarylalkyl, or a saturated or partially unsaturated hetrocycle, each of which is optionally substituted;

$R^9$ is cycloalkyl, aryl, heteroaryl, a saturated or partially unsaturated heterocycle, cycloalkyl(alkyl), aralkyl or heteroarylalkyl, each of which is optionally substituted; and $R^{10}$ is $—(CH_2)_n—CO_2R^b$, $—(CH_2)_m—CO_2M$, $—(CH_2)_i—OH$ or $—(CH_2)_j—CONR^cR^d$ where $R^b$ is hydrogen, alkyl, optionally substituted cycloalkyl, or optionally substituted, saturated or partially unsaturated heterocycle;

M is a cation;

$R^c$ and $R^d$ are independently hydrogen, alkyl, hydroxyalkyl, carboxyalkyl, aminoalkyl, optionally substituted cycloalkyl, optionally substituted aryl, optionally substituted aralkyl, optionally substituted heteroaryl, optionally substituted heteroarylalkyl, and an optionally substituted, saturated or partially unsaturated heterocycle; and n is 0–8, m is 0–8, i is 1–8 and j is 0–8.

12. The compound of claim 11, wherein $R^7$ and $R^8$ are hydrogen.

13. A compound of Formula I:

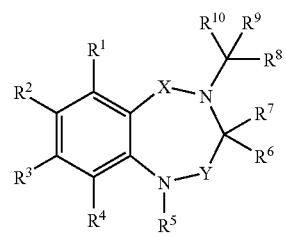

I or pharmaceutically acceptable salt thereof; wherein:

X and Y are independently $—C(O)—$, $—CH_2—$ or $—C(S)—$;

$R^1$, $R^2$, $R^3$, and $R^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or R$^1$ and R$^2$, or R$^2$ and R$^3$, -or R$^3$ and R$^4$ are taken together to form —(CH$_2$)$_u$—, where u is 3–6, —CH=CH—CH=CH— or —CH$_2$CH=CHCH$_2$—;

R$^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

R$^6$ is cycloalkyl, aryl, hetroaryl, cycloalkylalkyl, hetroarylalkyl, or a saturated or partially unsaturated hetrocycle, each of which is optionally substituted;

R$^7$ and R$^8$ are independently hydrogen or alkyl;

wherein R$^9$ is optionally substituted C$_{6-10}$ aryl or optionally substituted C$_{6-10}$ ar(C$_{1-6}$)alkyl;

R$^{10}$ is —(CH$_2$)$_n$—CO$_2$R$^b$, —(CH$_2$)$_m$—CO$_2$M, —(CH$_2$)$_i$—OH or —(CH$_2$)$_j$—CONR$^c$R$^d$ where R$^b$ is hydrogen, alkyl, optionally substituted cycloalkyl, or optionally substituted, saturated or partially unsaturated heterocycle;

M is a cation;

R$^c$ and R$^d$ are independently hydrogen, alkyl, hydroxyalkyl, carboxyalkyl, aminoalkyl, optionally substituted cycloalkyl, optionally substituted aryl, optionally substituted aralkyl, optionally substituted heteroaryl, optionally substituted heteroarylalkyl, and an optionally substituted, saturated or partially unsaturated heterocycle; and n is 0–8, m is 0–8, i is 1–8 and j is 0–8.

14. The compound of claim 13, wherein R$^9$ is phenyl, 4-chlorophenyl, 4-chlorobenzyl, benzyl, cyclohexyl, cyclohexylmethyl, 4-hydroxyphenyl, pyridylmethyl, 4-fluorophenyl, 4-trifluoromethylphenyl, 4-iodobenzyl, 4-bromobenzyl, thien-2-yl, thien-2-ylmethyl, naphth-2-ylmethyl, pyrid-2-ylethyl, 3-methylphenyl, 4-methylphenyl, 4-ethylphenyl, 4-chloro-3-fluorophenyl, 2-fluoro-4-trifluoromethylphenyl, 4-hydroxycarbonylphenyl, naphthalen-2-yl, naphthalen-1-yl, 4-iodophenyl, 4-bromophenyl, 3,4-dichlorophenyl, 2-chlorophenyl, 4-tert-butylphenyl, 4-isopropylphenyl, 3-chlorophenyl, 4-trifluoromethoxyphenyl, 3-hydroxyphenyl, 4-hydroxybenzyl, 4-trifluoromethylbenzyl, naphth-1-ylmethyl, 6-chloropyrid-3-yl, or 6-methylpyrid-3-yl.

15. The compound of claim 13, wherein R$^9$ is halophenyl or halobenzyl.

16. The compound of claim 13, wherein R$^9$ is phenyl or 4-chlorophenyl.

17. A compound of Formula I:

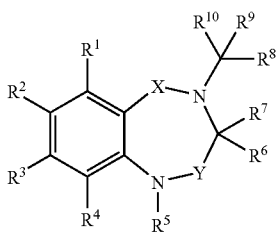

I or pharmaceutically acceptable salt thereof; wherein:

X and Y are independently —C(O)—, —CH$_2$— or —C(S)—;

R$^1$, R$^2$, R$^3$, and R$^4$ are independently hydrogen, halo, alkyl, alkenyl, alkynyl, cycloalkyl, optionally substituted aryl, optionally substituted aralkyl, optionally substituted heteroaryl, optionally substituted heteroaralkyl, alkoxy, optionally substituted aryloxy, optionally substituted heteroaryloxy, cyano, amino, alkanoylamino, nitro, hydroxy, carboxy, or alkoxycarbonyl;

or R$^1$ and R$^2$, or R$^2$ and R$^3$, or R$^3$ and R$^4$ are taken together to form —(CH$_2$)$_u$—, where u is 3–6, —CH=CH—CH=CH— or —CH$_2$CH=CHCH$_2$—;

R$^5$ is hydrogen, alkyl, cycloalkyl, optionally substituted aryl, optionally substituted heteroaryl, optionally substituted aralkyl, optionally substituted heteroaralkyl, carboxyalkyl, alkoxycarbonyl, alkoxycarbonylalkyl, aminocarbonyl, aminocarbonylalkyl, alkylaminocarbonyl or alkylaminocarbonylalkyl;

R$^6$ is cycloalkyl, aryl, hetroaryl, cycloalkylalkyl, hetroarylalkyl, or a saturated or partially unsaturated hetrocycle, each of which is optionally substituted;

R$^7$ and R$^8$ are independently hydrogen or alkyl;

R$^9$ is cycloalkyl, aryl, heteroaryl, a saturated or partially unsaturated heterocycle, cycloalkyl(alkyl), aralkyl or heteroarylalkyl, each of which is optionally substituted; and R$^{10}$ is —COOR$^b$ or —CH$_2$—COOR$^b$, where R$^b$ is hydrogen or C$_{1-6}$ alkyl; or R$^{10}$ is —COOM, or —CH$_2$—COOM, where M is Na$^+$ or K$^+$.

18. The compound of claim 17, wherein R$^{10}$ is —COOR$^b$ or —CH$_2$—COOR$^b$, where R$^b$ is hydrogen, methyl, ethyl, propyl or tert-butyl.

19. The compound of claim 17, wherein R$^{10}$ is —COOH or —COOM, where M is Na$^+$ or K$^+$.

20. The compound of claim 1, wherein R$^{10}$ is —CH$_2$OH or —CH$_2$CH$_2$OH, or —CH$_2$—CONR$^c$R$^d$ or —CONR$^c$R$^d$, where R$^c$ and R$^d$ are independently hydrogen, methyl, ethyl, propyl, t-butyl, hydroxymethyl, hydroxyethyl, hydroxypropyl, aminomethyl, aminoethyl, aminopropyl, carboxymethyl, carboxyethyl, carboxypropyl, cyclopentyl, cyclohexyl, phenyl or benzyl.

21. The compound of claim 1, wherein R$^{10}$ is —CH$^2$—CONR$^c$R$^d$ or —CONR$^c$R$^d$, where R$^c$ and R$^d$ are independently hydrogen, methyl, hydroxyethyl, 3-carboxypropyl, 1-carboxy-2-methylpropyl, hydroxy, 4-carboxybutyl, 5-carboxypentyl, 2-(methoxycarbonyl)ethyl or 2-(hydroxyguanidino)ethyl.

22. The compound of claim 1, wherein said compound is selected from the group consisting of:

(4-chloro-phenyl)-[3-(4-chloro-phenyl)-7-iodo-2,5-dioxo-1,2,3,5-tetrahydro-benzo[e][1,4]diazepin-4-yl]-acetic acid;

2-[7-bromo-3-(4-chloro-phenyl)-2,5-dioxo-1,2,3,5-tetrahydro-benzo[e][1,4]diazepin-4-yl]-3-(4-chloro-phenyl)-propionic acid;

2-(4-chloro-phenyl)-2-[3-(4-chloro-phenyl)-7-iodo-2,5-dioxo-1,2,3,5-tetrahydro-benzo[e][1,4]diazepin-4-yl]-acetamide;

[7-chloro-3-(4-chloro-phenyl)-2,5-dioxo-1,2,3,5-tetrahydro-benzo[e][1,4]diazepin-4-yl]-(4-chloro-phenyl)-acetic acid;

(4-chloro-phenyl)-[3-(4-chloro-phenyl)-7-ethynyl-2,5-dioxo-1,2,3,5-tetrahydro-benzo[e][1,4]diazepin-4-yl]-acetic acid;

[3-(4-chloro-phenyl)-7-iodo-2,5-dioxo-1,2,3,5-tetrahydro-benzo[e][1,4]diazepin-4-yl]-p-tolyl-acetic acid;

(4-chloro-3-fluoro-phenyl)-[3-(4-chloro-phenyl)-7-iodo-2,5-dioxo-1,2,3,5-tetrahydro-benzo[e][1,4]diazepin-4-yl]-acetic acid;

(4-chloro-phenyl)-[3-(4-chloro-phenyl)-7-ethyl-2,5-dioxo-1,2,3,5-tetrahydro-benzo[e][1,4]diazepin-4-yl]-acetic acid;

(4-chloro-phenyl)-[3-(4-chloro-phenyl)-7-isopropyl-2,5-dioxo-1,2,3,5-tetrahydro-benzo[e][1,4]diazepin-4-yl]-acetic acid;

(4-bromo-phenyl)-[3-(4-chloro-phenyl)-7-isopropyl-2,5-dioxo-1,2,3,5-tetrahydro-benzo[e][1,4]diazepin-4-yl]-acetic acid;

[3-(4-chloro-3-fluoro-phenyl)-7-iodo-2,5-dioxo-1,2,3,5-tetrahydro-benzo[e][1,4]diazepin-4-yl]-(4-chloro-phenyl)-acetic acid;

[3-(4-chlorophenyl)-7-phenyl-2,5-dioxo-1,2,3,5-tetrahydro-benzo[e][1,4]diazepin-4-yl]-phenylacetic acid;

[3-(4-chloro-phenyl)-7-iodo-2,5-dioxo-1,2,3,5-tetrahydro-benzo[e][1,4]diazepin-4-yl]-(4-fluoro-phenyl)-acetic acid;

[3-(4-chloro-phenyl)-7-iodo-2,5-dioxo-1,2,3,5-tetrahydro-benzo[e][1,4]diazepin-4-yl]-(4-trifluoromethyl-phenyl)-acetic acid;

(4-chloro-phenyl)-[7-iodo-2,5-dioxo-3-(4-trifluoromethoxy-phenyl)-1,2,3,5-tetrahydrobenzo[e][1,4]diazepin-4-yl]-acetic acid;

(4-chloro-phenyl)-[7-iodo-2,5-dioxo-3-(4-trifluoromethyl-phenyl)-1,2,3,5-tetrahydrobenzo[e][1,4]diazepin-4-yl]-acetic acid;

[3-(4-bromo-phenyl)-7-iodo-2,5-dioxo-1,2,3,5-tetrahydro-benzo[e][1,4]diazepin-4-yl]-(4-chloro-phenyl)-acetic acid;

[3-(4-chloro-phenyl)-7-iodo-2,5-dioxo-1,2,3,5-tetrahydro-benzo[e][1,4]diazepin-4-yl]-(4-isopropyl-phenyl)-acetic acid;

(4-chloro-phenyl)-[3-(4-chloro-phenyl)-7-cyano-2,5-dioxo-1,2,3,5-tetrahydro-benzo[e][1,4]diazepin-4-yl]-acetic acid;

3-(4-chloro-phenyl)-4-(3-hydroxy-1-phenyl-propyl)-7-iodo-3,4-dihydro-1H-benzo[e][1,4]diazepine-2,5-dione;

2-(4-chloro-phenyl)-2-[3-(4-chloro-phenyl)-7-iodo-2,5-dioxo-1,2,3,5-tetrahydro-benzo[e][1,4]diazepin-4-yl]-N-hydroxy-acetamide;

[7-bromo-3-(4-chloro-phenyl)-2,5-dioxo-1,2,3,5-tetrahydro-benzo[e][1,4]diazepin-4-yl]-(4-chloro-phenyl)-acetic acid;

[8-chloro-3-(4-chloro-phenyl)-7-iodo-2,5-dioxo-1,2,3,5-tetrahydro-benzo[e][1,4]diazepin-4-yl]-(4-chloro-phenyl)-acetic acid;

5-{2-(4-chloro-phenyl)-2-[3-(4-chloro-phenyl)-7-iodo-2,5-dioxo-1,2,3,5-tetrahydro-benzo[e][1,4]diazepin-4-yl]-acetylamino}-pentanoic acid;

3-{2-(4-chloro-phenyl)-2-[3-(4-chloro-phenyl)-7-iodo-2,5-dioxo-1,2,3,5-tetrahydro-benzo[e][1,4]diazepin-4-yl]-acetylamino}-propionic acid;

5-[4-[carboxy-(4-chloro-phenyl)-methyl]-3-(4-chlorophenyl)-7-iodo-2,5-dioxo-2,3,4,5-tetrahydro-benzo[e][1,4]diazepin-1-yl]-pentanoic acid;

and pharmaceutically-acceptable salts thereof.

23. The compound of claim 1, wherein said compound is selected from the group consisting of:

(4-chlorophenyl)-[3-(4-chlorophenyl)-7-iodo-5-oxo-1,2,3,5-tetrahydro-benzo[e][1,4]diazepin-4-yl]acetic acid;

3-(4-chloro-phenyl)-3-[3-(4-chloro-phenyl)-7-iodo-5-oxo-1,2,3,5-tetrahydro-benzo[e][1,4]diazepin-4-yl]-propionic acid;

(4-chloro-phenyl)-[3-(4-chloro-phenyl)-7-iodo-5-oxo-2-thioxo-1,2,3,5-tetrahydro-benzo[e][1,4]diazepin-4-yl]-acetic acid;

3-(4-chloro-phenyl)-4-[1-(4-chloro-phenyl)-2-hydroxy-ethyl]-7-iodo-1,3,4,5-tetrahydro-benzo[e][1,4]diazepin-2-one;

3-(4-chloro-phenyl)-4-[1-(4-chloro-phenyl)-2-hydroxy-ethyl]-7-iodo-1,2,3,4-tetrahydro-benzo[e][1,4]diazepin-5-one; and pharmaceutically-acceptable salts thereof.

24. A compound according to claims 1, in the form of a hydrochloride, acetate, trifluoroacetate or fumarate salt.

25. A pharmaceutical composition, comprising:
(a) a compound of 1, or a salt, hydrate or prodrug thereof; and
(b) one or more pharmaceutically-acceptable excipients.

26. The composition of claim 25, wherein the composition is sterile.

27. The composition of claim 25, further comprising:
(c) at least one additional substance selected from the group consisting of synergists, stabilizing substances, antineoplastic agents, anticancer agents, and cytostatic agents.

28. The composition of claim 25, wherein said compound is present in an amount between about 0.5 and about 100 milligrams.

29. The composition of claim 25, suitable for administration by a subcutaneous, intravenous, intramuscular, intraperitoneal, buccal, or ocular route, rectally, parenterally, instrasystemically, intravaginally, topically, orally, or as an oral or nasal spray.

30. The composition of claim 25, suitable for parenteral administration, wherein said compound is present in an amount between about 0.5 and about 100 milligrams.

31. The composition of claim 25, suitable for parenteral administration, wherein said compound is present in an amount between about 0.5 and about 10 milligrams.

32. The composition of claim 25, suitable for oral administration, wherein said compound is present in an amount between about 0.5 and about 100 milligrams.

33. The composition of claim 25, suitable for oral administration, wherein said compound is present in an amount between about 25 and about 100 milligrams.

* * * * *